(12) United States Patent
Kunas et al.

(10) Patent No.: US 10,640,741 B2
(45) Date of Patent: *May 5, 2020

(54) STIRRED TANK REACTOR SYSTEMS AND METHODS OF USE

(71) Applicants: LIFE TECHNOLOGIES CORPORATION, Carlsbad, CA (US); Baxalta Incorporated, Bannockburn, IL (US); Baxalta GmbH, Glattpark (Opfikon) (CH)

(72) Inventors: Kurt T. Kunas, Thousand Oaks, CA (US); Robert V. Oakley, Lafayette, CA (US); Fauad F. Hasan, Santa Clara, CA (US); Michael E. Goodwin, Logan, UT (US); Jeremy K. Larsen, Providence, UT (US); Nephi D. Jones, Newton, UT (US)

(73) Assignees: Life Technologies Corporation, Carlsbad, CA (US); Baxalta Incorporated, Bannockburn, IL (US); Baxalta GMBH, Glattpark (Opfikon) (CH)

( * ) Notice: Subject to any disclaimer, the term of this patent is extended or adjusted under 35 U.S.C. 154(b) by 247 days.

This patent is subject to a terminal disclaimer.

(21) Appl. No.: 15/376,362

(22) Filed: Dec. 12, 2016

(65) Prior Publication Data

US 2017/0088806 A1 Mar. 30, 2017

Related U.S. Application Data

(60) Continuation of application No. 14/109,684, filed on Dec. 17, 2013, now Pat. No. 9,540,606, which is a (Continued)

(51) Int. Cl.
*C12M 1/00* (2006.01)
*C12M 1/06* (2006.01)
(Continued)

(52) U.S. Cl.
CPC ............. *C12M 23/14* (2013.01); *B01F 7/001* (2013.01); *B01F 7/1695* (2013.01); *B01F 7/22* (2013.01);
(Continued)

(58) Field of Classification Search
CPC .......... B01F 7/001; B01F 7/1695; B01F 7/22; B01F 15/00006; B01F 15/00831; B01F 15/0085; B01F 2215/0073; C12M 23/14; C12M 29/06; Y10T 29/49826
See application file for complete search history.

(56) References Cited

U.S. PATENT DOCUMENTS 2,162,400 A 6/1939 Heath
2,797,903 A 7/1957 Urban
(Continued)

FOREIGN PATENT DOCUMENTS

CH 340 486 8/1959
DE 102 01 811 7/2003
(Continued)

OTHER PUBLICATIONS

Supplemental EP Search Report dated Oct. 10, 2012 issued in EP 06758475, filed Apr. 21, 2006.
(Continued)

*Primary Examiner* — Michael L Hobbs
(74) *Attorney, Agent, or Firm* — Workman Nydegger

(57) ABSTRACT

A reactor system includes a support housing having an interior surface bounding a chamber, the chamber having a vertically extending central longitudinal axis. A flexible bag is disposed within the chamber of the support housing and has an interior surface bounding a compartment. A mixing element is disposed within the compartment of the flexible bag. A drive element, such as a drive shaft, is secured the mixing element, wherein the mixing element is laterally offset from and/or is angled relative to the vertically extending central longitudinal axis of the support housing.

23 Claims, 33 Drawing Sheets

Related U.S. Application Data continuation of application No. 13/443,391, filed on Apr. 10, 2012, now Pat. No. 8,623,640, which is a division of application No. 13/014,575, filed on Jan. 26, 2011, now Pat. No. 8,187,867, which is a division of application No. 12/116,050, filed on May 6, 2008, now Pat. No. 7,901,934, which is a division of application No. 11/112,834, filed on Apr. 22, 2005, now Pat. No. 7,384,783.

(60) Provisional application No. 60/565,908, filed on Apr. 27, 2004.

(51) Int. Cl.
  *B01F 7/00* (2006.01)
  *B01F 7/16* (2006.01)
  *B01F 7/22* (2006.01)
  *B01F 15/00* (2006.01)
  *C12M 1/12* (2006.01)

(52) U.S. Cl.
  CPC .... *B01F 15/00006* (2013.01); *B01F 15/0085* (2013.01); *B01F 15/00831* (2013.01); *C12M 23/00* (2013.01); *C12M 23/06* (2013.01); *C12M 23/26* (2013.01); *C12M 23/28* (2013.01); *C12M 27/02* (2013.01); *C12M 29/06* (2013.01); *B01F 2215/0073* (2013.01); *Y10T 29/49826* (2015.01)

(56) References Cited

U.S. PATENT DOCUMENTS

| | | | |
|---|---|---|---|
| 3,647,397 A | 3/1972 | Coleman | |
| 4,125,697 A * | 11/1978 | Pettelkau | C08F 36/18 422/135 |
| 4,711,582 A | 12/1987 | Kennedy | |
| 4,721,003 A | 1/1988 | Hutchings et al. | |
| 4,805,799 A | 2/1989 | Robbins, III | |
| 4,828,395 A | 5/1989 | Saito et al. | |
| 4,879,529 A | 11/1989 | Schroth et al. | |
| 4,964,333 A | 10/1990 | Bravo | |
| 4,968,624 A | 11/1990 | Bacehowski et al. | |
| 5,422,043 A | 6/1995 | Burris | |
| 5,458,771 A | 10/1995 | Todd | |
| 5,584,577 A | 12/1996 | Thies | |
| 5,727,878 A | 3/1998 | Sullivan, Jr. | |
| 5,799,380 A | 9/1998 | Carroll et al. | |
| 5,858,283 A | 1/1999 | Burris | |
| 5,941,635 A | 8/1999 | Stewart | |
| 5,988,422 A | 11/1999 | Vallot | |
| 6,071,005 A | 6/2000 | Ekambaram et al. | |
| 6,076,457 A | 6/2000 | Vallot | |
| 6,083,587 A | 7/2000 | Smith et al. | |
| 6,245,555 B1 | 6/2001 | Curtis | |
| 6,494,613 B2 | 12/2002 | Terentiev | |
| 6,655,655 B1 | 12/2003 | Matkovich et al. | |
| 6,670,171 B2 | 12/2003 | Carll | |
| 6,709,862 B2 | 3/2004 | Curtis | |
| 6,773,678 B2 | 8/2004 | Cummings et al. | |
| 6,908,223 B2 | 6/2005 | Bibbo et al. | |
| 6,981,794 B2 | 1/2006 | Bibbo et al. | |
| 7,070,318 B2 | 7/2006 | Renfro | |
| 7,153,021 B2 | 12/2006 | Goodwin et al. | |
| 7,348,783 B1 * | 3/2008 | Hsiung | G01N 27/4167 324/438 |
| 7,384,783 B2 | 6/2008 | Kunas et al. | |
| 7,442,538 B2 | 10/2008 | Bragos Bardia et al. | |
| 7,469,884 B2 | 12/2008 | Terentiev et al. | |
| 7,487,688 B2 | 2/2009 | Goodwin | |
| 7,682,067 B2 | 3/2010 | West et al. | |
| 7,901,934 B2 | 3/2011 | Kunas et al. | |
| 8,282,267 B2 | 10/2012 | Castillo et al. | |
| 8,623,640 B2 * | 1/2014 | Kunas | B01F 7/001 366/150.1 |
| 9,540,606 B2 * | 1/2017 | Kunas | B01F 7/001 |
| 9,682,067 B2 * | 6/2017 | Barkai | A61K 31/401 |
| 9,700,857 B1 * | 7/2017 | Larsen | B01F 7/00691 |
| 2002/0105856 A1 * | 8/2002 | Terentiev | B01F 7/0005 366/262 |
| 2002/0145940 A1 | 10/2002 | Terentiev | |
| 2003/0198406 A1 | 10/2003 | Bibbo et al. | |
| 2003/0228684 A1 | 12/2003 | Burbidge et al. | |
| 2003/0231546 A1 | 12/2003 | Bibbo et al. | |
| 2004/0062140 A1 | 4/2004 | Cadogan et al. | |
| 2004/0136265 A1 | 7/2004 | Meier et al. | |
| 2004/0171302 A1 | 9/2004 | Matkovich et al. | |
| 2004/0190372 A1 | 9/2004 | Goodwin et al. | |
| 2005/0002274 A1 | 1/2005 | Terentiev | |
| 2005/0078552 A1 * | 4/2005 | Zambaux | B01F 7/1695 366/241 |
| 2005/0255587 A1 | 11/2005 | Bragos Bardia et al. | |
| 2005/0272146 A1 | 12/2005 | Hodge et al. | |
| 2005/0276158 A1 | 12/2005 | Thomas | |
| 2006/0131765 A1 | 6/2006 | Terentiev et al. | |
| 2008/0068920 A1 | 3/2008 | Galliher et al. | |
| 2008/0206847 A1 | 8/2008 | Kunas et al. | |
| 2009/0035856 A1 | 2/2009 | Galliher et al. | |
| 2009/0242173 A1 | 10/2009 | Mitchell et al. | |
| 2009/0311755 A1 | 12/2009 | Harris et al. | |
| 2010/0015696 A1 | 1/2010 | Claes et al. | |
| 2011/0013474 A1 | 1/2011 | Ludwig et al. | |
| 2011/0310696 A1 | 12/2011 | Goodwin et al. | |
| 2012/0027324 A1 | 2/2012 | Morrissey et al. | |
| 2012/0132549 A1 | 5/2012 | Galliher et al. | |
| 2012/0155216 A1 | 6/2012 | Morrissey et al. | |
| 2012/0282688 A1 | 11/2012 | Knight et al. | |
| 2013/0089925 A1 | 4/2013 | Damren et al. | |
| 2013/0121103 A1 | 5/2013 | Castillo et al. | |
| 2014/0106453 A1 | 4/2014 | Kunas et al. | |

FOREIGN PATENT DOCUMENTS

| | | |
|---|---|---|
| DE | 102005062052 A1 | 6/2007 |
| DE | 102006020706 A1 | 11/2007 |
| EP | 0 239 962 | 10/1987 |
| EP | 0343885 A1 | 11/1989 |
| GB | 1 172 653 | 12/1969 |
| GB | 2202549 A | 9/1988 |
| JP | 60-151400 | 10/1985 |
| JP | 63-224727 | 9/1988 |
| JP | 1-180228 | 7/1989 |
| JP | 2-035925 | 2/1990 |
| JP | 2-057174 | 2/1990 |
| JP | 04-055795 | 2/1992 |
| JP | 5-284966 | 11/1993 |
| JP | 6-285353 | 10/1994 |
| JP | 8-108057 | 4/1996 |
| JP | 3042470 | 8/1997 |
| JP | 10-073164 | 3/1998 |
| JP | 11-028346 | 2/1999 |
| JP | 1997-0197839 | 2/1999 |
| JP | 2001-224938 | 8/2001 |
| JP | 2004-532719 | 10/2004 |
| JP | 2004-534544 | 11/2004 |
| JP | 2005-080662 | 3/2005 |
| JP | 2006-507823 | 3/2006 |
| WO | 2004/048510 | 6/2004 |
| WO | 2005/068059 | 7/2005 |
| WO | 2005/104706 | 11/2005 |
| WO | 2007/134267 A2 | 11/2007 |
| WO | 2008/088371 A2 | 7/2008 |
| WO | 2012/015571 A1 | 2/2012 |
| WO | 2012/125730 A2 | 9/2012 |

OTHER PUBLICATIONS

Office Action dated Aug. 3, 2010 in U.S. Appl. No. 12/116,050, filed May 6, 2008.
Notice of allowance and issue fee dated Jan. 3, 2011 in U.S. Appl. No. 12/116,050, filed May 6, 2008.

(56) References Cited

OTHER PUBLICATIONS

Office Action dated Aug. 2, 2011 in U.S. Appl. No. 13/014,575, filed Jan. 26, 2011.
Notice of allowance and issue fee dated Jan. 3, 2012 in U.S. Appl. No. 13/014,575, filed Jan. 26, 2011.
American Fluoroseal Corporation, website printouts, www.teflonbag.com, Feb. 11, 2000, 11 pages.
Office Action dated Oct. 6, 2011 in Canadian Application No. 2,559,537, filed Apr. 22, 2005.
Office Action dated Oct. 4, 2007 in U.S. Appl. No. 11/112,834, filed Apr. 22, 2005.
Notice of allowance and issued fee dated Mar. 7, 2008 in U.S. Appl. No. 11/112,834, filed Apr. 22, 2005.
Office Action dated Aug. 13, 2009 in U.S. Appl. No. 11/379,535, filed Apr. 20, 2006.
Notice of allowance and issue fee dated Dec. 1, 2009 in U.S. Appl. No. 11/379,535, filed Apr. 20, 2006.
International Search report dated Feb. 22, 2007 in PCT Application No. PCT/US2006/015176, filed Apr. 21, 2006.
Office Action dated Sep. 25, 2012 in U.S. Appl. No. 13/443,391, filed Apr. 10, 2012.
Office Action dated Sep. 25, 2009 in Chinese Application No. 200580013197.1, filed Oct. 26, 2006.
Office Action dated Aug. 4, 2010 in Chinese Application No. 200580013197.1, filed Oct. 26, 2006.
Office Action dated Nov. 29, 2010 in Chinese Application No. 200580013197.1, filed Oct. 26, 2006.
Office Action dated Feb. 10, 2011 in Chinese Application No. 200580013197.1, filed Oct. 26, 2006.
Office Action dated Aug. 23, 2011 in Chinese Application No. 200580013197.1, filed Oct. 26, 2006.
Examination report dated Aug. 14 2012 in Canadian Application No. 2603467, filed Apr. 21, 2006.
EP Office Action dated Aug. 19, 2009 in European Application No. 05739820.8, filed Nov. 9, 2006.
EP Office Action dated Aug. 19, 2009 in European Application No. 05739820.8, filed Jul. 6, 2012.
Indian Office Action dated Jun. 20, 2009 in Application No. 2015DELNP2006, filed Aug. 31, 2008.
Indian Office Action dated Jun. 20, 2009 in Application No. 2015DELNP2006, filed May 4, 2010.
Japanese Office Action dated Dec. 10, 2012 in Application No. 2008-519763, filed Apr. 22, 2005.
Japanese Office Action dated Dec. 10, 2012 in Application No. 2008-519763, filed Oct. 26, 2011.

\* cited by examiner

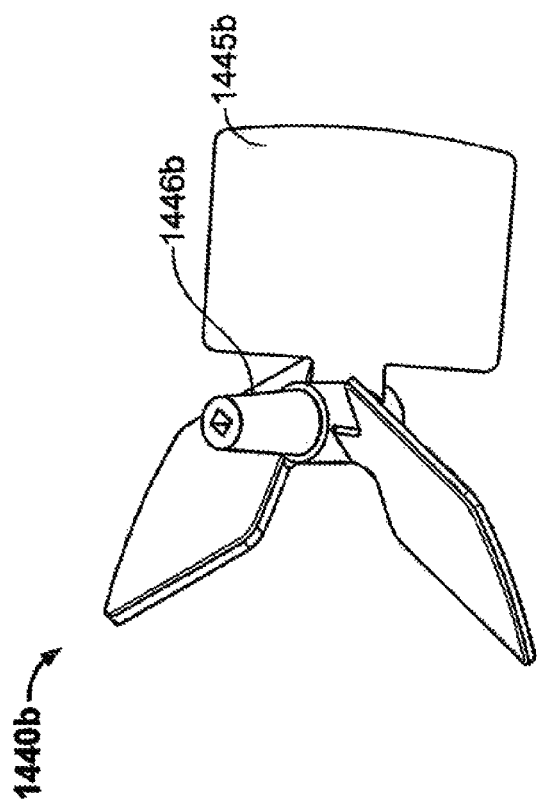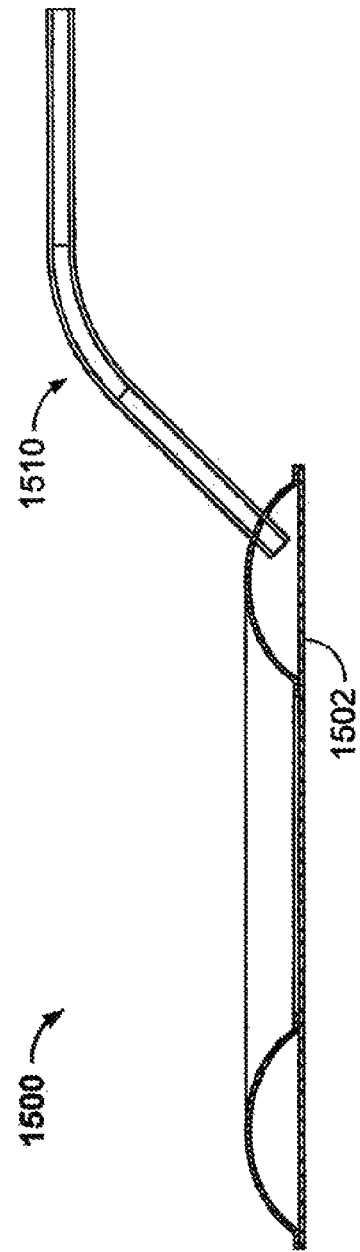

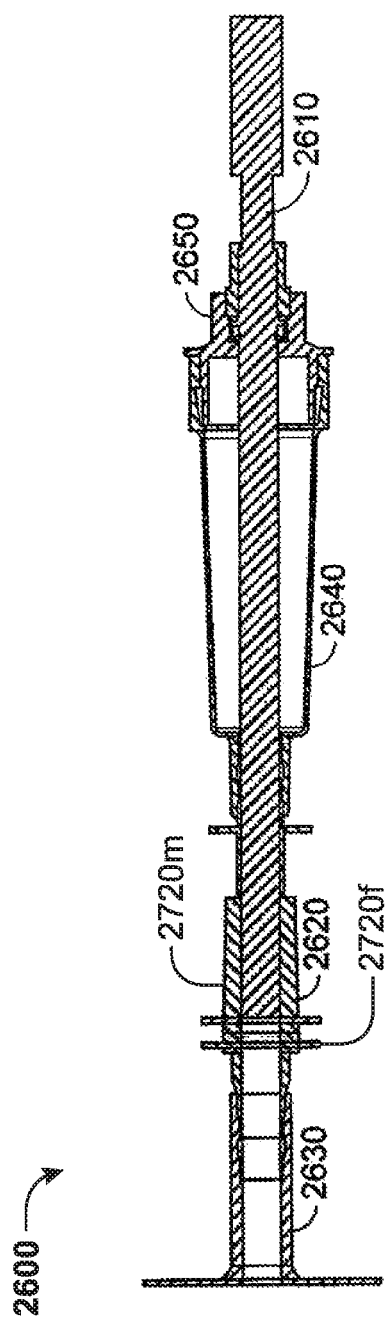

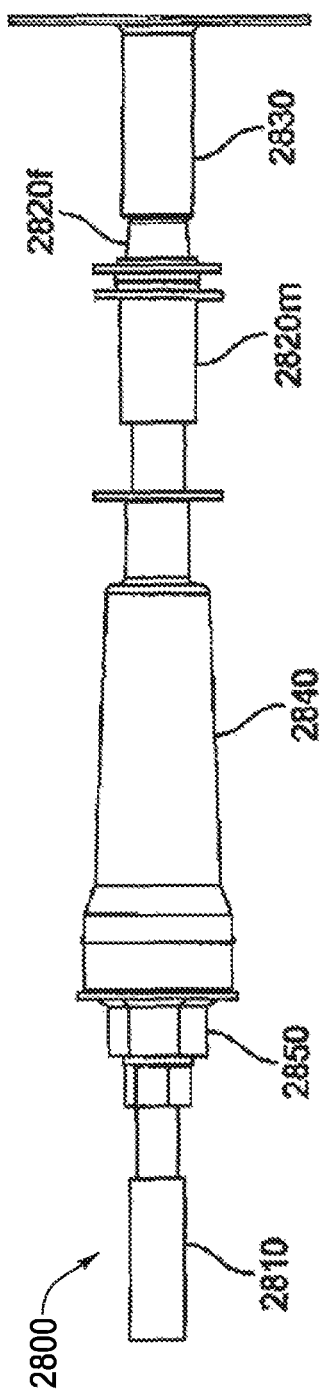
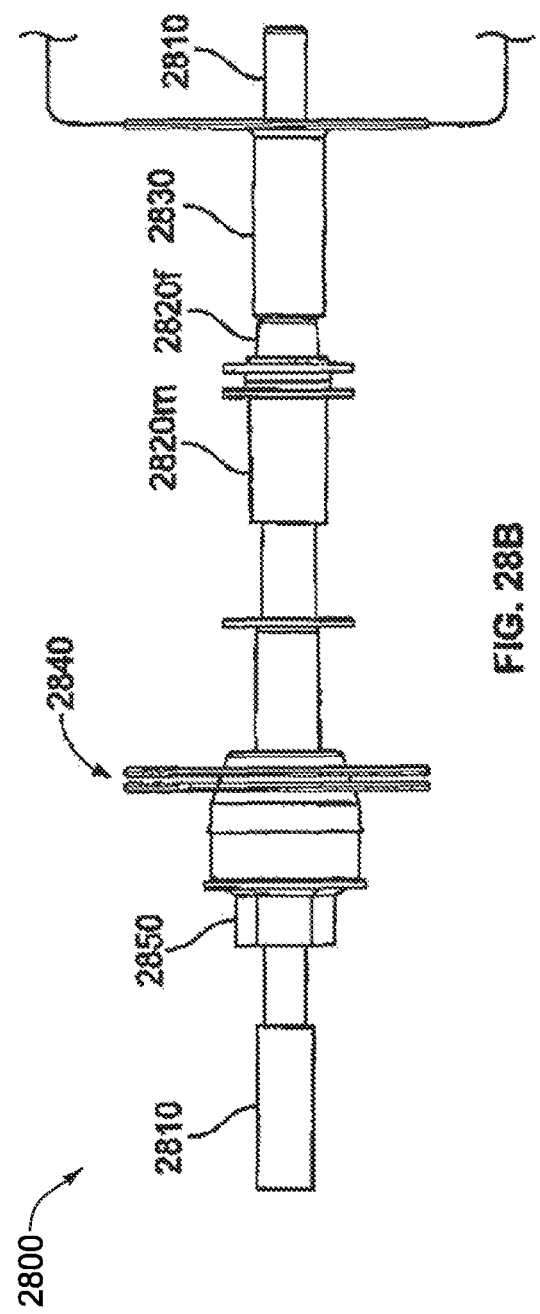
FIG. 28A
FIG. 28B

STIRRED TANK REACTOR SYSTEMS AND METHODS OF USE

CROSS-REFERENCE TO RELATED APPLICATION

This application is a continuation of U.S. application Ser. No. 14/109,684, filed Dec. 17, 2013, U.S. Pat. No. 9,540,606, which is a continuation of U.S. application Ser. No. 13/443,391, filed Apr. 10, 2012, U.S. Pat. No. 8,623,640, which is a divisional of U.S. application Ser. No. 13/014,575, filed Jan. 26, 2011, U.S. Pat. No. 8,187,867, which is a divisional of U.S. application Ser. No. 12/116,050, filed May 6, 2008, U.S. Pat. No. 7,901,934, which is a divisional of U.S. application Ser. No. 11/112,834, filed Apr. 22, 2005, U.S. Pat. No. 7,384,783, which claims the benefit of U.S. Provisional Application Ser. No. 60/565,908, filed Apr. 27, 2004, which applications are incorporated herein in their entirety by specific reference.

BACKGROUND OF THE INVENTION

1. The Field of the Invention

The present invention relates to a stirred-tank reactor system and methods of use. The present invention further encompasses the use of the stirred-tank reactor system as a disposable bioreactor and in kits with disposable elements.

2. The Relevant Technology

Bioreactors or fermenters include containers used for fermentation, enzymatic reactions, cell culture, biologicals, chemicals, biopharmaceuticals, tissue engineering, microorganisms, plant metabolites, food production and the like. Bioreactors vary in size from benchtop fermenters to stand-alone units of various sizes. The stringent asepsis requirements for sterile production in some bioreactors can require elaborate systems to achieve the desired product volumes. Consequently, the production of products in aseptic bioreactors can be costly which provides the motivation for pursuing improved systems.

Conventional bioreactors perfuse nutrient media through a single type of hollow fiber. The various disadvantages of such bioreactors may include heterogeneous cell mass, difficult procurement of representative cell growth samples, poor performance due to inefficient oxygenation and an inability to control oxygen levels, and problems with contamination of cell cultures. Moreover, micro-environmental factors such as pH may not be effectively controlled and a mixed culture or co-culture of cells may not be possible. Some known bioreactors include a reaction container, through which a central strand of porous hollow fibers extends, through which a nutrient solution is pumped. This central strand of hollow fibers is concentrically surrounded by a plurality of strands of hollow fibers, through which a gaseous medium is conveyed. The hollow fibers of these strands are also constituted in such a manner that the gaseous medium—for example oxygen or carbon dioxide—can at least partly emerge from these strands or enter into these strands respectively. This type of bioreactor can achieve enhanced nutrient media oxygenation as compared to other known devices. However, occasional contamination of cell cultures and an inability to control pH levels effectively may continue to present difficulties.

The expense of producing cells, biopharmaceuticals, biologicals and the like in aseptic bioreactors is often exacerbated by the required cleaning, sterilization and validation of the standard bioreactors (i.e., stainless steel or glass reactors). Attempts have been made to solve this problem with the development of pre-sterilized disposable bioreactor systems that need not be cleaned, sterilized or validated by end users. The use of such disposable bioreactor systems could provide significant savings. Furthermore, plastics are lightweight, easy to transport, and require less room than stainless steel or glass reactors. Some have reported the use of disposable elements in bioreactors that include a reactor chamber with a support housing. The interior chamber of the support housing is lined with a disposable liner and sealed with a head plate attached to the liner to form a sealed chamber. As the liner is open at the top, it is typically used in a vertically oriented bioreactor to prevent the contamination of the head plate. Although this system provides a disposable liner, the head plate and the interior chamber may still require cleaning and sterilization.

Others have attempted to develop flexible, disposable plastic vessels that do not require cleaning or sterilization and require only minimal validation efforts. Such approaches can include a flexible, disposable, and gas permeable cell culture chamber that is horizontally rotated. The cell culture chamber is made of two sheets of plastic fused together. In addition, the culture chamber is made of gas permeable material and is mounted on a horizontally rotating disk drive that supports the flexible culture chamber without blocking airflow over the membrane surfaces. The chamber is placed in an incubator and oxygen transfer is controlled by controlling the gas pressure in the incubator according to the permeability coefficient of the bag. The rotation of the bag assists in mixing the contents of the bag. However, the cell culture chamber will often be limited to use within a controlled gas environment. Particularly, the cell culture chamber may have no support apparatus and may be limited to small volumes. Furthermore, the chamber may not provide an inlet and an outlet for media to be constantly pumped into and out of the chamber during rotation.

Some companies have developed a range of pre-sterile, disposable bioreactors that do not require cleaning or sterilizing. Such reactors are made of sheets of flexible, gas impermeable material to form a bag. The bag is partially filled with media and then inflated with air that continually passes through the bag's headspace. The media is mixed and aerated by rocking the bags to increase the air-liquid interface. However, since there is typically no solid housing that supports the bags, the bags may become cumbersome and difficult to handle as they increase in size. Furthermore, the wave action within the rocking bag can create damaging turbulent forces. Certain cell cultures, particularly human cell cultures, may benefit from more gentle conditions.

Thus, there is a continuing need to develop flexible, pre-sterilized, disposable bioreactors that are easy to handle and require little training to operate, yet provide the necessary gas transfer and nutrient mixing required for successful cell and tissue cultures. Such disposable bioreactors would be equally useful for the production of chemicals, biopharmaceuticals, biologicals, cells, microorganisms, plant metabolites, foods and the like.

BRIEF SUMMARY OF THE INVENTION

In a first aspect, the present invention provides a stirred-tank reactor system with disposable elements, such as a flexible plastic bag with an attached bearing, shaft, and impeller assembly. The instant invention further relates to the use of this novel stirred-tank reactor system as a disposable bioreactor and in kits with disposable elements. The advantages of the present invention are numerous. Particularly, the stirred-tank reactor system may be pre-sterilized and does not require a steam-in-place (SIP) or clean-in-place (CIP) environment for changing from batch to batch or product to product in a culture or production system. As such, the system may require less regulatory control by assuring zero batch-to-batch contamination and can, thus, be operated at a considerable cost-advantage and with minimal or no preparation prior to use. In addition, the system can be a true stirred-tank reactor system unlike other disposable reactor systems. This provides the added advantage that the instant invention can offer a hydrodynamic environment that can be scaled to various sizes similar to conventional non-disposable reactor systems. As the system typically does not require cleaning or sterilizing, it combines a flexible, easy-to-use, true stirred-tank reactor environment with zero cross-contamination during the cell culture or production process.

One aspect of the present invention provides a stirred-tank reactor system, comprising a flexible bag with at least one opening, wherein the bag functions as a sterile container for a fluidic medium; a shaft situated within the bag; an impeller attachable to the shaft, wherein the impeller is used to agitate the fluidic medium to provide a hydrodynamic environment; and a bearing attached to the shaft and to the opening of the bag. The bag may be affixed to the shaft and the bearing through at least one seal or O-ring such that the inside of the bag remains sterile. The seals or O-rings can be affixed to the bag. The system may be disposable and pre-sterilized. The bag may further include a pH sensor and a dissolved-oxygen sensor, wherein the sensors are incorporated into the bag. In addition, the system may include at least one internal pouch sealed to the bag, wherein the pouch has one end that can be opened to the outside of the bag such that a probe (i.e., a temperature probe, a pH probe, a dissolved gas sensor, an oxygen sensor, a carbon dioxide ($CO_2$) sensor, a cell mass sensor, a nutrient sensor, an osmometer, and the like) can be inserted into the reactor. The system may also include at least one port in the bag allowing for the connection of a device such as a tube, a filter, a sampler, a probe, or a connection device to the port. A port allows for sampling; gas flow in and out of the bag; liquid or media flow in and out of the bag; inoculation; titration; adding of chemostat reagents; sparging; and the like.

Another aspect of the present invention provides a stirred-tank reactor system, comprising a flexible bag with at least one opening, wherein the bag functions as a sterile container for a fluidic medium; a shaft situated within the bag; an impeller attachable to the shaft, wherein the impeller is used to agitate the fluidic medium to provide a hydrodynamic environment; and a bearing attached to the shaft and to the opening of the bag. The system may further include a housing, such as a reactor housing, on the outside of the bag, wherein the housing includes at least one support that holds the bearing and a motor, and wherein the bag is contained within the housing. The housing may further include a plurality of baffles such that the bag folds around the baffles. Optionally, the system further encompasses a heater (e.g., a heating pad, a steam jacket, a circulating fluid or water heater, etc.) that can be located between the bag and the housing. Alternatively, the heater may be incorporated into the housing (e.g., a permanent reactor housing with incorporated heating system).

In another aspect of the invention, the stirred-tank reactor system includes a permanent housing with a product loop with flow past a pH sensor and a dissolved-oxygen sensor, wherein the sensors are incorporated into the housing. The permanent housing includes, but is not limited to, a metal barrel, a plastic barrel, a wood barrel, a glass barrel, and the like.

The invention also contemplates a method for preparing a stirred-tank reactor system, comprising providing a flexible bag with at least one opening, wherein the bag functions as a sterile container for a fluidic medium; inserting a shaft with an impeller attachable to the shaft into the bag, wherein the impeller is used to agitate the fluidic medium to provide a hydrodynamic environment; attaching a bearing to the shaft and to the opening of the bag; and sealing the bag to the shaft and the bearing such that the inside of the bag remains sterile. The stirred-tank reactor system prepared by this method includes at least one disposable element including, but not limited to, the bag, the shaft, the impeller, and the bearing.

The invention further encompasses a kit comprising a stirred-tank reactor system and instructions for use. The kit includes a disposable stirred-tank reactor system. The kit may also include a stirred-tank reactor system with at least one disposable element such as the bag, the shaft, the impeller, or the bearing. The bag may be affixed to the shaft and the bearing through at least one seal or O-ring such that the inside of the bag remains sterile. Furthermore, the bag may include a pH sensor and a dissolved-oxygen sensor, wherein the sensors are incorporated into the bag. The kit may also include at least one internal pouch sealed to the bag, wherein the pouch includes one end that can be opened to the outside of the bag such that a probe can be inserted into the reactor. In addition, the system may include at least one port in the bag allowing for the connection of a device to the port, wherein the device includes, but is not limited to, a tube, a filter, a sampler, and the like.

Another aspect of the invention provides a bag for use in a stirred-tank reactor system. The bag may be a disposable, flexible, plastic bag. The bag may also include at least one disposable element including, but not limited to, a seal, an O-ring, a port, a pouch, a tube, a filter, a sampler, a probe, a sensor, a connection device, or the like.

In one aspect, the present invention provides a reactor system that includes a container and a rotational assembly. The rotational assembly can be in sealed cooperation with an opening of a container. The rotational assembly can include a rotatable hub adapted to receive and releasably couple with a drive shaft, such that when the drive shaft is operatively coupled with the rotatable hub, rotation of the drive shaft facilitates a corresponding rotation of the rotatable hub. In a related aspect, the system can further include an impeller coupled with the rotatable hub, such that the impeller is disposed within the container and adapted to couple with a distal end of the drive shaft. In other aspects, the rotational assembly can include a casing, whereby the rotational assembly is in sealed cooperation with the opening of the container via the casing. Similarly, the system can include a drive shaft, wherein the rotatable hub and the drive shaft are disposed to rotate relative to the casing. In still a related aspect, the rotational assembly can include a bearing assembly disposed between the casing and the rotatable hub. The rotational assembly may further include a sealing arrangement disposed circumferentially to the rotatable hub, between the rotatable hub and the casing. Relatedly, the bearing assembly can include a plurality of race bearings, and the sealing arrangement can include a rotating disk coupled with the rotatable hub, a wear plate coupled with the casing, and a dynamic seal disposed between the rotating disk and the wear plate. In other aspects, a seal can include two or more seal subunits disposed in co-planar arrangement. Relatedly, a bearing assembly can include a journal bearing, and the sealing arrangement can include a wear plate coupled with the rotatable hub, and a dynamic seal disposed between the casing and the wear plate. In a similar aspect, the impeller can include a spline adapted to couple with the drive shaft. Often, the container can comprise a flexible bag. In another aspect, the rotatable hub can be coupled with the impeller via a flexible tube.

In one aspect, the present invention provides a reactor system that includes a container and a sparger assembly. The sparger assembly can be disposed within the container, and can include a flexible sheet of permeable material and a sparger conduit. In a related aspect, the sheet of permeable material can include a vapor-permeable and water-resistant material. In some aspects, the sheet of permeable material can include a high density polyethylene fiber. In related aspects, the sparger assembly can be in fluid communication with a port of the container. Similarly, the reactor system may include a rotational assembly in sealed cooperation with an opening of the container, and an impeller disposed within the container and coupled with the rotational assembly. The sparger body may be anchored to an interior surface of the container, and in some cases, the sparger body of the sparger assembly can be in a substantially spherical shape.

In another aspect, the present invention provides a bioreactor system that includes a frame support coupled with a drive motor; a flexible bag disposed within a housing of the frame support. The flexible bag can include one or more ports for introducing a cell culture and a medium into the flexible bag; a rotational assembly coupled with a bracket of the frame support and in sealed cooperation with an opening of the flexible bag. The rotational assembly can include a hub adapted to house and couple with a drive shaft of the drive motor. The system can also include an impeller coupled with the hub for agitating the cell culture and medium. The impeller can be disposed within the flexible bag and adapted to couple with the drive shaft. In one aspect, the bioreactor system can include a probe assembly. The probe assembly can include a port coupled with the flexible bag, a PALL connector coupled with the port, a sleeve coupled with the PALL connector, a coupler coupled with the sleeve, and a probe configured to be coupled with the coupler and inserted through the sleeve, PALL connector, and port, and partially into the flexible bag.

In one aspect, the present invention provides a method for manufacturing a reactor system. The method can include coupling a container with a rotational assembly. The rotational assembly can be in sealed cooperation with an opening of the container. The rotational assembly can include a hub adapted to house and couple with a drive shaft. The method may also include coupling an impeller with the hub, where the impeller is disposed within the container. The method may further include sterilizing the reactor system. In a related aspect, the sterilizing step can include treating the system with gamma radiation.

In another aspect, the present invention provides a method for preparing a reactor system. The method can include coupling a casing of a rotational assembly of the reactor system to a frame bracket. The method can also include placing a container of the reactor system at least partially within a frame housing, and inserting a drive shaft into a hub of the rotational assembly. The hub can be disposed within the casing of the rotational assembly between a bearing and the casing. The method can further include coupling a distal end of the drive shaft to an impeller. The impeller can be disposed within the container and coupled with the hub. The method can also include introducing a reaction component into the container via a port.

In one embodiment, the present invention provides a reactor system kit. The kit can have a reactor system that includes a container. The reactor system can also include a rotational assembly in sealed cooperation with an opening of the container. The rotational assembly can include a hub adapted to house and couple with a drive shaft, and an impeller coupled with the hub. The impeller can be disposed within the container and adapted to couple with the drive shaft. The kit also includes instructions for use.

BRIEF DESCRIPTION OF THE DRAWINGS

The present invention is best understood when read in conjunction with the accompanying figures which serve to illustrate the preferred embodiments. It is understood, however, that the invention is not limited to the specific embodiments disclosed in the figures.

FIG. 14B illustrates a perspective view of an impeller according to one embodiment of the present invention.

FIG. 15 illustrates a cross-section view of a sparger body according to one embodiment of the present invention.

FIG. 26 illustrates a probe assembly 2600 according to one embodiment of the present invention.

FIG. 28A illustrates a probe assembly according to one embodiment of the present invention.

FIG. 28B illustrates a probe assembly according to one embodiment of the present invention.

DETAILED DESCRIPTION OF THE INVENTION

Figure 1:
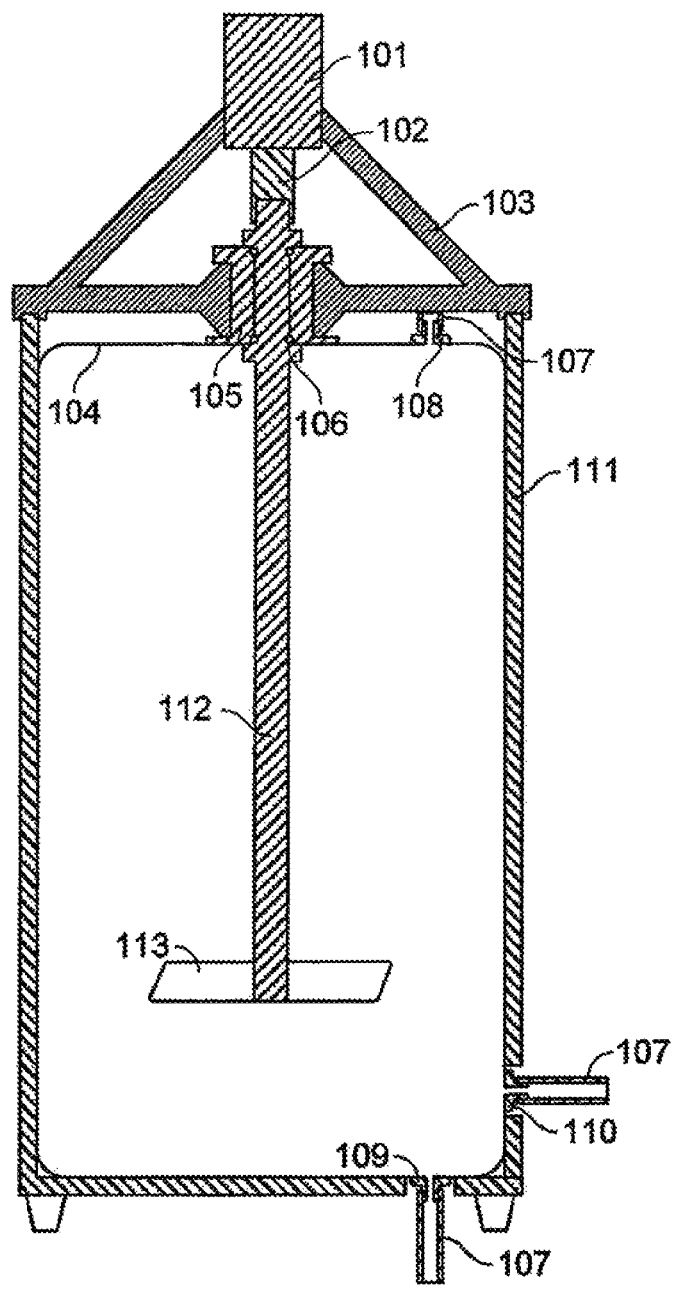
FIG. 1 depicts a longitudinal cross-section of one embodiment of the stirred-tank reactor system, wherein the stirred-tank reactor system is placed into a permanent housing.

In some embodiments, the term "flexible bag" can refer to a container that holds a fluidic medium. The bag may include one or more layer(s) of flexible or semi-flexible waterproof material depending on size, strength and volume requirements. The inside surface of the bag may be smooth and provide a sterile environment (e.g., for culturing cells or other organisms, for food production, etc.). The bag may include one or more openings, pouches (e.g., for inserting one or more probes, devices, etc.), ports (e.g., for the connection of one or more probes, devices, etc.) or the like. Furthermore, the bag can provide a disposable alternative to a solid vessel in a conventional stirred-tank bioreactor. The flexible bag may further include a shaft, an impeller, a bearing and seals or O-rings, and may be entirely disposable.

In some embodiments, the term "fluidic medium" can refer to any biological fluid, cell culture medium, tissue culture medium, culture of microorganisms, culture of plant metabolites, food production, chemical production, biopharmaceutical production, and the like. The fluidic medium is not limited to any particular consistency and its viscosity may vary from high to medium to low. When the fluidic medium is a cell culture medium the system may be operated in, for example, batch mode, semi-batch mode, fed-batch mode, or continuous mode.

In some embodiments, the term "impeller" can refer to a device that is used for agitating or mixing the contents of a stirred-tank reactor system (e.g., bioreactor). The impeller may agitate the fluidic medium by stirring or other mechanical motion. The impeller of the instant invention includes, but is not limited to, a Rushton, a marine, a hydrofoil, a pitched blade, and any other commercially available impeller.

In some embodiments, a "hydrodynamic" environment of the instant invention may refer to an environment that is influenced by the motion of fluids and the forces acting on solid bodies immersed in these fluids within the stirred-tank reactor system.

The present invention includes single use bioreactors, stirred tank reactors, and the like. Such reactors have a variety of applications, such as for the production of therapeutic proteins via batch cell culture. Relatedly, these systems can be used to provide for cell growth and antibody production for CHO and other cell lines. The hydrodynamic environment within the reactors can be well characterized, and, as such, may be scaled to other stirred tank bioreactors.

Single use bioprocess containers can be used for the storage of biopharmaceutical media, buffers, and other products. Using these storage container systems, several mixing systems for preparation of media and buffers can be developed, often to commercial scale up to 10,000 liters or more. Such mixing systems and bioreactors can use various means for mixing the reactor contents, such as a pulsating disk, a paddle mixer, a rocking platform, an impeller, and the like. These systems are well suited for use in chemical processing. The operating characteristics of the reactors can be well defined, and can be readily predicted and scaled to various sizes. In the biopharmaceutical industry, such stirred tank bioreactors can be established as a means for manufacture of biologic products from a wide range of biological systems, including animal cell culture. Processes for biological systems can be developed using stirred tank bioreactors at the bench scale and transferred to stirred tank bioreactors at the commercial scale, up to 10,000 liters or greater, using well established scale-up methodologies. For a stirred tank bioreactor, design parameters such as tip speed, power input, Reynolds number, and oxygen transfer coefficient can be readily determined and used for scale-up.

A single use portion of the system can include a flexible plastic container with the following single use integrated components: a bearing, shaft, and impeller assembly; a sparger assembly; ports for sterile attachment of sensor probes; and various ports for inlet and outlet of liquids and gases. A single use bioreactor can be manufactured using medical grade film. In some cases, other components of the single use bioreactor can be manufactured from readily machined materials that are not necessarily USP Class VI materials. The impeller can be a pitched-blade impeller that is attached to a bearing assembly by a flexible sheath. The impeller and sheath can rotate along with an inner bearing assembly, which is isolated from the exterior bearing assembly using various seal assemblies. An outer bearing assembly can be directly affixed to the single use container. A sparger can include a porous membrane that is sealed to the bottom of the single use container. Sparge gas can be introduced to the space between the porous membrane and bottom of the container through a port after passing through a pre-attached sterilization filter. The pH and $dO_2$ sensors may or may not be part of the single use container and can be connected to the bioreactor using PALL KLEENPACK® connectors. Industry-standard 12 mm sensors can be calibrated, then steam sterilized with one half of the connector. The other half of the connector can be pre-attached to the container, allowing the sensor to be inserted in direct contact with the reactor contents. Ports and tubing for headspace gas, thermo well, media inlet, titrant, sampling, harvest, and various pulse feeds can be pre-attached and pre-sterilized with the container.

A permanent support vessel that contains a motor and drive shaft assembly, heat jacket, and openings for inlets, outlets, and probes can hold a single use container. A drive shaft can fit through the single-use bearing, through the flexible sheath, and lock into the impeller. This shaft can be driven using a standard bioreactor mixer motor of sufficient power. Heat can be provided to the bioreactor contents, for example, by electric heat bands that are in direct contact with sides of the single-use container. The permanent support vessel can be mobile, and can be placed on a weigh scale for control of reactor volume.

The system can be operated using standard sensors and controllers that have industry-accepted track records of performance. In some embodiments, no control system may be required for steam sterilization or clean in place, and a controller commonly used for bench-scale bioreactors may be sufficient for control of the pH, $dO_2$ concentration, and temperature of the single use bioreactor. A single use bioreactor often requires no cleaning or sterilization in-place. As such, the capital and operating costs of control systems and utilities, such as clean steam, required for steam sterilization of a large pressure vessel may be eliminated. The cost for fabrication of a rigid-walled pressure vessel designed to handle the stresses exerted during steam-in-place sterilization may also be eliminated. Likewise, the capital and operating costs for clean-in-place control systems and utilities may be unnecessary. The design elements of traditional stainless steel vessels dictated by cleanability requirements may similarly be eliminated.

In some embodiments, a single use bioreactor can be a closed system that is discarded after use. This may eliminate the need for cleaning validation studies. The potential for cross contamination between production batches may also be reduced. In some embodiments, the capital expenditure required to accommodate multiple products simultaneously in single use bioreactors can be low compared to the cost of the fixed assets and utilities required to segregate traditional bioreactor systems. A single use bioreactor can be manufactured using medical grade film, and regulatory documentation for the film may be currently available. Other product contact components of a single use bioreactor can be manufactured from USP Class VI materials. Current applications of bioprocess containers manufactured from these materials include bioreactor feed and harvest, and transport and storage of bulk intermediate and final product.

As noted above, a stirred tank single use bioreactor according to the present invention can provide a well-characterized hydrodynamic environment for cell growth. Mixing characteristics can be readily calculated and can be translated to larger stirred tank reactors. Thus, processes developed at the lab or pilot scale may be scaled up directly to commercial scale, either in larger single use bioreactors or larger traditional stirred tank bioreactors. Scale-up parameters such as power input per unit volume, tip speed, oxygen transfer coefficient, or geometric similarity may be maintained at the larger scale. In some embodiments, the present invention provides a stirred tank reactor with a design that includes a rotating impeller driven by a drive shaft isolated through a series of rotating seals. Such designs can provide effective and efficient means of transmitting the energy required for mixing and mass transfer to the reactor contents.

The present invention can also include or be compatible with industry-standard sensor and controller technology. A standard that has developed in the industry is the use of 12 mm diameter pH and $dO_2$ sensors inserted through DN25 (Inglold-style) ports in direct contact with the reactor contents. Systems such as a single use bioreactor can incorporate the same 12 mm diameter pH and $dO_2$ sensors in direct contact with the reactor contents. Calibration and standardization procedures for these sensors can be readily performed during operation of the bioreactor. In addition, outputs from these sensors can be compatible with current controllers used by industry. The use of PID controllers to maintain pH, $dO_2$ concentration, and temperature can be used in such bioreactors. As a stirred tank bioreactor with standard sensors, these control strategies can be directly translatable to a single use bioreactor. Because it can be a stand-alone unit, the single use bioreactor may be controlled using whichever controller type that is preferred by a given facility.

A. The Stirred-Tank Reactor System

In some embodiments, the stirred-tank reactor system of the present invention provides a flexible and disposable bag for a variety of purposes, including culturing cells, microorganisms, or plant metabolites as well as processing foods, chemicals, biopharmaceuticals and biologicals. The disposable bag may include disposable elements such as a shaft, impeller and bearing and is designed to fit into a permanent housing such as a reactor housing. The bag may further include one or more openings, pouches, ports or the like. The stirred-tank reactor system allows a user to operate the culture or production with relative ease and little training. In particular, the disposable system may not require cleaning or sterilizing. Furthermore, the system may not need continuous validation between production runs. Thus, it combines a flexible, easy-to-use, true stirred-tank reactor environment with little or no cross-contamination during the production process.

Referring to the drawings, FIG. 1 depicts a flexible bag 104 with at least one opening and an agitation shaft 112 with an attachable impeller 113. As shown, the agitation shaft 112 and attached impeller 113 are situated within the bag 104. Further, the agitation shaft 112 is connectable to a bearing 105, wherein the bearing 105 can be sealed to the bag by heat welding to the bag and/or through seal(s) or O-ring(s) 106. The bag 104, agitation shaft 112, impeller 113, and bearing 105, including seals or O-rings 106 are optionally disposable. The disposable bag can be a flexible, plastic bag. The bag 104 can be affixed to the agitation shaft 112 and the bearing 105 through at least one seal or O-ring 106 such that the inside of the bag remains sterile. The seals or o-rings can be further affixed to the bag as is shown in FIG. 1. Additionally, the disposable stirred-tank reactor system may be connected to a support or one or more bracket(s) 103 that hold the bearing 105 and motor 101. In one embodiment (as shown in FIG. 1), the support 103 is a motor and bearing support 103, wherein the upper end of the agitation shaft 112 is further connected to a motor coupling 102. The motor coupling 102 is connected to the motor 101 which drives the stirring motion of the agitation shaft 112 and impeller 113 leading to a hydrodynamic environment within the bag 104. The bag 104 is designed to fit into a housing 111 such as a barrel or chamber. The housing may be a metal barrel, a plastic barrel, a wood barrel, a glass barrel, or any other barrel or chamber made from a solid material. In one embodiment of the instant invention, the housing further includes a plurality of baffles, wherein the bag folds around the baffles. In another embodiment, the flexible bag 104 further includes a top port (single or multiple) 108, a bottom port (single or multiple) 109, and a side port (single or multiple) 110, wherein flexible tubing 107 can be connected to one or more of these ports.

The stirred-tank reactor system may optionally include a heater such as a heating pad, a steam jacket, or a circulating fluid or water heater. In one embodiment, the heater is located between the bag 104 and the housing 111. In another embodiment, the heater is incorporated into the housing 111 (e.g., into a double wall between the reactor housing and the bag). In yet another embodiment, the stirred-tank reactor system is placed inside an incubator. The heater allows for heating or warming of a specific culture or production. This is particularly important for cell cultures which are often grown at 37° C.

In one embodiment of the instant invention, the bag 104, the bearing 105, the seal(s) or O-ring(s) 106, the tubing 107, the top port(s) 108, the bottom port(s) 109, the side port(s) 110, the shaft 112, and the impeller 113 are disposable. The motor 101, the motor coupling 102, the bracket(s) or motor and bearing support 103, and the housing 111 are permanent.

B. Devices and Ports

The stirred-tank reactor system may also include sensors and other devices. In one embodiment, the bag includes a pH sensor and a dissolved-oxygen sensor, wherein the sensors are incorporated into the bag. As such, the sensors are disposable with the bag. In another embodiment, the sensors are attachable to the bag and are separate units. Such sensors may optionally be reusable after sterilization. In another embodiment, the system includes a product loop with flow past a pH sensor and dissolved-oxygen sensor, wherein the sensors are incorporated into the reactor housing. The system is flexible and provides alternative ways of supplying optional equipment of various kinds (e.g., sensors, probes, devices, pouches, ports, etc.). The system may also include one or more internal pouches that are sealed to the bag. In one preferred embodiment, the pouch has at least one end that can be opened to the outside of the bag to insert a probe into the reactor (i.e., the bag) while remaining on the exterior of the bag. The probe may be, for example, a temperature probe, a pH probe, a dissolved gas sensor, an oxygen sensor, a carbon dioxide sensor, a cell mass sensor, a nutrient sensor, an osmometer or any other probe that allows for testing or checking the culture or production. In another preferred embodiment, the system includes at least one port in the bag allowing for the connection of a device to the port. Such a device includes, but is not limited to, a tube, a filter, a connector, a probe, and a sampler. The incorporation of various ports into the bag allows for gas flow in and out of the bag as well as liquid flow in and out of the bag. Such ports also allow for sampling or testing the media or culture inside the bag. Tubing, filters, connectors, probes, samplers or other devices can be connected to the ports by using any desirable tubing connection technology. Pouches and ports that are sealed or affixed to the bag are disposable with the bag. The bag may also include a sparger (i.e., the component of a reactor that sprays air into the medium) sealed to the bag which can be disposed off with the bag.

Particularly, ports may be incorporated at any place on the flexible bag to accommodate the following:
Headspace gas in
Headspace gas out
Sparge gas in
Temperature probe
pH probe
Dissolved oxygen probe
Other desired probes
Sample apparatus
Media in
Titrant in
Inoculum in
Nutrient feeds in
Harvest out Each port may have flexible tubing attached to the port, to which media bags, sample devices, filters, gas lines, or harvest pumps may be attached with sterile or aseptic connections. In one embodiment, the ports are sealed onto the flexible bag during bag manufacture, and are sterilized with the bag assembly.

Devices that may be used to make aseptic connections to the flexible tubing are the following:
WAVE sterile tube fuser
TERUMO sterile tubing welder
PALL KLEENPAK® connector
Connection made under a laminar flow hood, using aseptic techniques
BAXTER Hayward proprietary "HEAT-TO-HEAT" connection using metal tubing and an induction heater In another embodiment, flexible tubing that is attached to an appropriate stainless-steel valve assembly may be sterilized separately (e.g., via autoclave), and then used as a way to connect the disposable bioreactor to traditional reactors or process piping. The valve assembly is used to make a traditional steam-in-place (SIP) connection to a traditional reactor or other process, and the flexible tubing is used to make a sterile or aseptic connection to a port on the disposable reactor.

Figure 2:
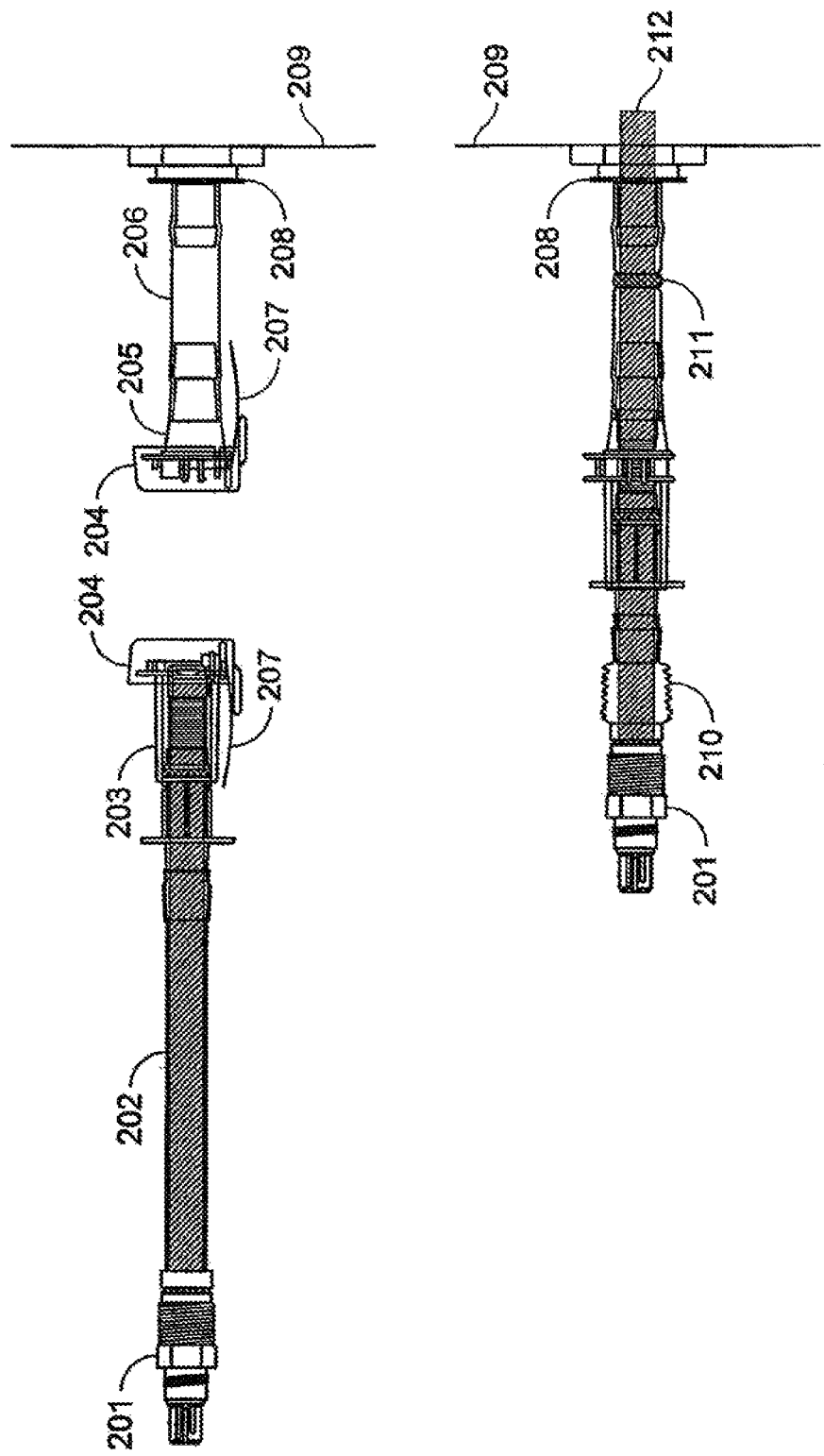
FIG. 2 depicts one embodiment of a probe connection in order to illustrate that a probe can be attached to the stirred-tank reactor system via a sterile or aseptic connection.

Referring to the drawings, FIG. 2 depicts a probe connection that can be employed with the stirred-tank reactor system according to one embodiment of the instant invention. As shown in FIG. 2, the probe 201 can be connected to a flexible sleeve 202 or bag which extends to one half of a PALL connector 203. The PALL connector 203 can be connected to the other half of the PALL connector 205 to provide for a sterile connection between the probe and the stirred-tank reactor system. The PALL connectors 203, 205 include covers 204 and filters 207 to keep the connection site sterile. Filters 207 can comprise a sealing layer or stripout layer. Sterile tubing 206 extends from the other half of the PALL connector 205 to a reactor port 208 of the reactor vessel 209 of the stirred-tank reactor system. In order to attach the probe, the PALL connection is made by removing the covers 204, mating the connectors 203, 205, removing the filters 207, and sliding the movable part of the connector into position. The probe sensor tip 212 is then pushed into the reactor as the flexible sleeve or bag bunches or compresses 210. The probe sensor tip 212 is then in direct contact with the inside of the reactor vessel 209. A clamp 211 is placed around the probe and tubing to seal the reactor contents from the PALL connection assembly. Thus, when a sterile connection is made between the two halves of the PALL connectors 203, 205, the flexible sleeve 202 or bag becomes compressed 210 and the probe is in contact with the culture or production media.

In one embodiment, the probes may be sterilized separately (e.g., via autoclave) then attached to the reactor via a sterile or aseptic connection. For example, a probe assembly may be made by inserting a probe 201 into one half of a PALL KLEENPAK® connector 203 and sealing the probe to the connector using a flexible sleeve or bag 202 as described above and shown in FIG. 2. The sleeve extends from the outside end of the probe to the barb of the PALL connector. This assembly is sterilized separately. The other half of the PALL connector 205 is connected to a port 208 on the reactor 209 via flexible tubing 206 that will accommodate the probe. This assembly is sterilized as part of the reactor. The PALL connector is described in detail in U.S. Pat. No. 6,655,655, the content of which is incorporated herein by reference in its entirety.

Figure 3A:
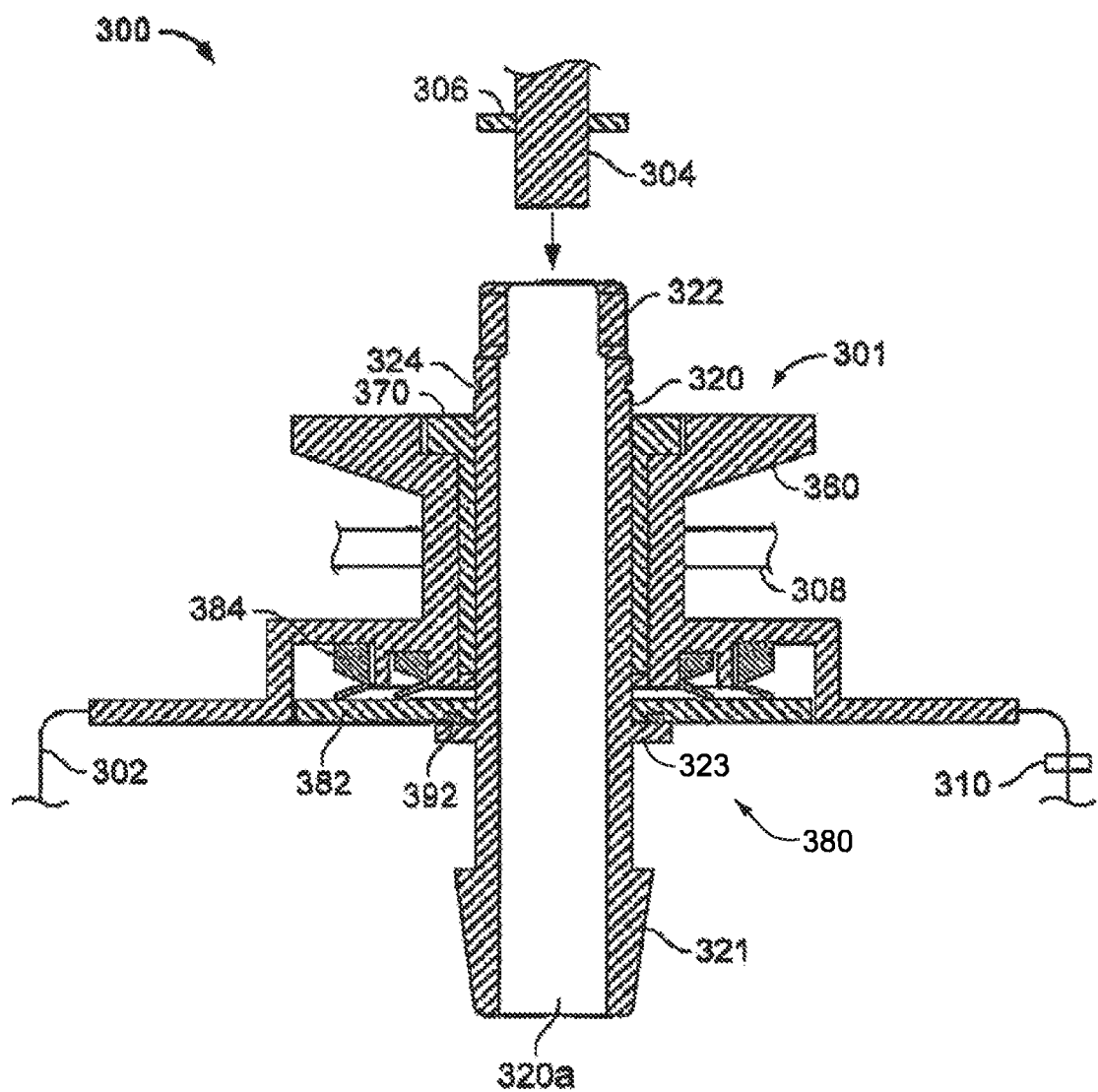
FIGS. 3A and 3B illustrate cross-section views of a reactor system according to one embodiment of the present invention.
Figure 3B:
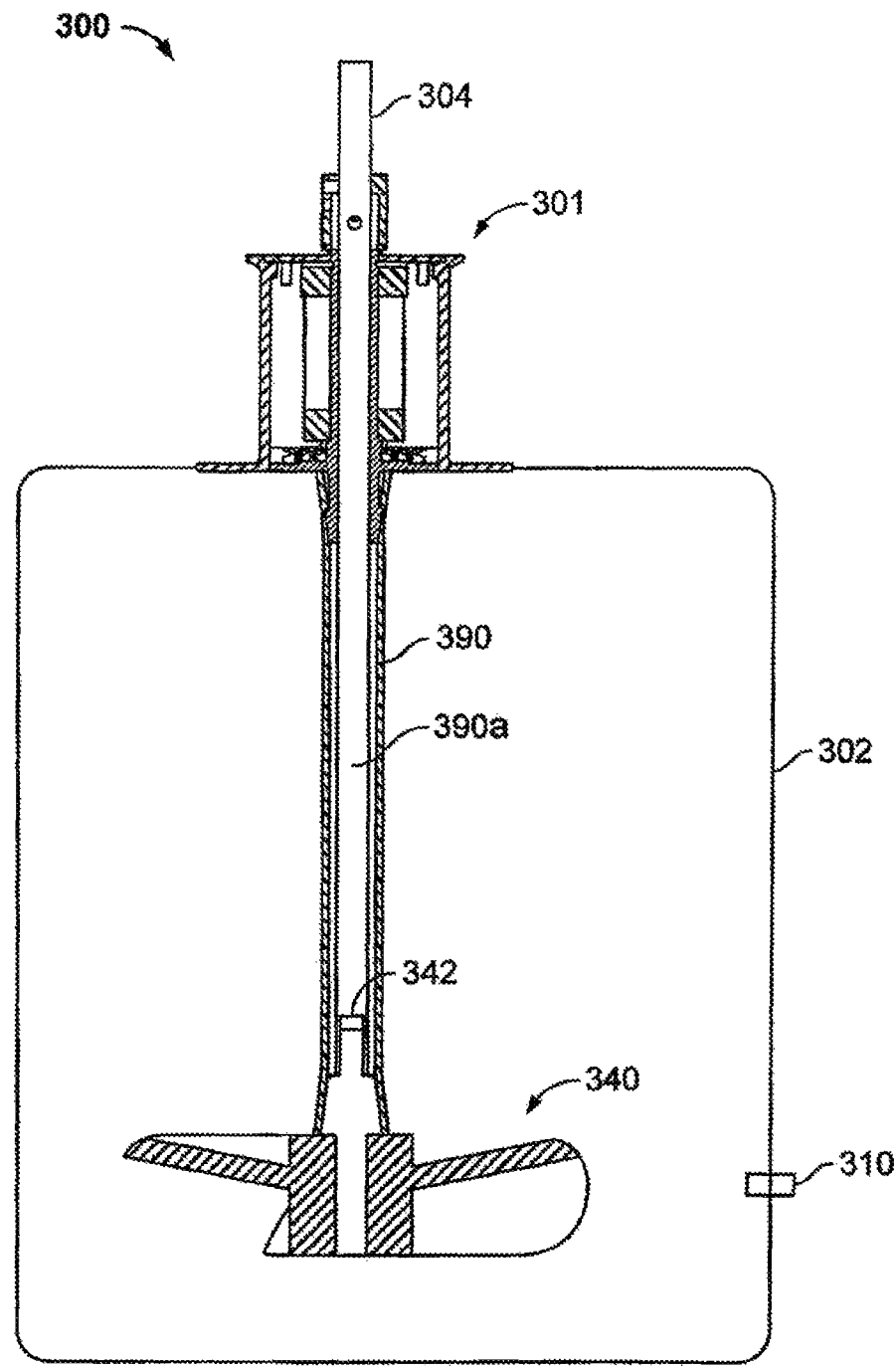

FIGS. 3A and 3B illustrate cross-section views of a reactor system 300 according to one embodiment of the present invention. Reactor system 300 can include a rotational assembly 301 coupled with a container 302. Optionally, reactor system 300 may include an impeller 340. In some embodiments, rotational assembly 301 is in sealed cooperation with an opening or aperture in container 302. Similarly, rotational assembly 301 may include a casing 360 that is coupled with the opening or aperture in container 302. Typically, impeller 340 is disposed within the interior of container 302. Rotational assembly 301 can be supported or held by bracket 308.

In some embodiments, rotational assembly 301 may include a hub 320 that is coupled with impeller 340, and hub 320 may be coupled with impeller 340 via a connector 390. Optionally, hub 320 may be directly coupled with impeller 340. In some embodiments, hub 320 is tubular in shape and includes an interior surface which bounds a passageway 320a longitudinally extending therethrough. In one embodiment an annular barb 321 radially encircles and outwardly projects from the exterior surface of hub 320. Barb 321 can be used for creating a sealed connection with connector 390.

Connector 390 can be tubular in shape, and can include an interior surface which bounds a passageway 390a extending longitudinally therethrough. In some embodiments, connector 390 includes a flexible tube having a first end connected in sealed engagement with hub 320 and an opposing second end connected in sealed engagement with impeller 340. Hub 320, either alone or in cooperation with connector 390, can provide a sealed channel in which drive shaft 304 can be received and removably coupled with impeller 340. Consequently, drive shaft 304 can be used repeatedly without sterilizing because it does not directly contact the contents of container 302. Furthermore, by using a flexible tube as connector 390, a flexible container 302 such as a bag assembly can be easily rolled up or folded for easy transport, storage, or processing.

Often, rotational assembly 301 will include a bearing assembly 370 disposed between hub 320 and casing 360. Bearing assembly 370 can include a journal bearing, which may be in fixed relation with casing 360, and hub 320 can rotate relative to the journal bearing and casing 360. Hub 320 may include a guide 324 for receiving a snap ring or retaining ring, which can help maintain hub 320 in place, relative to the journal bearing.

Rotational assembly 301 may also include a sealing arrangement 380, which can be disposed between hub 320 and casing 360. Sealing arrangement 380 can include, for example, a wear plate 382 and one or more seals 384, which may be, for example, dynamic seals. Wear plate 382 can be disposed circumferentially to, and coupled with, hub 320. Seal(s) 384 can be disposed between wear plate 382 and casing 360. Rotational assembly 301 may also include one or more seals 392 disposed between wear plate 382 and hub 320, wherein seals 392 may be, for example, static seals. In some embodiments, seal(s) 384 include one or more V-rings and seals(s) 392 include one or more O-rings. In the embodiments shown in FIG. 3A, seal(s) 384 include two V-rings, and seal(s) 392 include one O-ring. An annular flange 323 may also radially, outwardly project from the exterior surface of hub 320 and be disposed against seal 392.

In use, hub 320 is configured to receive or house a drive shaft 304 that is selectively coupled with a motor (not shown). In some embodiments, hub 320 may be configured to couple with one or more ears 306 located at an upper end of drive shaft 304 via one or more hub notches 322 formed on hub 320. Impeller 340 may include a spline 342 configured to couple with a lower end of drive shaft 304. Drive shaft 304 can be placed in hub 320, and coupled with hub 320 and impeller 340. For example, drive shaft 304 may extend through passageway 320a. Similarly, drive shaft 304 may extend through passageway 390a. Drive shaft 304 can be rotated by a motor, thereby rotating hub 320, connector 390, and impeller 340. In turn, impeller 340 agitates the contents of container 302. As hub 320 is rotated by drive shaft 304, seal(s) 392 provide a seal between wear plate 382 and hub 320 as they both rotate in unison, relative to casing 360. As casing 360 remains stationary, seal(s) 384 provide a seal between wear plate 382 and casing 360, where wear plate 382 rotates relative to casing 360. In some embodiments, seal(s) 384 provide a hermetic seal between wear plate 382 and casing 360. As shown here, seal(s) 384 can be in co-planar arrangement with one another.

In some embodiments, hub 320 may be removably engagable with drive shaft 304 such that annular rotation of drive shaft 304 facilitates annular rotation of hub 320. Although the embodiment depicted in FIG. 3A shows drive shaft ears 306 coupled with hub notches 322, the present invention contemplates any of a variety of coupling means for accomplishing this function. In yet other alternative embodiments, clamps, pins, collets, meshing teeth, or other fasteners can be used to removably secure drive shaft 304 to the hub 320 when the drive shaft 304 is coupled with hub 320. Similarly, the present invention contemplates any of a variety of coupling means for removably engaging drive shaft 304 to impeller 340, including the coupling means described above, such that rotation of drive shaft 304 facilitates rotation of impeller 340.

According to one embodiment of the present invention, reactor system 300 can be manufactured by coupling container 302 with rotational assembly 301, such that container 302 and rotational assembly 301 are in sealed cooperation with one another. For example, rotational assembly 301 can be coupled with an opening of container 302. Rotational assembly 301 can be manufactured to include hub 320, and hub 320 can be coupled with impeller 340 such that impeller 340 is disposed within container 302. Further, reactor system can be sterilized, for example by gamma radiation.

According to another embodiment of the present invention, reactor system 300 can be prepared for use by coupling casing 360 of rotational assembly 301 to frame bracket 308, and placing container 302 at least partially within a frame or container housing (not shown). Drive shaft 304 can be inserted into hub 320, and a distal end of drive shaft 304 can be coupled with impeller 340. Further, reaction components such as cells and culture media can be introduced into container 302 via a port 310.

Container 302 can include any of a variety of materials. In some embodiments, container 302 includes a flexible bag of water impermeable material such as a low-density polyethylene or other polymeric sheets having a thickness in a range between about 0.1 mm to about 5 mm, or between about 0.2 mm to about 2 mm. Other thicknesses can also be used. The material can be comprised of a single ply material or can comprise two or more layers which are either sealed together or separated to form a double wall container. Where the layers are sealed together, the material can comprise a laminated or extruded material. The laminated material can include two or more separately formed layers that are subsequently secured together by an adhesive. The extruded material can include a single integral sheet having two or more layers of different material that are each separated by a contact layer. All of the layers can be simultaneously co-extruded. One example of an extruded material that can be used in the present invention is the HyQ CX3-9 film available from HyClone Laboratories, Inc. out of Logan, Utah. The HyQ CX3-9 film is a three-layer, 9 mil cast film produced in a cGMP facility. The outer layer is a polyester elastomer coextruded with an ultra-low density polyethylene product contact layer. Another example of an extruded material that can be used in the present invention is the HyQ CX5-14 cast film also available from HyClone Laboratories, Inc. The HyQ CX5-14 cast film comprises a polyester elastomer outer layer, an ultra-low density polyethylene contact layer, and an EVOH barrier layer disposed therebetween. In another example, a multi-web film produced from three independent webs of blown film can be used. The two inner webs are each a 4 mil monolayer polyethylene film (which is referred to by HyClone as the HyQ BM1 film) while the outer barrier web is a 5.5 mil thick 6-layer coextrusion film (which is referred to by HyClone as the HyQ BX6 film).

Figure 4A:
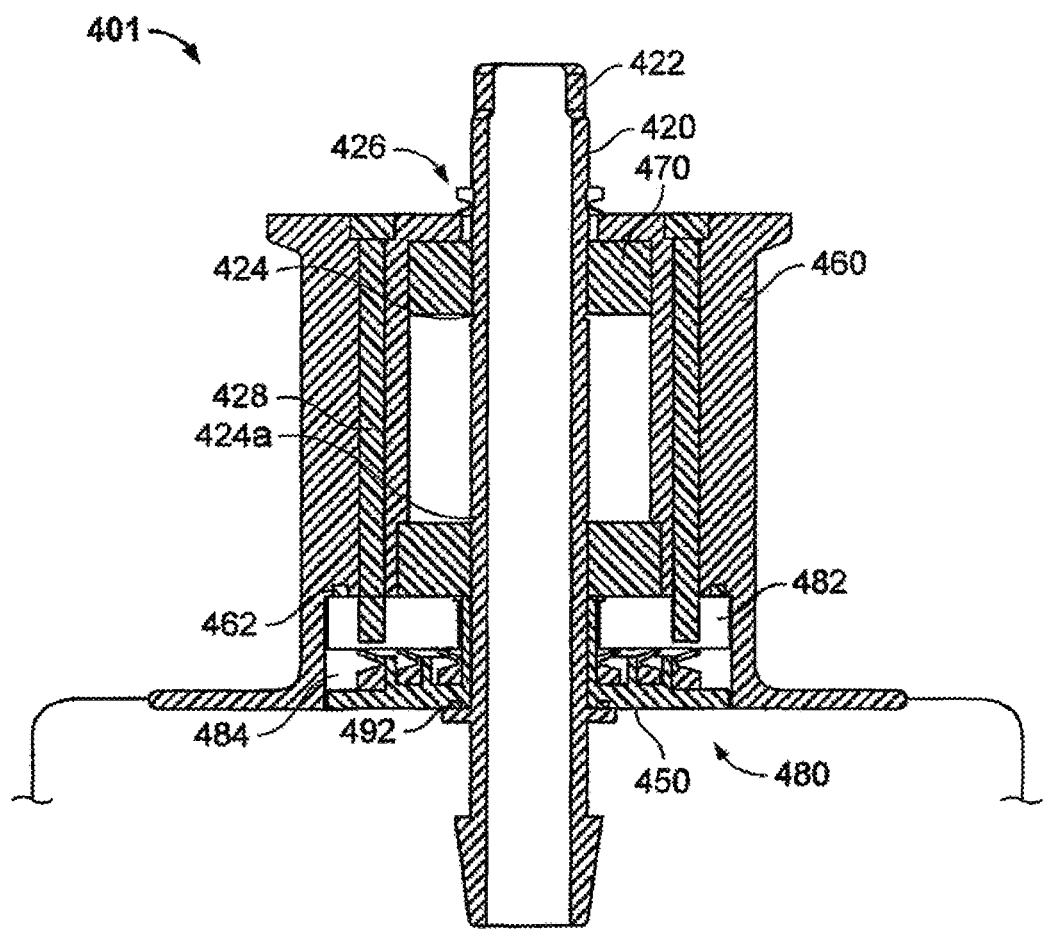
FIG. 4A illustrates a cross-section view of a rotational assembly according to one embodiment of the present invention.
Figure 4B:
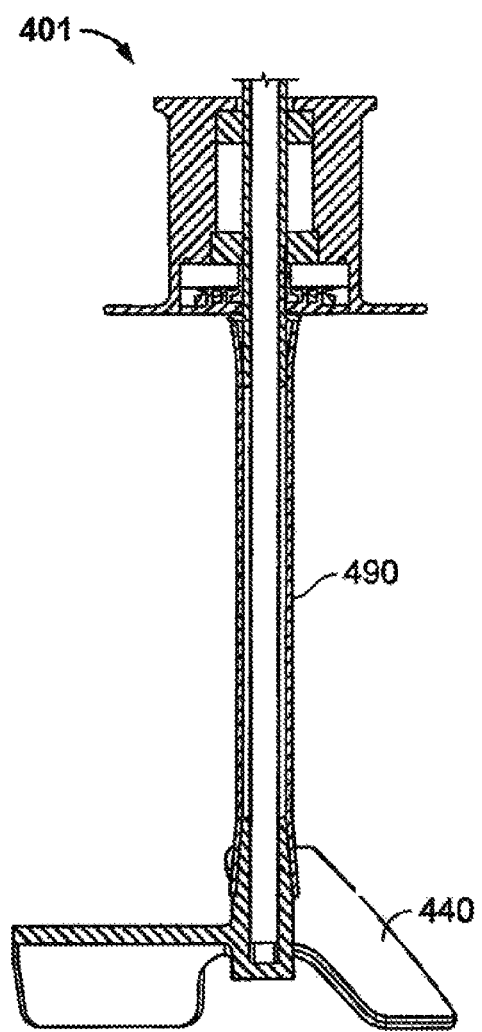
FIG. 4B illustrates a cross-section view of a rotational assembly according to one embodiment of the present invention.

FIG. 4A illustrates a cross-section view of a rotational assembly 401 according to one embodiment of the present invention. FIG. 4B illustrates a cross-section view of the rotational assembly 401 depicted in FIG. 4A coupled with a connector 490 and an impeller 440. Rotational assembly 401 may include a bearing assembly 470 disposed between a hub 420 and a casing 460. As shown here, bearing assembly 470 includes two race bearings, which are in fixed relation with casing 460. Hub 420 can rotate relative to the race bearings. Hub 420 may include guides 424, 424a for receiving a snap ring or retaining ring, which can help maintain hub 420 in place, relative to race bearings.

Rotational assembly 401 may also include a sealing arrangement 480, which can be disposed between hub 420 and casing 460. Sealing arrangement 480 can include, for example, a wear plate 482, one or more seals 484, and a rotating disk 450. Rotating disk 450 can be disposed circumferentially to, and coupled with, hub 420. Seal(s) 484 can be disposed between rotating disk 450 and wear plate 482. Wear plate 482 can be coupled with casing 460 via screws or bolts inserted through casing columns 428. Rotational assembly 401 may also include one or more seals 492 disposed between rotating disk 450 and hub 420. In some embodiments, seal(s) 484 include one or more V-rings and seals(s) 492 include one or more O-rings. In the embodiment shown in FIGS. 4A and 4B, seal(s) 484 include three V-rings, and seal(s) 492 include one O-ring. Rotational assembly 401 may also include one or more seals 426 to provide a seal between hub 420 and the top of casing 460, and one or more seals 462 to provide a seal between casing 460 and wear plate 482. As shown here, seal(s) 426 include one V-ring and seal(s) 462 include one O-ring.

In use, hub 420 is configured to receive or house a drive shaft (not shown). In some embodiments, hub 420 may be configured to couple with an ear of drive shaft via hub notch 422. As hub 420 is rotated by drive shaft, seal(s) 492 provide a seal between rotating disk 450 and hub 420 as they both rotate in unison, relative to casing 460. As casing 460 remains stationary, seal(s) 484 provide a seal between rotating disk 450 and wear plate 482, where rotating disk 450 rotates relative to wear plate 482 and casing 460. In some embodiments, seal(s) 484 provide a hermetic seal between rotating disk 450 and wear plate 482. As shown here, seal(s) 484 can be in co-planar arrangement with one another.

Figure 5:
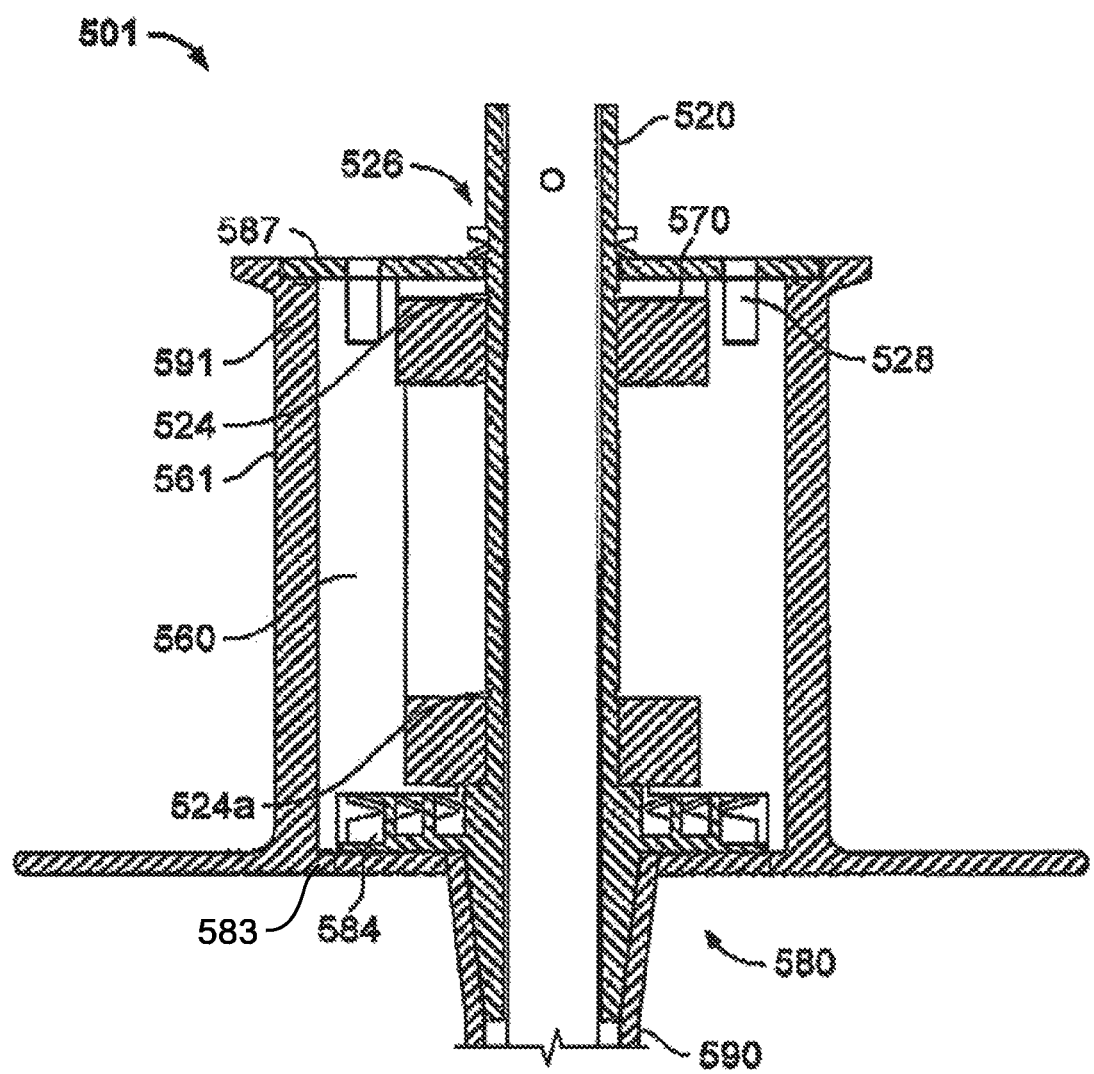
FIG. 5 illustrates a cross-section view of a rotational assembly according to one embodiment of the present invention.

FIG. 5 illustrates a cross-section view of a rotational assembly 501 according to one embodiment of the present invention. Rotational assembly 501 may include a bearing assembly 570 disposed between a hub 520 and an inner casing 560. As shown here, bearing assembly 570 includes two race bearings, which are in fixed relation with inner casing 560. Hub 520 can rotate relative to the race bearings. Hub 520 may include guides 524, 524a for receiving snap rings or retaining rings, which can help maintain hub 520 in place, relative to race bearings.

Rotational assembly 501 may also include a sealing arrangement 580. Sealing arrangement 580 can include, for example, a bottom plate 583 and one or more seals 584. Seal(s) 584 can be disposed between hub 520 and inner casing 560. A top plate 587 can be coupled with inner casing 560 via screws or bolts inserted through casing columns 528. Rotational assembly 501 may also include one or more seals 591 disposed between top plate 587 and an outer casing 561. In some embodiments, seal(s) 584 include one or more V-rings and seals(s) 591 include one or more O-rings. In the embodiment shown in FIG. 5, seal(s) 584 include three V-rings, and seal(s) 591 include one O-ring. Rotational assembly 501 may also include one or more seals 526 to provide a seal between hub 520 and the top plate 587. As shown here, seal(s) 526 include one V-ring.

In use, hub 520 is configured to receive or house, and couple with, a drive shaft (not shown). As hub 520 is rotated by drive shaft, seal(s) 584 provide a seal between hub 520 and inner casing 560 as hub 520 rotates relative to inner casing 560. In some embodiments, seal(s) 584 provide a hermetic seal between hub 520 and inner casing 560. As shown here, seal(s) 584 can be in co-planar arrangement with one another.

Figure 6:
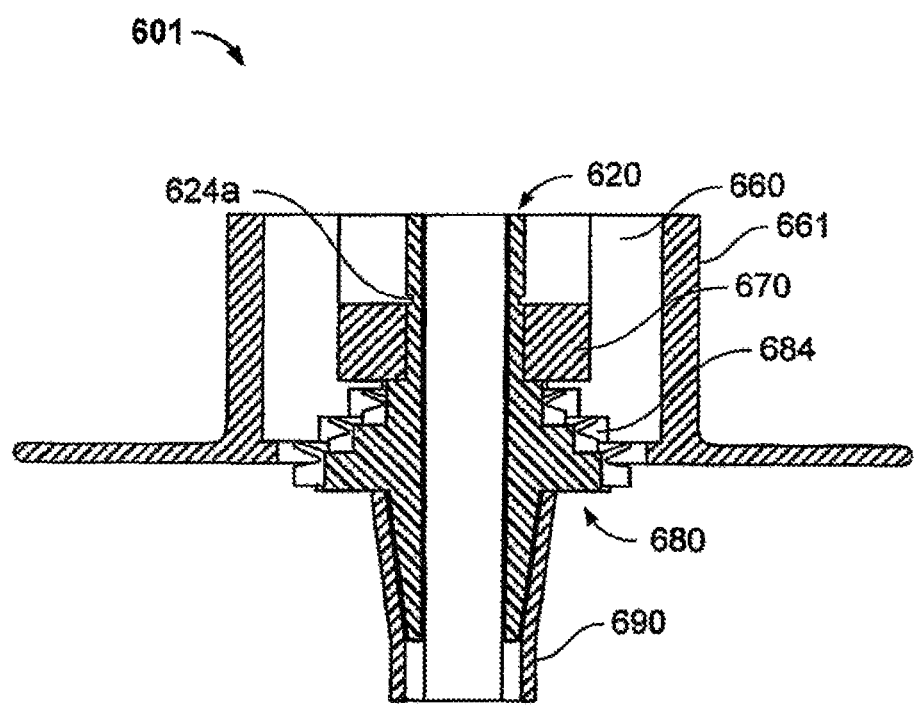
FIG. 6 illustrates a partial cross-section view of a rotational assembly according to one embodiment of the present invention.

FIG. 6 illustrates a partial cross-section view of a rotational assembly 601 according to one embodiment of the present invention. Rotational assembly 601 may include a bearing assembly 670 disposed between a hub 620 and an inner casing 660. As shown here, a lower race bearing of the bearing assembly 670 is in fixed relation with inner casing 660. Hub 620 can rotate relative to the race bearing. Hub 620 may include a guide 624a for receiving snap rings or retaining rings, which can help maintain hub 620 in place, relative to race bearing.

Rotational assembly 601 may also include a sealing arrangement 680. Sealing arrangement 680 can include, for example, one or more seals 684. Seal(s) 684 can be disposed between hub 620 and inner casing 660. In some embodiments, seal(s) 684 include one or more V-rings. In the embodiment shown in FIG. 6, seal(s) 684 include three V-rings.

In use, hub 620 is configured to receive or house, and couple with, a drive shaft (not shown). As hub 620 is rotated by drive shaft, seal(s) 684 provide a seal between hub 620 and inner casing 660, as hub 620 rotates relative to inner casing 660. In some embodiments, seal(s) 684 provide a hermetic seal between hub 620 and inner casing 660. As shown here, seal(s) 684 can be in a tiered-planar arrangement with one another.

Figure 7:
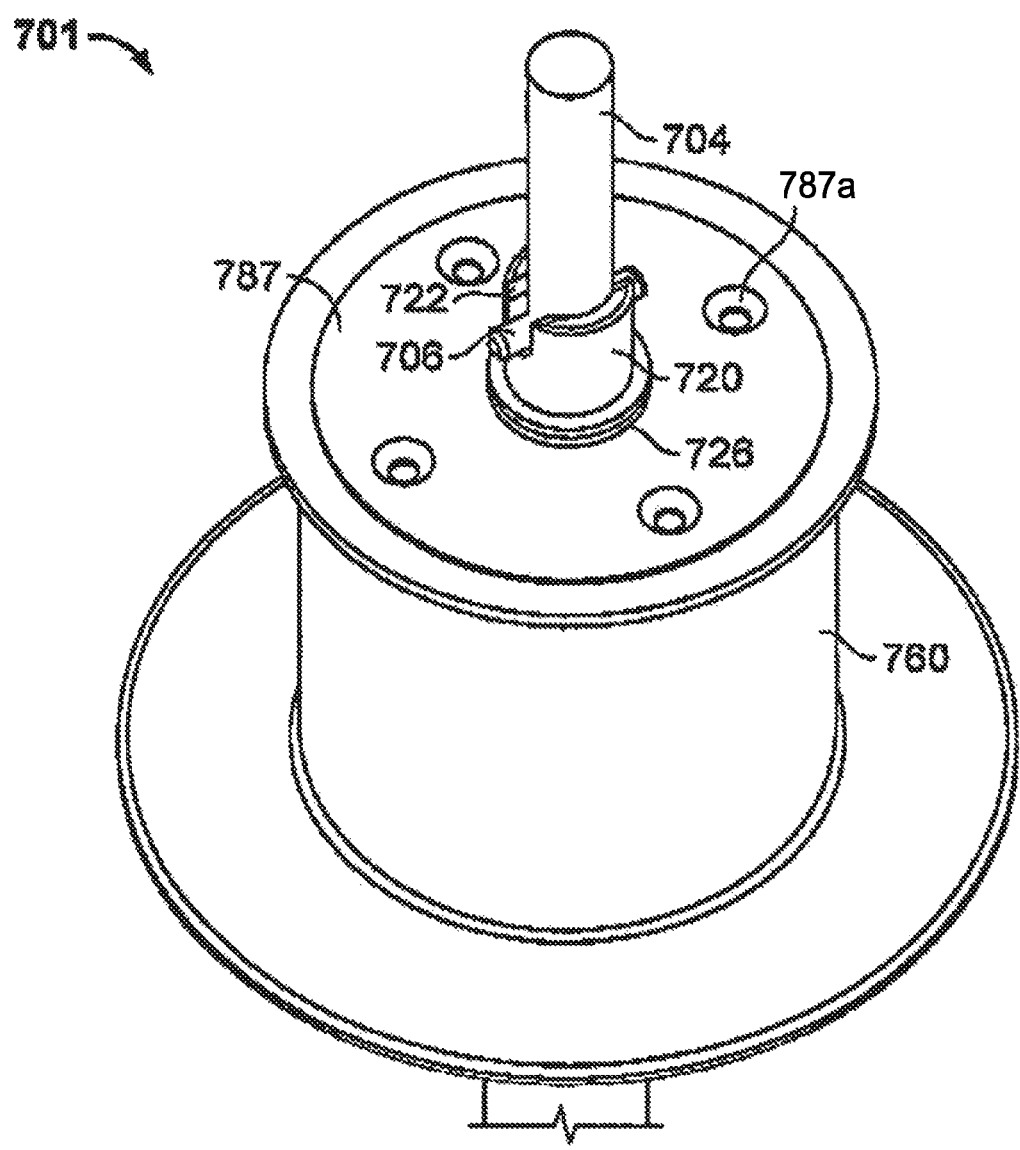
FIG. 7 illustrates a perspective view of a rotational assembly according to one embodiment of the present invention.

FIG. 7 illustrates a perspective view of a rotational assembly 701 according to one embodiment of the present invention. Rotational assembly 701 can include a hub 720 having one or more hub notches 722. In use, hub 720 is configured to receive or house, and couple with, a drive shaft 704. Hub notch(es) 722 are configured to couple with one or more drive shaft ears 706. A top plate 787 can be coupled with casing 760 via screws or bolts inserted through top plate apertures 787a. As hub 720 is rotated by drive shaft 704, hub 720 rotates relative to top plate 787 and casing 760. Rotational assembly 701 may also include one or more seals 726 to provide a seal between hub 720 and the top plate 787. As shown here, seal(s) 726 include one V-ring.

Figure 8:
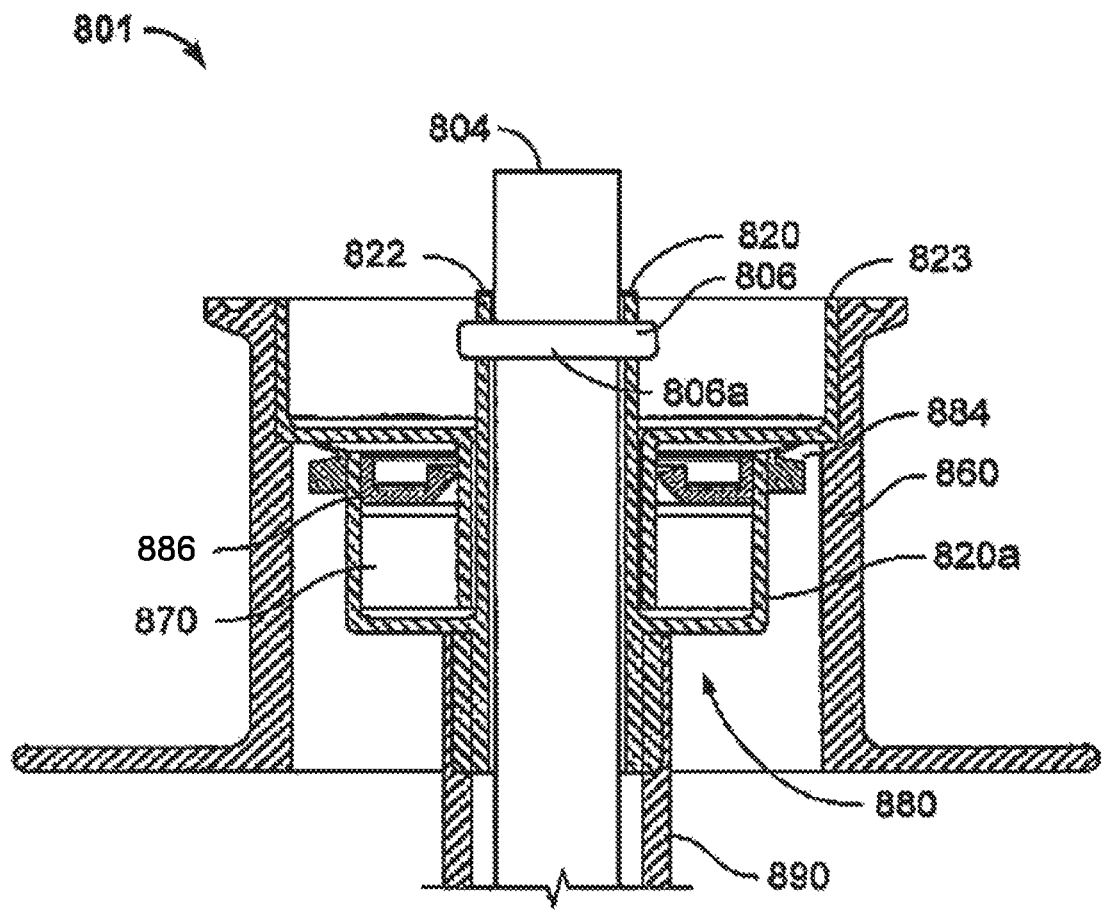
FIG. 8 illustrates a cross-section view of a rotational assembly according to one embodiment of the present invention.

FIG. 8 illustrates a cross-section view of a rotational assembly 801 according to one embodiment of the present invention. Rotational assembly 801 can include a hub 820 having one or more hub notches 822. As shown here, a bearing assembly 870 is in fixed relation with a housing 823. In use, hub 820 is configured to receive or house, and couple with, a drive shaft 804. Hub notch(es) 822 are configured to couple with one or more drive shaft ears 806, which may be at opposing ends of a drive shaft spindle 806a. As hub 820 is rotated by drive shaft 804, hub 820 rotates relative to housing 823, bearing assembly 870, and casing 860.

Rotational assembly 801 may also include a sealing arrangement 880, which can be disposed between hub 820 and housing 823. Sealing arrangement 880 can include, for example, one or more outer seals 884 and one or more inner seals 886. Seal(s) 884 can be disposed between an outer surface of hub cup 820a and housing 823, and seal(s) 886 can be disposed between an inner surface of hub cup 820a and housing 823. Housing 823 can be fixed with casing 860. In some embodiments, seal(s) 884 include one or more V-rings and seals(s) 886 include one or more oil seals. In the embodiment shown in FIG. 8, seal(s) 884 include one V-ring, and seal(s) 886 include one oil seal. Hub 820 can be coupled with a flexible tube 890.

Figure 9:
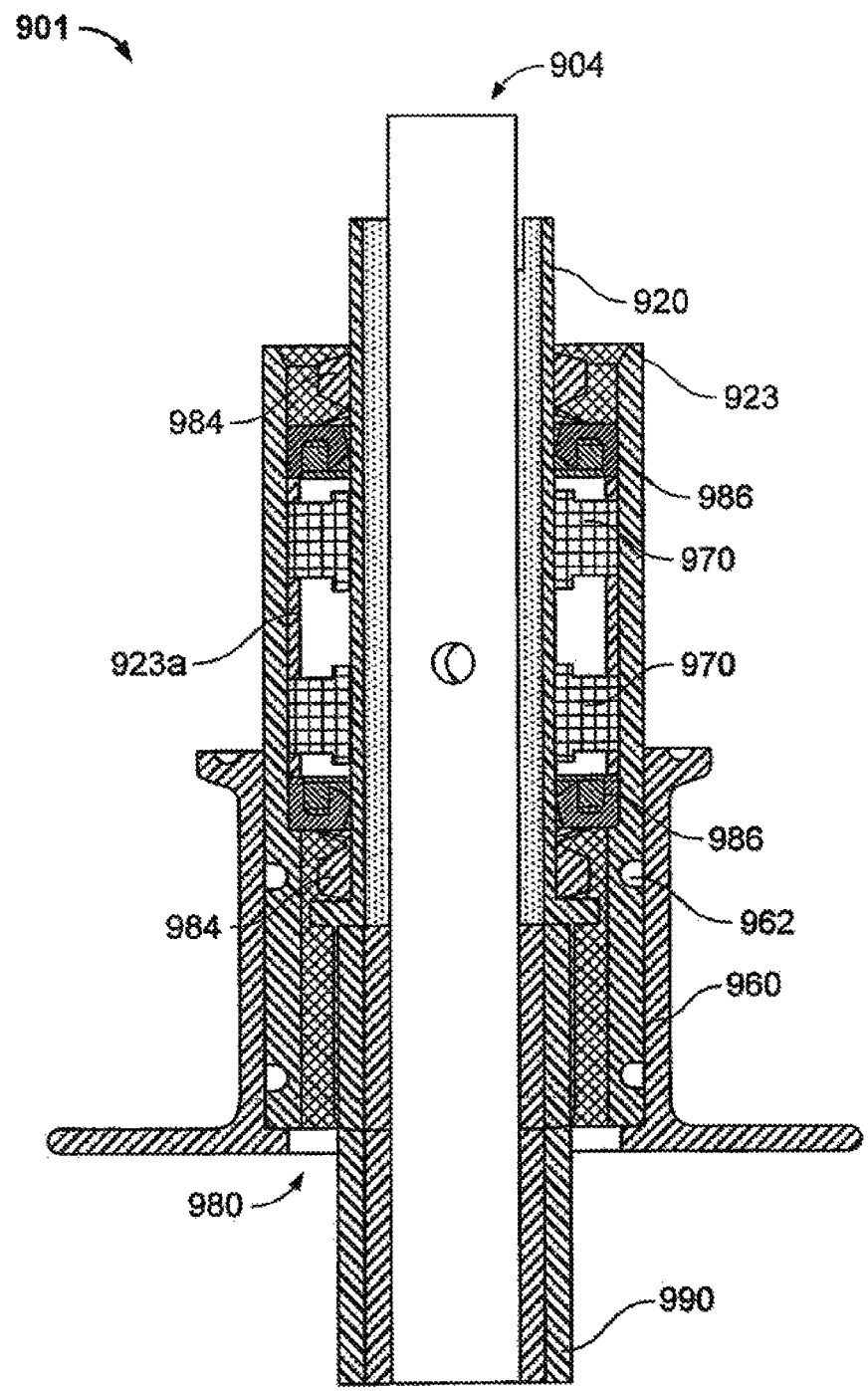
FIG. 9 illustrates a cross-section view of a rotational assembly according to one embodiment of the present invention.

FIG. 9 illustrates a cross-section view of a rotational assembly 901 according to one embodiment of the present invention. Rotational assembly 901 can include a hub 920 configured to releasably couple with a drive shaft 904. As shown here, two bearings of a bearing assembly 970 are in fixed relation with a housing 923. In use, hub 920 is configured to receive or house, and couple with, a drive shaft 904. As hub 920 is rotated by drive shaft 904, hub 920 rotates relative to housing 923, bearing assembly 970, and casing 960.

Rotational assembly 901 may also include a sealing arrangement 980, which can be disposed between hub 920 and inner housing 923a. Sealing arrangement 980 can include, for example, one or more outer seals 984 and one or more inner seals 986. Seal(s) 984 can be disposed between hub 920 and seal(s) 986, and seal(s) 986 can be disposed between seal(s) 984 and inner housing 923a. Housing 923 can be fixed with casing 960, and in sealed relation with casing 960 via one or more seal(s) 962. In some embodiments, seal(s) 984 include one or more V-rings, seals(s) 986 include one or more oil seals, and seal(s) 962 include one or more O-rings. In the embodiment shown in FIG. 9, seal(s) 984 include two V-rings, seal(s) 986 include two oil seals, and seal(s) 962 include two O-rings. Hub 920 can be coupled with a flexible tube 990.

Figure 10:
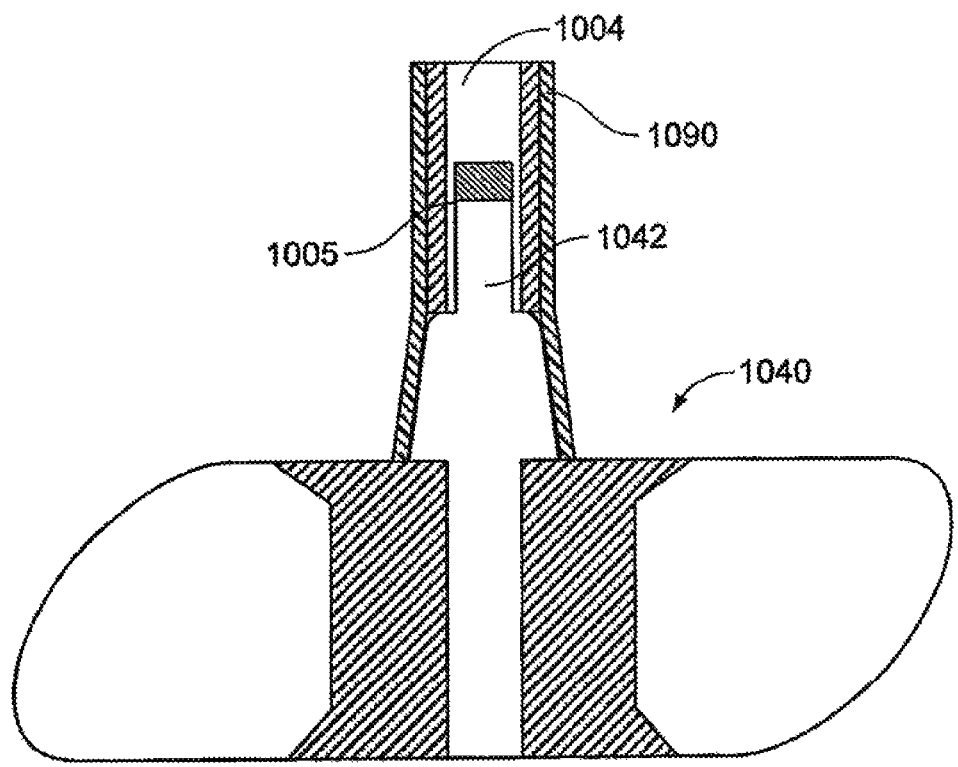
FIG. 10 illustrates a cross-section view of an impeller according to one embodiment of the present invention.

FIG. 10 illustrates a cross-section view of an impeller 1040 according to one embodiment of the present invention. Impeller 1040 can be coupled with connector 1090, which can be coupled with hub (not shown). Impeller 1040 can include an impeller spline 1042 which can couple with a spline 1005 of drive shaft 1004.

Figure 11:
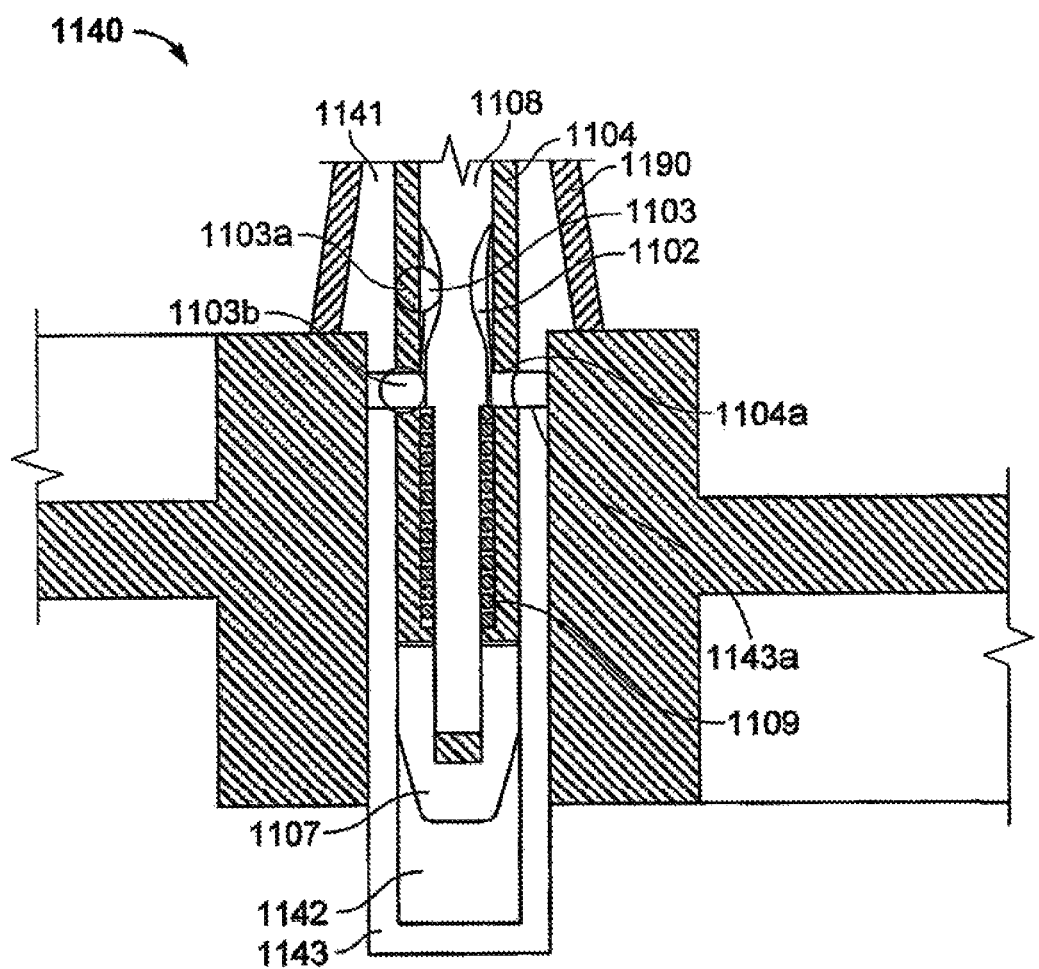
FIG. 11 illustrates a partial cross-section view of an impeller according to one embodiment of the present invention.

FIG. 11 illustrates a partial cross-section view of an impeller 1140 according to one embodiment of the present invention. Impeller 1140 can include an impeller barb fitting 1141 that can couple with a rotational assembly hub (not shown) via a connector 1190. Drive shaft 1104 can be attached to impeller 1140 by placing drive shaft 1104 into impeller aperture 1142. When drive shaft 1104 is inserted into impeller aperture 1142, end cap 1107 can reach the distal end of impeller base 1143. As shown here, drive shaft 1104 is hollow and adapted to receive a core 1108. Drive shaft 1104 is coupled with an end cap 1107. Core 1108 includes a ball dent 1102 which operatively associates with a ball 1103. In a first ball configuration 1103a, ball 1103 is disposed at ball dent 1102. As core 1108 is advanced along the inside of hollow drive shaft 1104 toward the distal end of impeller aperture 1142, spring 1109 is compressed, and ball 1103 moves into opening 1104a in drive shaft opening 1104a and impeller base opening 1143a, thus adopting a second ball configuration 1103b. Distal end of core 1108 can cause end cap 1107 to separate from drive shaft 1104. In some embodiments, core 1108 is in threaded engagement with end cap 1107, which can prevent spring 1109 from pushing core 1108 back out of hollow drive shaft 1104.

Figure 12:
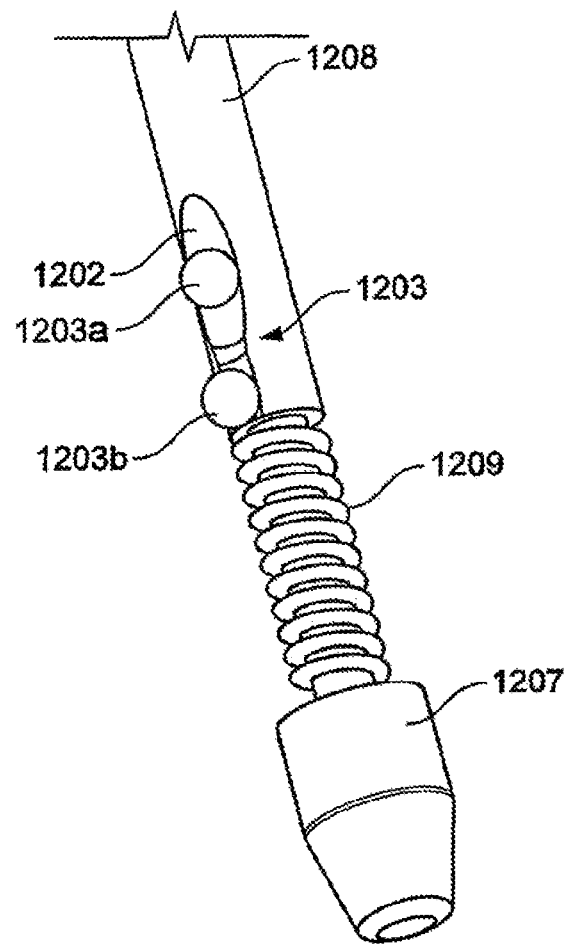
FIG. 12 illustrates a perspective view of drive shaft core according to one embodiment of the present invention.

FIG. 12 illustrates a perspective view of drive shaft core 1208 according to one embodiment of the present invention. Drive shaft core 1208 includes ball dent 1202, end cap 1207, spring 1209, and ball 1203. As shown here, ball 1203 can adopt a first ball configuration 1203a and a second ball configuration 1203b.

Figure 13:
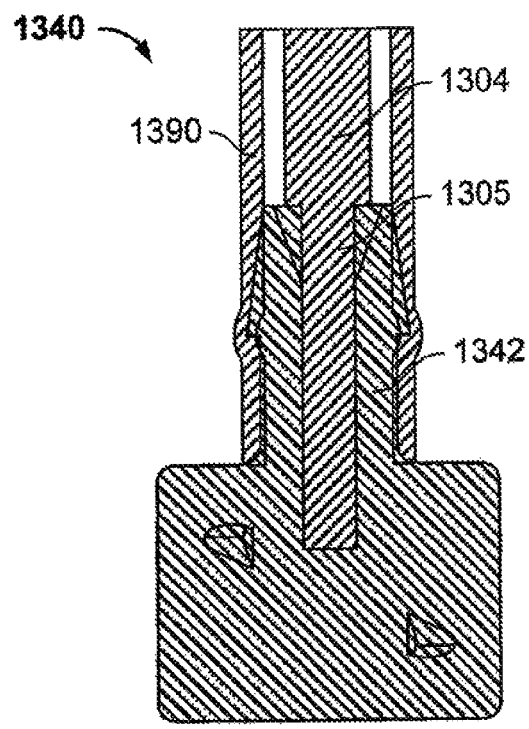
FIG. 13 illustrates a cross-section view of an impeller according to one embodiment of the present invention.

FIG. 13 illustrates a cross-section view of an impeller 1340 according to one embodiment of the present invention. Impeller 1340 can include a square spline 1342 for coupling with a square spline 1305 of drive shaft 1304. Impeller 1340 can be coupled with hub (not shown) via a connector 1390. For the sake of clarity, the impeller blades are not shown in this figure.

Figure 14A:
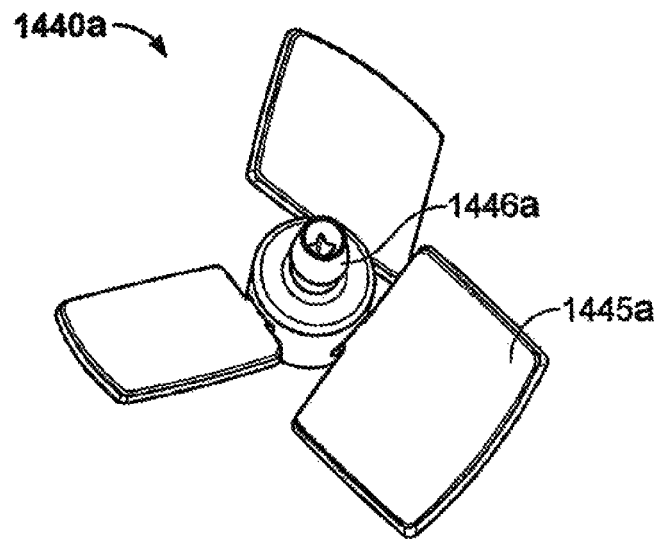
FIG. 14A illustrates a perspective view of an impeller according to one embodiment of the present invention.

FIG. 14A illustrates a perspective view of an impeller 1440a according to one embodiment of the present invention. Impeller 1440a can include one or more impeller blades 1445a coupled with an impeller body 1446a. In some embodiments, impeller blades 1445a can be machined separately from impeller body 1446a. Impeller blades 1445a may be constructed from a variety of materials, including Delrin, HDPE, and the like. Impeller body 1446a may be constructed from a variety of materials, including HDPE and the like.

FIG. 14B illustrates a perspective view of an impeller 1440b according to one embodiment of the present invention. Impeller 1440b can include one or more impeller blades 1445b and an impeller body 1446b. In some embodiments, impeller 1440b can be molded as a single piece. Impeller 1440b may be constructed from a variety of materials, including medium low density polyethylene, low density polyethylene, DOW ENGAGE® polyolefin elastomers, and the like.

FIG. 15 illustrates a cross-section view of a sparger body 1500 according to one embodiment of the present invention. Sparger body 1500 can include a sheet of permeable material. In some embodiments, sparger body 1500 includes a vapor-permeable and water-resistant material. In related embodiments, sparger body 1500 includes a high density polyethylene fiber. For example, sparger body 1500 can include TYVEK® material. Sparger body 1500 can be in fluid communication with a port of a container (not shown) via a sparger conduit 1510. As shown in FIG. 15, sparger body 1500 can be in the shape of a donut or ring. Relatedly, sparger body 1500 can include a base 1502 which is adapted to anchor to an interior surface of a container (not shown). The base may or may not include a gas permeable material. In other embodiments, one or more sheets of gas permeable material can be directly sealed with the interior of the container, whereby the interior of the sparger body 1500 includes a gas permeable material on one side (e.g. top side of body), and a corresponding portion of the container on the other side (e.g. bottom side of body).

In some embodiments, the permeability of the sparger body is such that fluid is prevented from flowing into the sparger when not in use. Similarly, the sparger may be constructed so as to only allow gas to pass through the permeable material when it is subject to sufficiently high gas pressure. Often, a sparger body will include a soft, flexible material. In some embodiments, sparger body 1500 may be welded directly onto the container so as to ensure proper placement and alignment. When coupled with a flexible container such as a flexible bag, sparger body 1500 can effectively be folded up with the bag for storage and transport, sterilized simultaneously with the bag, and disposed of so as to eliminate subsequent cleaning. Sparger body 1500 can provide for minute gas bubbles which can increase diffusion of gas into the fluid. It is appreciated that other types of spargers can be used with the present system.

A variety of materials or assemblies can be used to provide gas transfer into growth chambers. These include, for example, porous materials in the form of tubing made of TEFLON® (PTFE), polysulfone, polypropylene, silicone, KYNAR® (PVDF), and the like. In some embodiments, used to provide gas transfer into growth chambers. As noted above, sparger body 1500 can include TYVEK® material, which can be used in a bioreactor for the use of active gas diffusion. Similarly, this material can be used in a growth chamber utilizing passive gas transfer. Permeability of TYVEK® film can be measured using the quantitative property of Gurley Hill Porosity. In some embodiments, such materials range in values between about 6 to about 30 (sec/100 cc in$^2$). Permeability rated according to the methods of Bendtsen Air Permeability are often in a range between about 400 to about 2000 (ml/min).

In some embodiments, a permeable material will have high permeability while maintaining hydrophobicity, strength, weldability, biocompatibility, and gamma stability. Often, it is desirable to have a flexible material that welds readily to common materials used in the film or port configurations, often found in the manufacture of bioprocessing containers (BPCs). For example, the flexible nature of a soft or paper like film can allow it to be folded during manufacturing, packaging, loading, and use of the bioreactor. It may also be desirous to allow for the surface area and shape of the sparge material to easily be modified or changed according to weld or cut pattern. Optionally, instead of providing a sparger body to be immersed in the contents of a container, a permeable envelope could be used to encapsulate the liquid contents of the bioreactor, thus providing a broad area for diffusion.

Welding the sparger body on a port or container surface can provide for a high level of surface area while providing a low-profile sparge. In some embodiments, this can reduce turbulence near the impeller and/or reduce the possibility of cells accumulating in cracks, seams, or crevices. Often, conventional sparge configurations rely on the use of sparging rings that have small hole perforations that are placed below the impeller. Spargers can also include the use of extremely small pore sizes. Such porous materials are commonly seen as sintered metal or ceramic materials. Using a single use disposable material such as TYVEK® may be helpful in avoiding or reducing contamination and cleaning issues that may be associated with some conventional spargers, which sometimes involve cleaning numerous holes, pores, and crevices of such units. For example, small void areas in some spargers may present areas for cell debris to lodge and accumulate leading to increased occurrence of contamination. In some cases, this may carry over in subsequent cell runs.

One purpose of a sparge unit in a cell culture is to aid in the mass transfer of oxygen ($K_L a$), which is often necessary for the respiration of the growing cells. An advantage of a sparge approach used in a single use bioreactor is that the tortuous pore structure of a gas permeable membrane such as TYVEK® can allow for a beneficial effect on mass transfer of oxygen from the bulk gas introduced through the sparger. In some embodiments, it is desirable to have small bubbles introduced into the bioreactor as they can benefit mass transfer. Mass transfer across a permeable membrane can occur independent of mass transfer resulting from a gas bubble. Relatedly, a long gas retention time within the fluid column and higher surface to volume ratios are often desirable effects. It is generally accepted that the bubble size can be dominated by surface tension effects, inherently related to the component ratio of salts, proteins, sugars, and micro and macro components of the nutrient media. Experimentally calculated $K_L a$ values, visual observation, and data from bioreactor runs often indicate that bubble size and perhaps improved mass transfer are qualities of the present sparge approaches. The composition and rheological properties of the liquid, mixing intensity, turnover rate of the fluid, bubble size, presence of cell clumping, and interfacial absorption characteristics all influence mass transfer of gas such as oxygen to the cells. Main driving forces of mass transfer include surface area and concentration gradient. In many cases, a main source of resistance of oxygen mass transfer in a stirred tank bioreactor can be the liquid film surrounding the gas bubble.

A sparging material such as TYVEK® can provide for the transfer of gas across the membrane. Relatedly, by incorporating TYVEK® and similar gas permeable membranes, the surface area can easily be increased. In some embodiments, the oxygen gradient between the membrane and the liquid interface can be maintained at a high level through constant replenishment directly through a sparge inlet. Further, a rapid mixing intensity can also benefit mass transfer as the impeller pumps media directly down onto a sparger surface. The use of a membrane can allow for mass transfer of oxygen across the bulk film surface, which can be in addition to the formation of bubbles that rise within the fluid column. In many cases, small bubbles can lead to greater foaming at the top of a bioreactor, which can have negative effects on cell viability and $K_L a$ according to Henry's law and the solubility of gases related to partial pressures. This boundary layer often results in a reduced ability to control dissolved oxygen levels within the bulk liquid. Typically, it is desirable to avoid or mitigate the presence of foam, as excessive amounts can result in exhaust filter blocking and run failure. The novel sparger approaches described herein can provide the desired mass transfer properties, often with reduced levels of foam generated as compared to conventional systems. This may be due to greater efficacy and less gas being introduced through the sparger to maintain a target oxygen solubility.

TYVEK® is similar in some aspects to the material GORE-TEX® in that it has hydrophobic qualities but will still allow water vapor to pass through. For medical grades of TYVEK® a large relative pore size can be about 20 (micrometers) and the surface energy can be about 25 to about 32 (dynes/cm). As mentioned elsewhere herein, it may be beneficial to use a check valve in a gas inlet stream near a sparger to reduce undesirable transfer of water vapor through the membrane when the sparger is submerged while not in use. Actual moisture transmission rates may vary largely with the media used and the particular application. Moisture Vapor Transmission Rates (MTVR) often range from about 1500 to about 1640 (g/m$^2$/24 hrs). The present invention also contemplates the use of these sparger approaches in the form of a replaceable retrofit kit, which may be adapted for use with conventional bioreactors. Such kits can improve $K_L a$ and replace a piece of hardware commonly used in steam sterilized bioreactors that may be difficult to sterilize or clean.

It is appreciated that any of a variety of permeable membranes may be used as a sparging material. In some embodiments, such membranes may be comprised of high density polyethylene fibers that are heat sealed into a web having a thickness in a range between about 50 microns to about 250 microns. The fibers typically have a diameter in a range between about 2 microns to about 8 microns and can be produced by a flash spun process or other methods.

In other embodiments, the sparging material may include a perforated film sheet, such as a sheet of low density PE film with small perforated holes. This may be in the form of a plastic tubing, molded plastic, shaped film, or flat film. The small perforated holes can be, for example, punched, molded, or embossed into the film. As described above, such sparging materials or constructions can be fixed to the container. In some embodiments, a sparging mechanism may include a combination of a permeable membrane and a perforated film.

Figure 16:
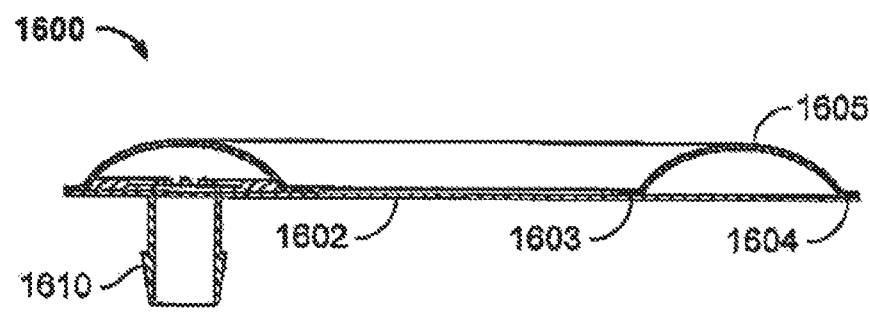
FIG. 16 illustrates a cross-section view of a sparger assembly according to one embodiment of the present invention.

FIG. 16 illustrates a cross-section view of a sparger assembly 1600 according to one embodiment of the present invention. Sparger assembly 1600 can include a sheet of permeable material 1605 and a sparger conduit 1610. As shown here, sheet of permeable material 1605 is annular in shape. Sparger assembly 1600 can be in fluid communication with a port of a container (now shown) via sparger conduit 1610. An inner ring 1603 and an outer ring 1604 of sheet 1605 can each be anchored to the interior surface of a container 1602, such that the sheet of permeable material 1605, as coupled with container 1602, defines a donut-shaped space.

Figure 17:
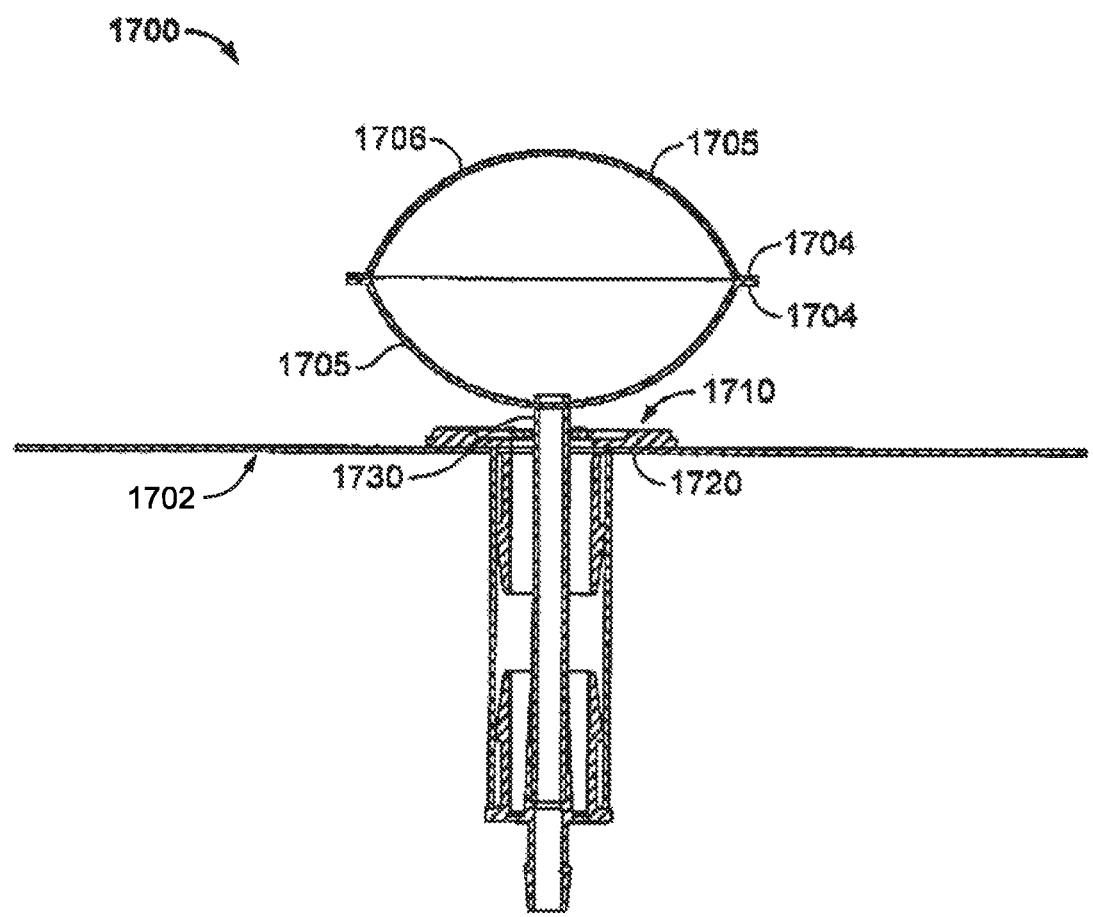
FIG. 17 illustrates a cross-section view of a sparger assembly according to one embodiment of the present invention.

FIG. 17 illustrates a cross-section view of a sparger assembly 1700 according to one embodiment of the present invention. Sparger assembly 1700 can include any number of sheets of permeable material 1705, a sparger tube 1730, and a sparger conduit 1710. Sparger assembly 1700 can be in fluid communication with a port 1720 of a container 1702 via a sparger conduit 1710. As shown here, sparger assembly 1700 can include a sparger body 1706 that is constructed of two sheets of permeable material 1705 which are coupled together along their outer rings 1704. It is appreciated that sparger body 1706 can be configured in any of a variety of shapes, including spheres, cylinders, boxes, pyramids, irregular shapes, and the like, and may include any combination of permeable and non-permeable materials or surfaces.

Figure 18:
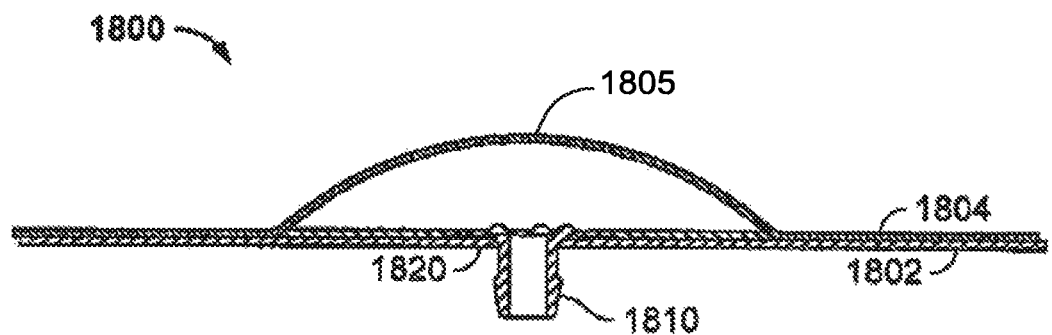
FIG. 18 illustrates a cross-section view of a sparger assembly according to one embodiment of the present invention.

FIG. 18 illustrates a cross-section view of a sparger assembly 1800 according to one embodiment of the present invention. Sparger assembly 1800 can include a sheet of permeable material 1805 and a sparger conduit 1810. Sparger assembly 1800 can be in fluid communication with a port 1820 of a container 1802 via sparger conduit 1810. As shown here, sheet of permeable material 1805 is circular in shape. An outer ring 1804 of sheet 1805 can each be anchored to the interior surface of a container 1802, such that the sheet of permeable material 1805, as coupled with container 1802, defines a dome-shaped space. Sparger assembly configurations such as those described herein can allow the surface area and corresponding gas flow rate requirements of, for example, the permeable material 1805 to be adjusted by utilizing different size shapes such as the dome shown here. Some embodiments of the present invention may include a check valve inline coupled with a tubing that is attached to the sparger conduit 1810, which can prevent fluid backflow.

Figure 19:
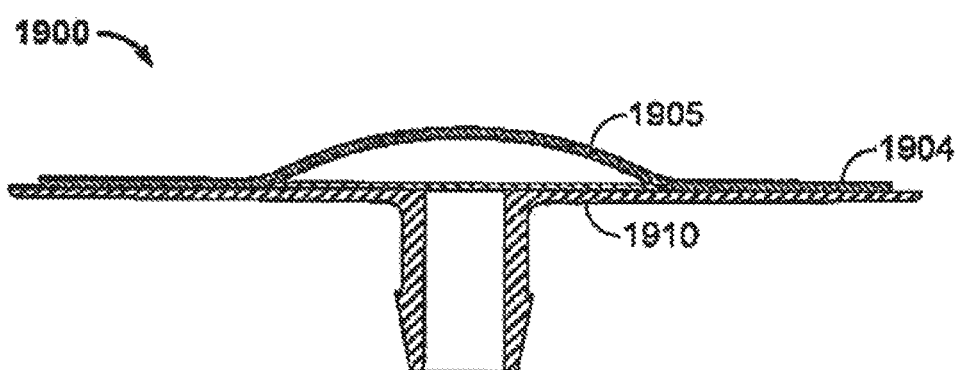
FIG. 19 illustrates a cross-section view of a sparger assembly according to one embodiment of the present invention.

FIG. 19 illustrates a cross-section view of a sparger assembly 1900 according to one embodiment of the present invention. Sparger assembly 1900 can include a sheet of permeable material 1905 and a sparger conduit 1910. Sparger assembly 1900 can be in fluid communication with a port of a container (not shown) via sparger conduit 1910. As shown here, sheet of permeable material 1905 is circular in shape. An outer ring 1904 of sheet 1905 can be coupled with sparger conduit 1910, such that the sheet of permeable material 1905, as coupled with sparger conduit 1910, defines a dome-shaped space.

Figure 20:
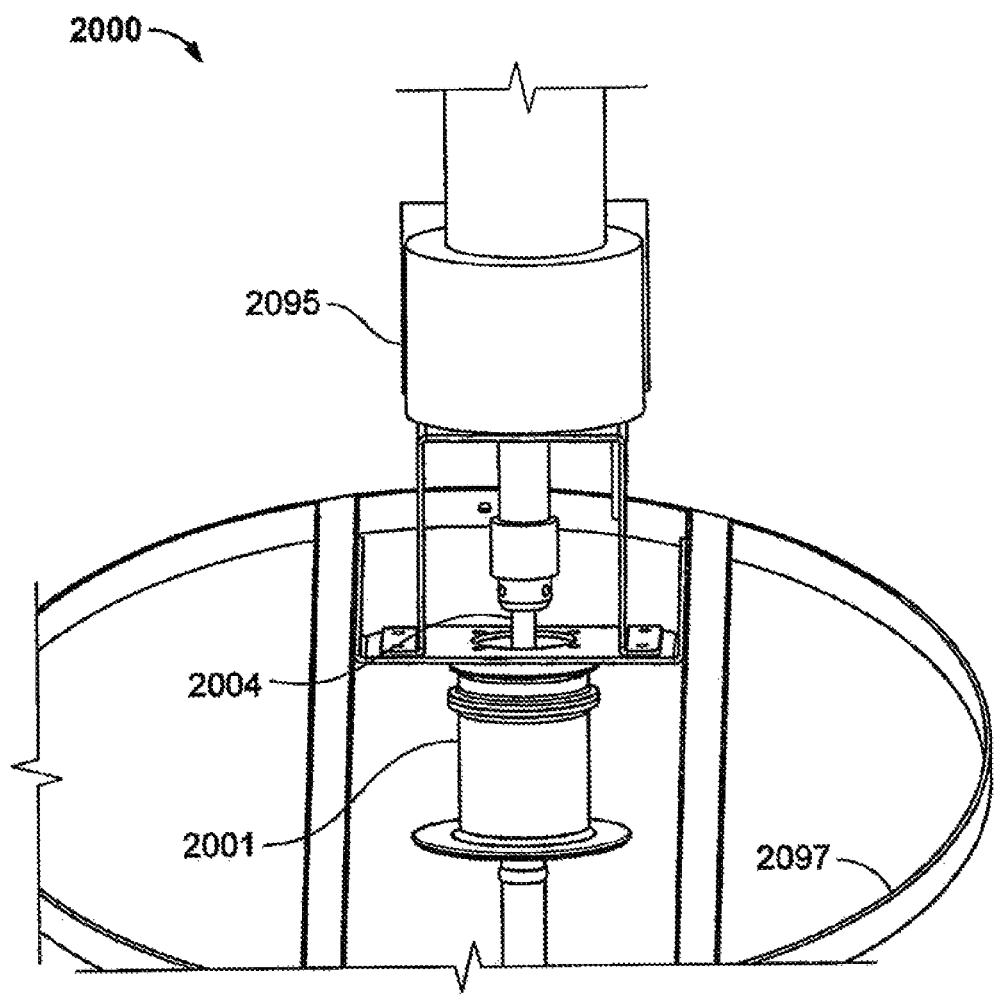
FIG. 20 illustrates a partial perspective view of a reactor system according to one embodiment of the present invention.
Figure 21:
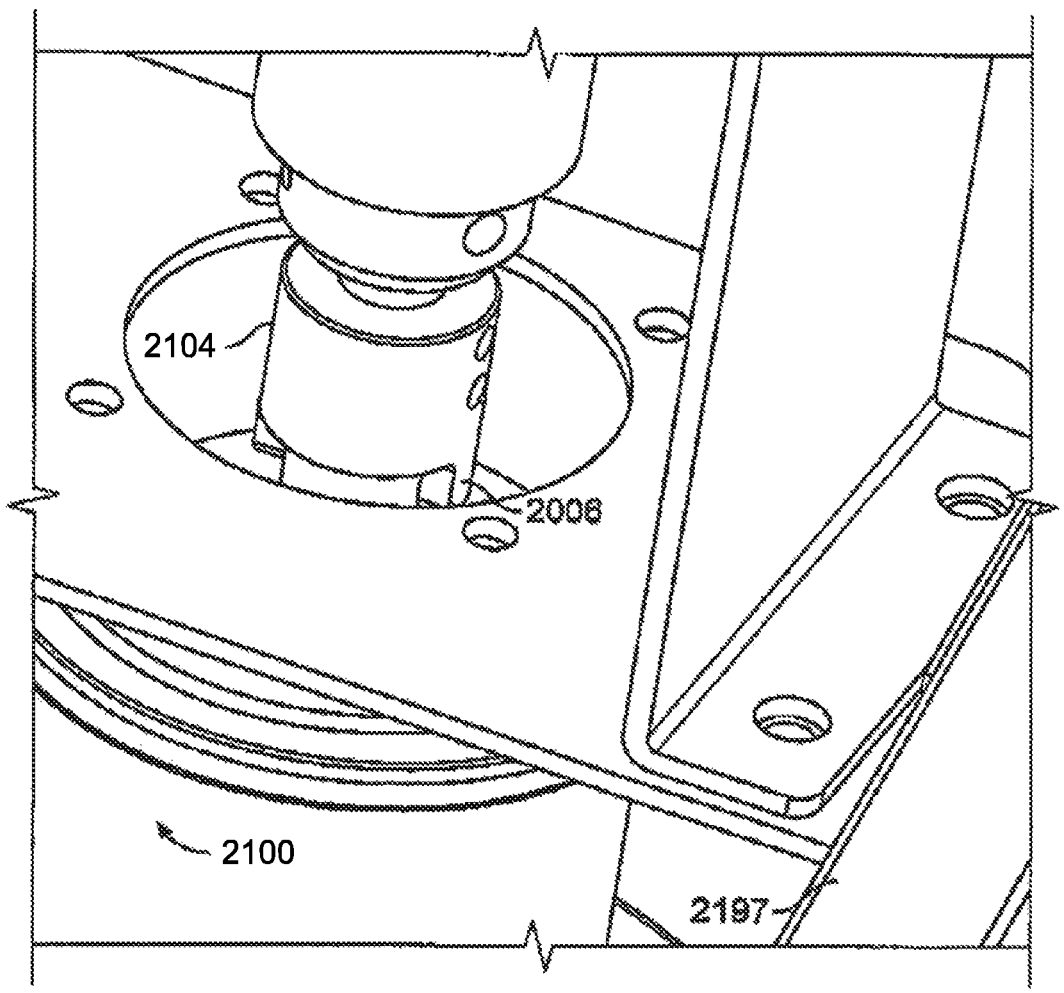
FIG. 21 illustrates a partial perspective view of a reactor system according to one embodiment of the present invention.

FIG. 20 illustrates a partial perspective view of a reactor system 2000 according to one embodiment of the present invention. Reactor system 2000 can include a drive motor 2095 coupled with a drive shaft 2004. Reactor system 2000 can also include a frame support 2097 coupled with drive motor 2095. In use, drive shaft 2004 can be coupled with a rotational assembly 2001 to mix or agitate the contents of a container (not shown) which is coupled with rotational assembly 2001. In some embodiments, rotational assembly 2001 is coupled with frame support 2097 via a bracket (not shown). FIG. 21 illustrates a partial perspective view of a reactor system 2100 according to one embodiment of the present invention. Reactor system 2100 can include a drive motor (not shown) coupled with a drive shaft 2104. Reactor system 2100 can also include a frame support 2197 coupled with the drive motor. Drive shaft 2104 may include or be in operative association with a drive shaft ear 2006 that is configured to couple with a notch of a rotational assembly hub (not shown). Drive shaft ear 2006 is often used to transmit torque from the drive motor to the rotational assembly hub.

Figure 22:
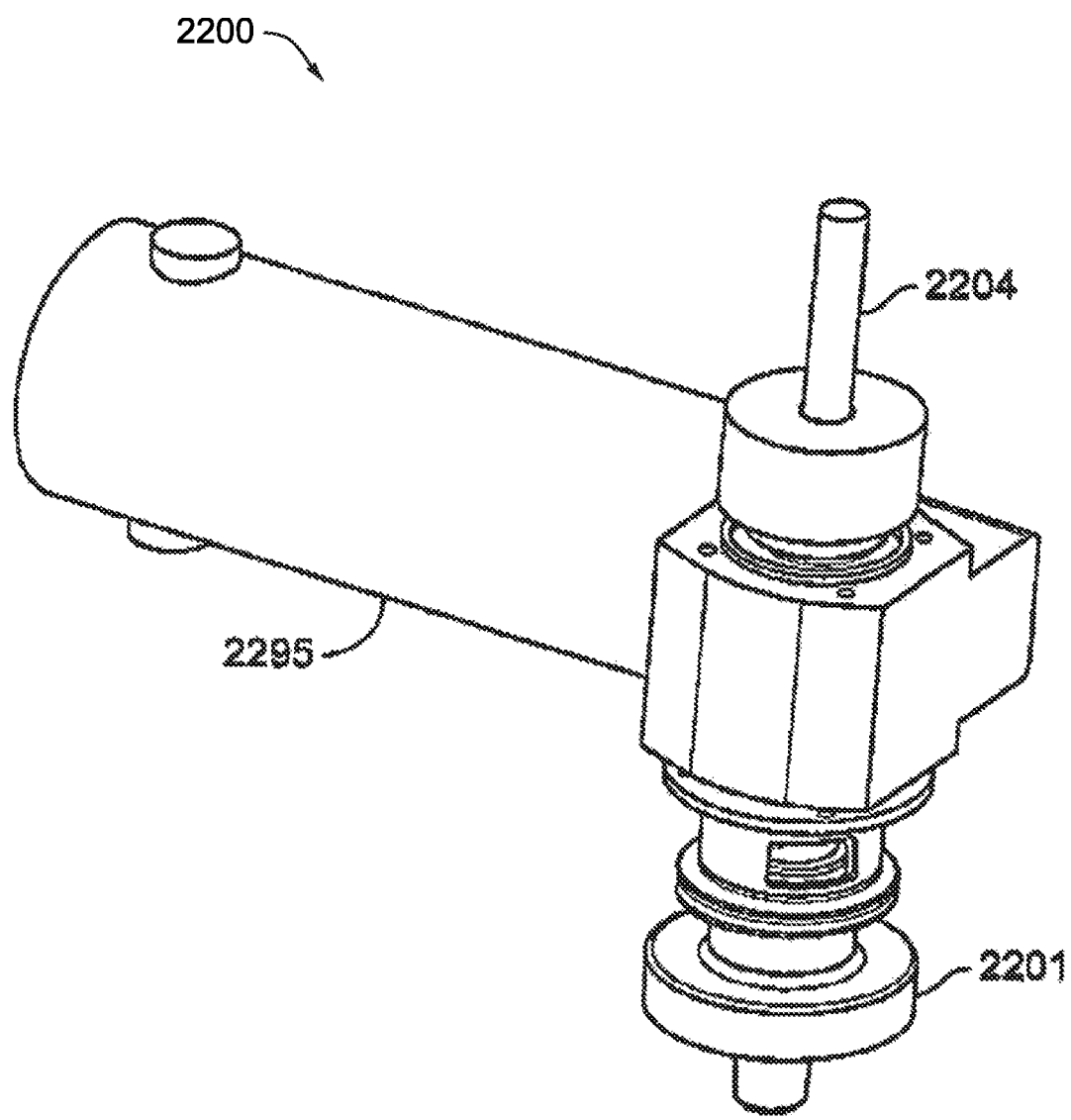
FIG. 22 illustrates a partial perspective view of a reactor system according to one embodiment of the present invention.
Figure 23:
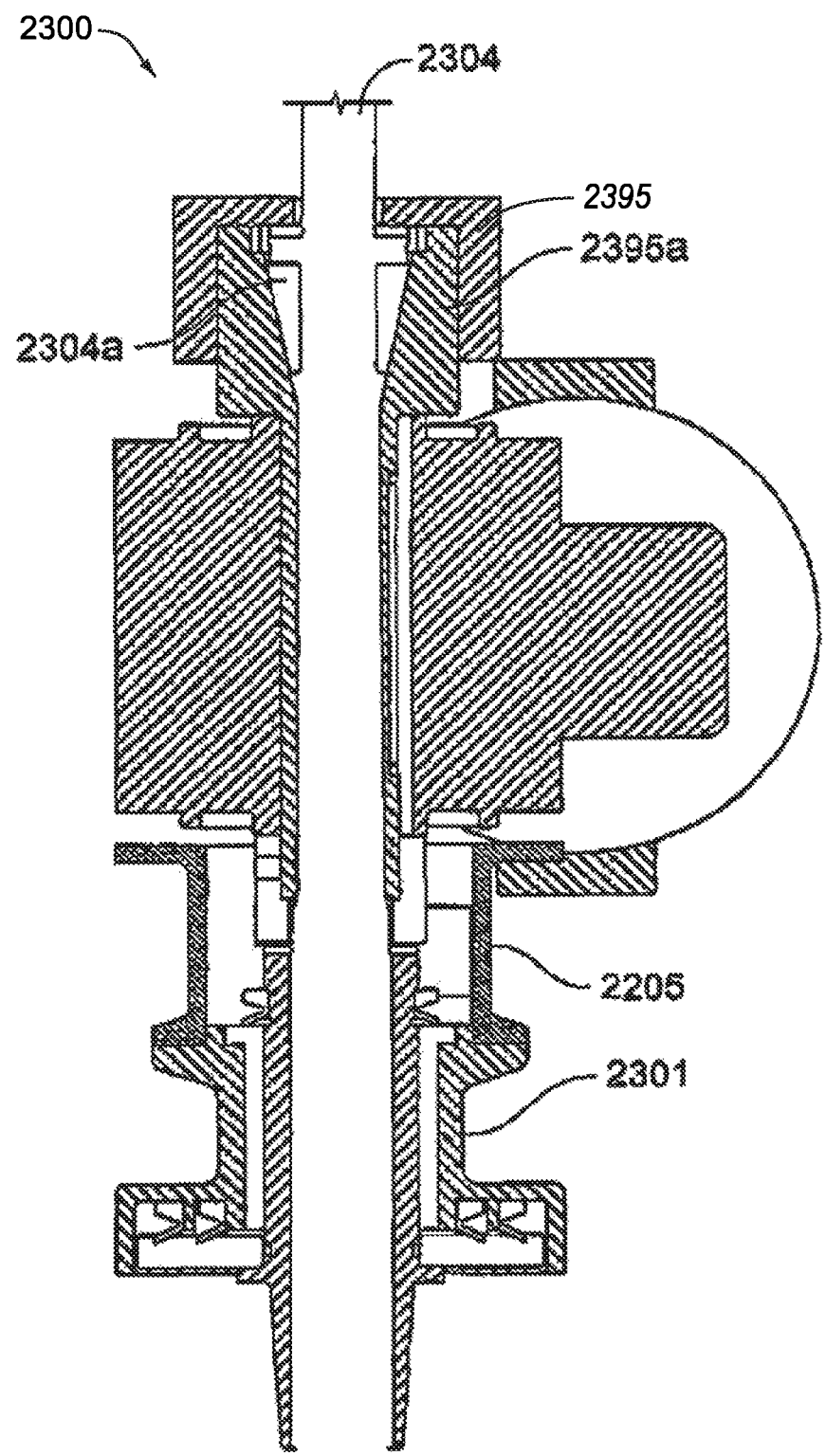
FIG. 23 illustrates a cross-section view of a reactor system according to one embodiment of the present invention.

FIG. 22 illustrates a partial perspective view of a reactor system 2200 according to one embodiment of the present invention. Reactor system 2200 can include a drive motor 2295 coupled with a drive shaft 2204. In use, drive shaft 2204 can be coupled with a rotational assembly 2201 to mix or agitate the contents of a container (not shown) which is coupled with rotational assembly 2201. A clamp 2205 may also be coupled with rotational assembly 2201. In this embodiment, drive motor 2295 includes a right angle gearmotor, which can allow an operator to pass drive shaft 2204 through drive motor 2295 without moving the drive motor 2295. Embodiments that include right angle gear motors, parallel shaft gear motors, and hollow shaft motors can provide enhanced alignment and ease of connection between drive motor 2295 and rotational assembly 2201. FIG. 23 illustrates a cross-section view of a reactor system 2300 according to one embodiment of the present invention. Reactor system 2300 can include a drive motor 2395 coupled with a drive shaft 2304. Drive shaft 2304 may include or be coupled with a tapered element 2304a that is configured to associate with a corresponding receiving element 2395a of motor 2395. Tapered element 2304a can provide enhanced alignment between drive shaft 2304 and drive motor 2395.

Figure 24:
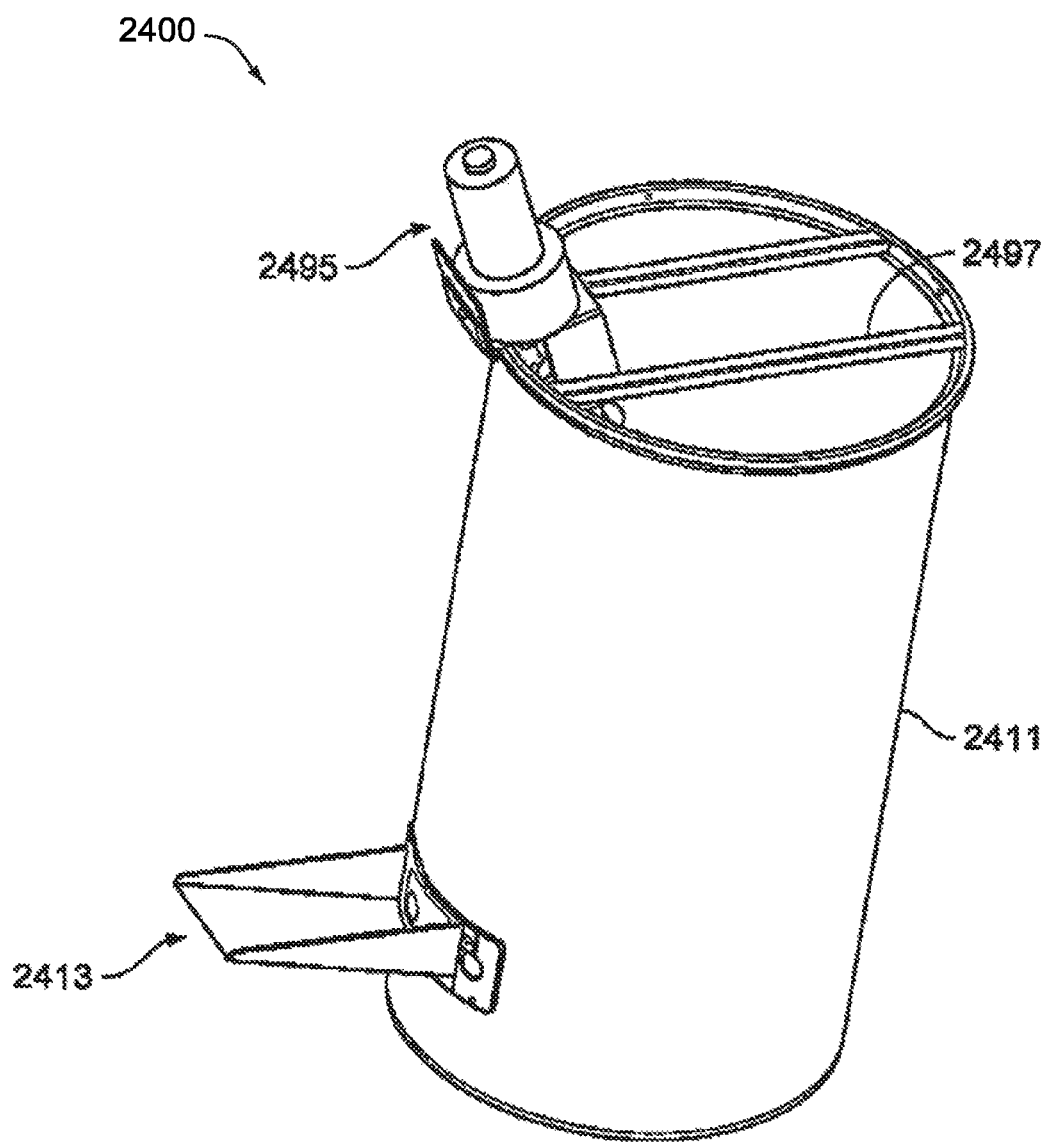
FIG. 24 illustrates a perspective view of a reactor system according to one embodiment of the present invention.
Figure 25:
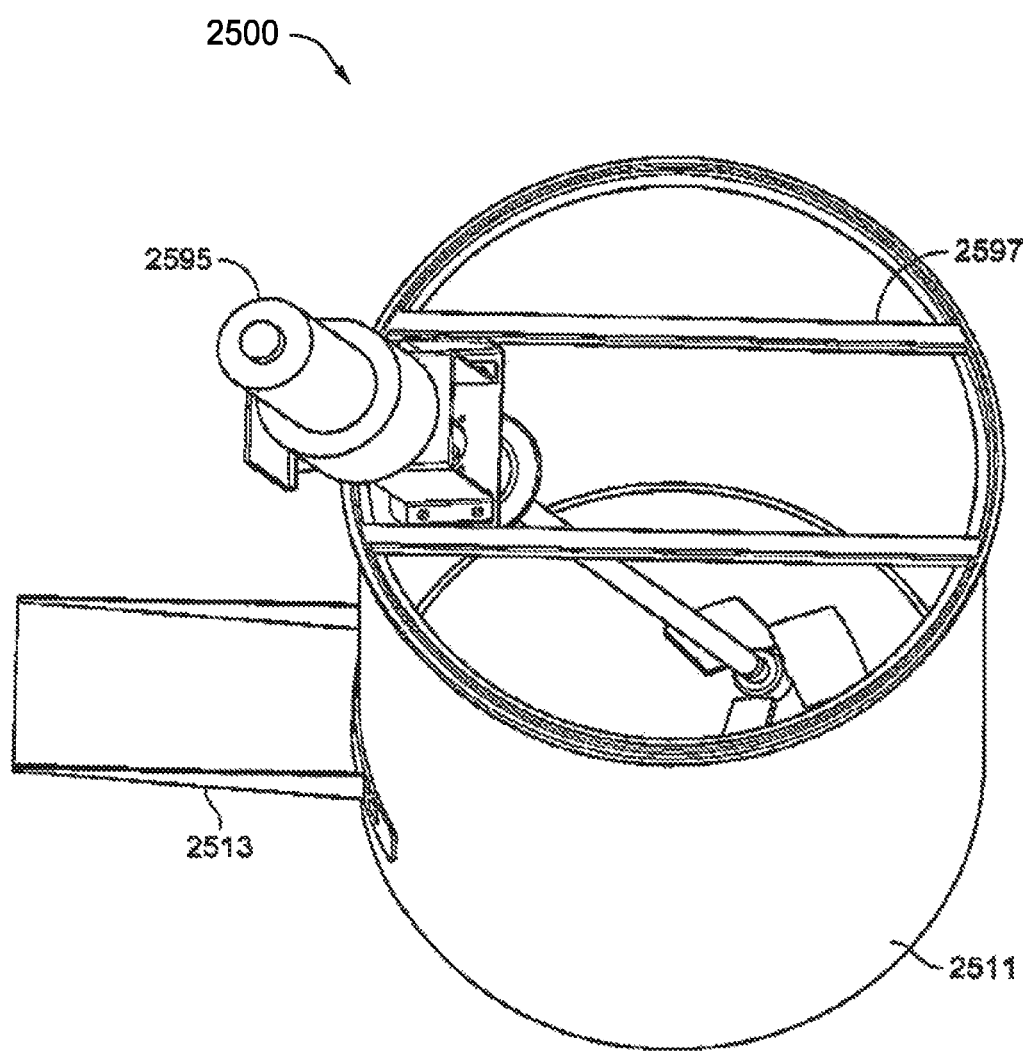
FIG. 25 illustrates a perspective view of a reactor system according to one embodiment of the present invention.

FIG. 24 illustrates a perspective view of a reactor system 2400 according to one embodiment of the present invention. Reactor system 2400 can include a container housing 2411 coupled with a support shelf 2413. Support shelf 2413 may be adapted for supporting sensing probes (not shown) and other elements of a reactor system. Container housing 2411 can be coupled with a drive motor 2495 via a support frame 2497. FIG. 25 illustrates a perspective view of a reactor system 2500 according to one embodiment of the present invention. Reactor system 2500 can include a container housing 2511 coupled with a support shelf 2513. Container housing 2511 can be coupled with a drive motor 2595 via a support frame 2597.

FIG. 26 illustrates a probe assembly 2600 according to one embodiment of the present invention. As seen here, probe assembly 2600 is in a retracted configuration, prior to engagement with a reactor container. Probe assembly 2600 can include a dissolved oxygen and pH probe 2610 and PALL KLEENPAK® connectors 2620 for providing an aseptic connection. Probe assembly 2600 can also include a port 2630, a sleeve 2640, and a coupler 2650, and these three components can facilitate the integration of probe 2610 into the reactor utilizing PALL connectors 2620. In some embodiment, port 2630 and female PALL connector 2720f can be part of or integral with the reactor container (not shown). Sleeve 2640, coupler 2650, and male PALL connector 2720m can be manufactured or provided to the user as a separate subassembly. The user can install the desired probe into such a subassembly and then can sterilize the complete probe assembly. Port 2630, sleeve 2640, and coupler 2650 can facilitate integration of probe 2610 into a bioreactor using PALL connector 2620.

Figure 27A:
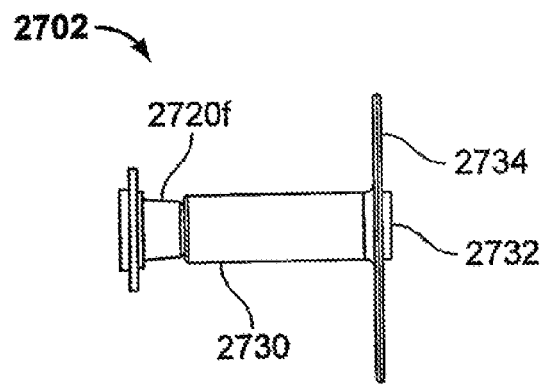
FIG. 27A provides an illustration of a probe port subassembly of a probe assembly according to one embodiment of the present invention.

FIG. 27A provides an illustration of a probe port subassembly 2702 of a probe assembly according to one embodiment of the present invention. Probe port subassembly 2702 can include a bioprocessing container port 2730 coupled with female PALL connector 2720f. Port 2730 may be, for example, heat welded into a container (not shown) via flange plane 2734. Port 2730 may also include a lip seal 2732 that can prevent backflow of fluid or material from the container into probe assembly or beyond flange 2734 plane. In some embodiments, port 2730 and female PALL connector 2720f are constructed integrally with the container.

Figure 27B:
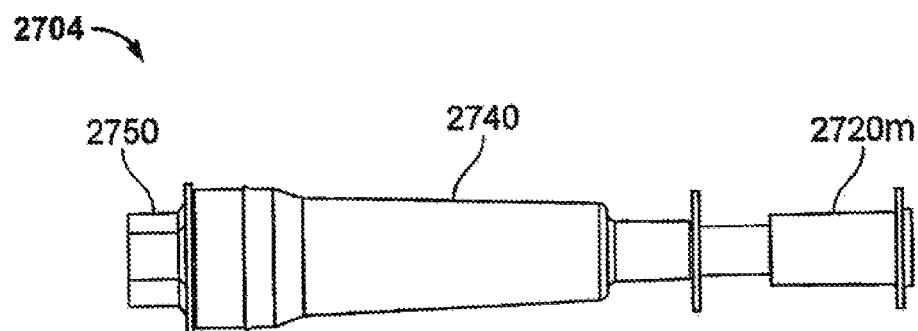
FIG. 27B illustrates a probe kit subassembly of a probe assembly according to one embodiment of the present invention.

FIG. 27B illustrates a probe kit subassembly 2704 of a probe assembly according to one embodiment of the present invention. Probe kit subassembly 2704 can include a coupler 2750, a sleeve 2740, and a male PALL connector 2720m. Probe kit subassembly 2704 may be supplied to an end user as a separate kit. Sleeve 2740 may be coupled with coupler 2750 via a barb fitting (not shown) of coupler 2750. Similarly, sleeve 2740 may be coupled with male PALL connector 2720m via a barb fitting (not shown) of male PALL connector 2720m.

Figure 27C:
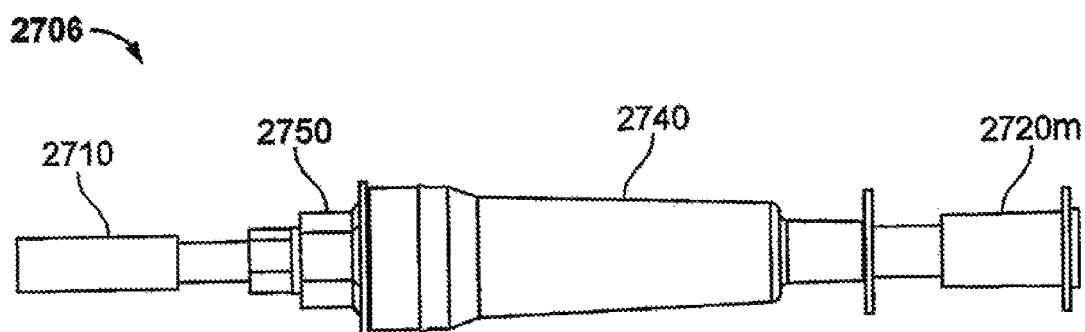
FIG. 27C illustrates an autoclave subassembly of a probe assembly according to one embodiment of the present invention.

FIG. 27C illustrates an autoclave subassembly 2706 of a probe assembly according to one embodiment of the present invention. Autoclave subassembly 2706 can include a probe 2710, coupler 2750, sleeve 2740, and male PALL connector 2720m. An end user can install the desired probe 2710 into a probe kit subassembly 2704 as described above, and sterilize the resulting autoclave assembly 2706. After sterilization, the user can join the male PALL connector 2720m and the female PALL connector 2720f, and complete the probe engagement into the fluid stream. In some embodiments, sleeve 2740 is a flexible member that can collapse and allow probe 2710 to be displaced, and coupler 2750 can provide an interface between sleeve 2740 and probe 2710.

FIG. 28A illustrates a probe assembly 2800 according to one embodiment of the present invention. Probe assembly 2800 includes probe 2810, coupler 2850, sleeve 2840, male PALL connector 2820m, female PALL connector 2820f, and port 2830. Probe assembly 2800 is shown in a first connected configuration, wherein probe assembly is engaged with container, but the probe is not yet introduced into the fluid stream. FIG. 28B illustrates a probe assembly according to one embodiment of the present invention, wherein probe assembly 2800 is in a second connected configuration such that sleeve 2840 is collapsed and a distal end of probe 2810 is introduced into the fluid stream of the container.

C. Cultures

The stirred-tank reactor system can be designed to hold a fluidic medium such as a biological fluid, a cell culture medium, a culture of microorganisms, a food production, or the like. When the fluidic medium is a cell culture the system can be operated in, for example, batch-mode, semi-batch mode, fed-batch mode, or continuous mode. A batch culture can be a large scale cell culture in which a cell inoculum is cultured to a maximum density in a tank or fermenter, and harvested and processed as a batch. A fed-batch culture can be a batch culture which is supplied with either fresh nutrients (e.g., growth-limiting substrates) or additives (e.g., precursors to products). A continuous culture can be a suspension culture that is continuously supplied with nutrients by the inflow of fresh medium, wherein the culture volume is usually constant. Similarly, continuous fermentation can refer to a process in which cells or micro-organisms are maintained in culture in the exponential growth phase by the continuous addition of fresh medium that is exactly balanced by the removal of cell suspension from the bioreactor. Furthermore, the stirred-tank reactor system can be used for suspension, perfusion or microcarrier cultures. Generally, the stirred-tank reactor system can be operated as any conventional stirred-tank reactor with any type of agitator such as a Rushton, hydrofoil, pitched blade, or marine. With reference to FIG. 1, the agitation shaft 112 can be mounted at any angle or position relative to the housing 111, such as upright centered, upright offset, or 15° offset. The control of the stirred-tank reactor system can be by conventional means without the need for steam-in-place (SIP) or clean-in-place (CIP) control. In fact, the system of the instant invention is not limited to sterile bioreactor operation, but can be used in any operation in which a clean product is to be mixed using a stirred tank, for example, food production or any clean-room mixing without the need for a clean-room.

D. The Kit

The invention encompasses a kit that includes a stirred-tank reactor system and instructions for use. In one embodiment, the kit includes a disposable stirred-tank reactor system. Accordingly, the kit includes at least one disposable element such as the bag, the shaft, the impeller, or the bearing. The kit can be entirely disposable. The flexible, disposable bag may be affixed to the shaft and the bearing through at least one seal or o-ring such that the inside of the bag remains sterile. In addition, the bag may include a pH sensor and a dissolved-oxygen sensor, wherein the sensors are incorporated into the bag and are disposable with the bag. The kit may also include one or more internal pouches that are sealed to the bag. The pouch has one end that can be opened to the outside of the bag such that a probe can be inserted into the reactor. The probe may be a temperature probe, a pH probe, a dissolved gas sensor, an oxygen sensor, a carbon dioxide ($CO_2$) sensor, a cell mass sensor, a nutrient sensor, an osmometer, and the like. Furthermore, the system may include at least one port in the bag allowing for the connection of a device to the port, wherein the device includes, but is not limited to, a tube, a filter, a sampler, a probe, a connector, and the like. The port allows for sampling, titration, adding of chemostat reagents, sparging, and the like. The advantage of this kit is that it is optionally entirely disposable and easy-to-use by following the attached instructions. This kit comes in different sizes depending on the preferred culture volume and can be employed with any desired reaction chamber or barrel. This kit is pre-sterilized and requires no validation or cleaning. The kit can be used for cell culture, culture of microorganisms, culture of plant metabolites, food production, chemical production, biopharmaceutical production, and others.

In another embodiment the kit includes a housing or barrel that holds the disposable bag. Such a housing or barrel can be supplied with the bag or provided separately.

E. Examples

The following specific examples are intended to illustrate the invention and should not be construed as limiting the scope of the claims.

(1) A Disposable Bioreactor

One example of a stirred-tank reactor system of the instant invention is a disposable bioreactor, or single use bioreactor (SUB). The bioreactor is similar to a 250 liter media bag with built-in agitation and attachable sensors (e.g., pH sensors, temperature sensors, dissolved oxygen ($dO_2$) sensors, etc.). The reactor is operated via conventional controllers. The agitator (e.g., agitation shaft and impeller) and bearing are disposable and built into the bag. The motor attaches to a support (e.g., motor and bearing support) or bracket(s) on the 250 liter barrel that holds the bag. In size, shape, and operation, this bioreactor appears similar to a stainless steel reactor with a sterile liner, however, the bioreactor of this invention provides a multitude of advantages compared to a conventional stainless steel reactor. It can be appreciated that the size and volume of such media bags can be scaled both upward and downward, according to industry needs.

Most importantly, the need for cleaning and steam sterilization is eliminated. The bag is pre-sterilized by irradiation and, thus, ready for use. In fact, no cleaning, sterilization, validation or testing is required at culture start-up or between culture runs. Consequently, the bioreactor provides a culture environment of zero cross-contamination between runs. In conventional systems, the majority of costs are related to clean-in-progress (CIP) and steam-in-progress (SIP) as well as the design of a skid and control system to oversee these functions. These costs are eliminated in the disposable bioreactor and multiple products may be cultured or manufactured simultaneously and with much greater ease.

The disposable bioreactor can be easily scaled-up by using larger culture bags and larger barrels to hold the bags. Multiple bioreactors can be operated at the same time without any need for extensive engineering or cleaning. The bioreactor is a true stirred tank with well characterized mixing. As such, the bioreactor has the added advantage that it can be scaled and its contents transferred to a stainless steel reactor if desired. Notably, the bioreactor combines ease of use with low cost and flexibility and provides, thus, a new technical platform for cell culture.

(2) Cell Culture

The disposable bioreactor of the instant invention can be used for a batch culture in which cells are inoculated into fresh media. As the cells grow, they consume the nutrients in the media and waste products accumulate. For a secreted product, when the culture has run its course, cells are separated from the product by a filtration or centrifugation step. For viral-vector production, cells are infected with a virus during the growth phase of the culture, allowing expression of the vector followed by harvest. Since there is zero cross-contamination in the bioreactor it works well with batch cultures.

The bioreactor can also be used for perfusion cultures, wherein product and/or waste media is continuously removed and the volume removed is replaced with fresh media. The constant addition of fresh media, while eliminating waste products, provides the cells with the nutrients they require to achieve higher cell concentrations. Unlike the constantly changing conditions of a batch culture, the perfusion method offers the means to achieve and maintain a culture in a state of equilibrium in which cell concentration and productivity may be maintained in a steady-state condition. This can be accomplished in the disposable bag as easily as in any conventional stainless steel reactor. For viral-vector production, the perfusion process allows for an increase in the cell concentration and, thereby the post-infection virus titer. For a secreted product, perfusion in the bioreactor offers the user the opportunity to increase the productivity by simply increasing the size of the culture bag. Most importantly, there is no need for sterilization, validation, or cleaning because the system experiences zero cross-contamination during the production process.

(3) Batch Data 1

Figure 29:
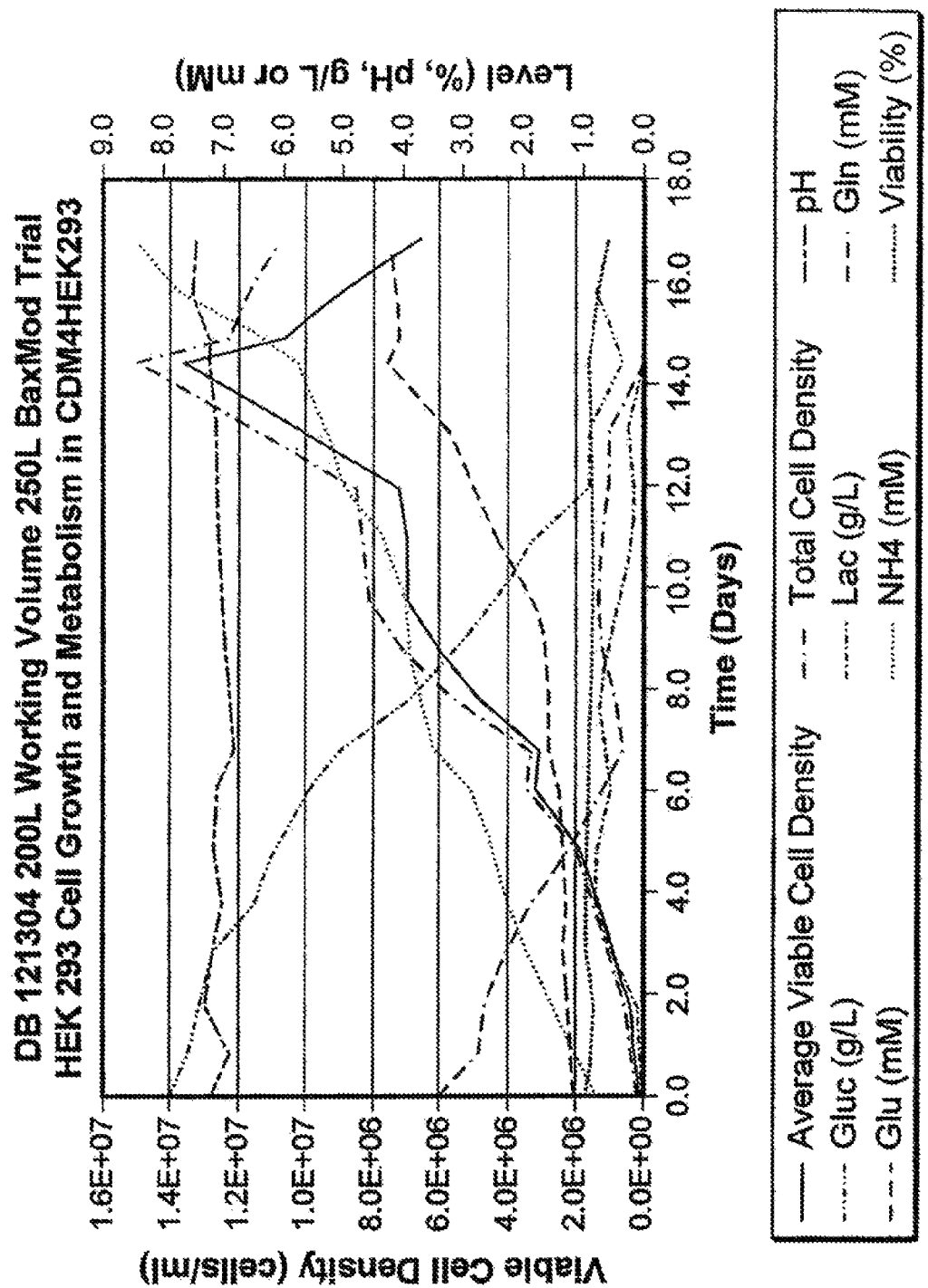
FIG. 29 provides a graph of data that was generated using a reactor system according to one embodiment of the present invention.
Figure 30:
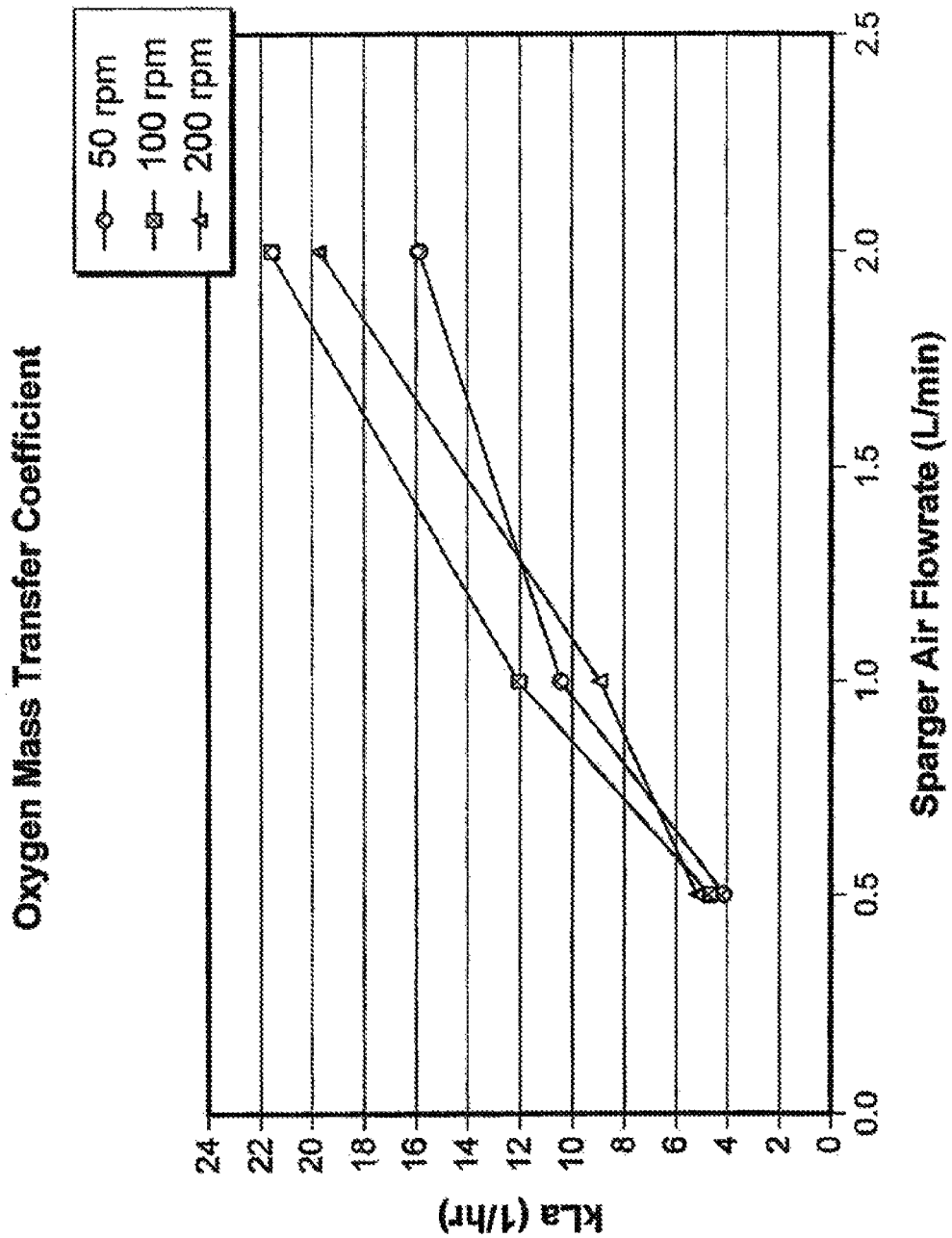
FIG. 30 provides a graph of data that was generated using a reactor system according to one embodiment of the present invention.

FIG. 29 provides a graph of data that was generated using a reactor system according to one embodiment of the present invention. Human embryonic kidney (HEK) 293 cells in 200 liters of CDM4 culture medium were incubated in a 250 liter capacity reactor system. Among other parameters shown in the graph, the viable cell density of the reactor system culture increased for about the first 14 days of the batch run.

(4) Batch Data 2

FIGS. 30-34 illustrate data obtained from a single use bioreactor system for mammalian cell culture according to one embodiment of the present invention. The scaleable mass transfer characteristics of the single use stirred tank bioreactor are described. Cell growth and metabolism, antibody production, and antibody characterization data from batch culture using a 250-liter prototype system are presented and compared to results from a traditional stainless-steel bioreactor of similar scale.

Materials and Methods—Mixing Studies. Mixing time in the bioreactor was estimated at various agitation rates by tracking the change in pH in the reactor over time in response to addition of a base solution. The reactor was filled to working volume of 250 liters with typical cell culture media. At time zero, 500 ml of 1N NaOH was added at the top of the reactor, and a combined pH glass electrode was used to measure pH from time zero until the pH had stabilized. The pH versus time was plotted, and the time required to reach 95% of the final pH was estimated from the graph.

Key scale-up parameters were determined using standard calculations that have been well established in the chemical and pharmaceutical industry.

The mixing Reynolds number, $N_{Re}$ is the ratio of fluid kinetic and inertial forces and is used to determine the mixing regime, either laminar or turbulent:

$$N_{Re}=ND_i^2\rho/\mu.$$

The energy input into the reactor, $P_o$, per volume of the reactor, V, relates to the scale at which fluid mixing and mass transfer occurs and is dependent on the impeller power number, $N_p$:

$$P_o/V=N_p\rho N^3 D_i^5/V$$

The impeller power number depends on the design of the impeller and is a function of number of blades, blade width, and blade pitch. $N_p$ is also a function of the clearance of the impeller from the sides and bottom of the reactor. For various impeller types, the power number is well documented.

Tip speed of the impeller, $v_i$, relates to the fluid shear stress in the vicinity of the impeller:

$$V_i=\pi ND_i$$

In the above equations, N=impeller rotational speed, $D_i$=impeller diameter, $\rho$=fluid density, and $\mu$=fluid viscosity.

Materials and Methods—Oxygen Transfer Studies. The volumetric oxygen transfer coefficient $K_La$, was estimated at various agitation and sparging rates by tracking the change in dissolved oxygen, $dO_2$, concentration over time at the appropriate condition. The reactor was filled to the working volume of 250 liters with typical cell culture media, and a $dO_2$ sensor was installed in the reactor. To prepare for each experiment, nitrogen was sparged through the bioreactor until the $dO_2$ concentration dropped below approximately 20% saturation with air. For each experiment, the agitation rate was set, and then air was sparged at the desired rate. The $dO_2$ concentration was measured versus time until it reached approximately 80% saturation with air. The value of $K_La$ can be estimated from a graph of $C_L$ versus $dC_L/dt$, based on the following mass balance equation:

$$dC_L/dt=K_La(C^*-C_L)$$

where $C_L$ is the $dO_2$ concentration, and $C^*$ is the equilibrium value for $C_L$.

Materials and Methods—Cell Culture Procedures. A cell culture process that had been developed for a traditional stainless-steel reactor of 300-liter working volume was used to demonstrate the performance of the single use bioreactor. The cell line, media, and process parameters that had been demonstrated in the traditional reactor were repeated in the single use reactor.

The cells used were CHO cells expressing a humanized monoclonal antibody. Cells were thawed and maintained in T-flasks using standard methods. Cells were then expanded from T-flasks into custom 1-liter expansion bags prior to being introduced into a traditional stainless-steel 110-liter inocula bioreactor. Once cells reached a concentration of $1.6\times10^6$ cells/ml, 45 liters from the traditional 110-liter bioreactor were used as inocula for the single use bioreactor. Thus, exponentially growing cells from a controlled bioreactor at a pre-determined cell concentration were provided as inocula for the single use bioreactor.

A standard, commercially available, chemically defined cell culture medium was used. At a specified point in the batch culture, a commercially available nutrient feed that is of non-animal origin but is not chemically defined was added. Solutions of D-glucose and L-glutamine were added daily as required during the batch culture to maintain a concentration of D-glucose between 1 and 3 mg/liter and a concentration of L-glutamine between 1 and 3 mMol/liter throughout the batch.

Control of the single use bioreactor was accomplished using standard, industry-accepted sensors and controllers. The temperature, pH, and $dO_2$ feedback controllers operated using proportional, integral, and differential (PID) control. Temperature was measured by a platinum resistance thermometer inserted in a thermo well in the reactor, and was controlled at 37° C. via an electric heat jacket. The pH was measured using a combined pH glass electrode that was in direct contact with the bioreactor contents. The pH was controlled at a value of 7.1 via addition of $CO_2$ into the headspace or addition of 1M $Na_2CO_3$ to the culture. The $dO_2$ concentration was measured using a $dO_2$ sensor that was in direct contact with the bioreactor contents. The $dO_2$ concentration was controlled at 30% saturation with air via sparging of $O_2$ at approximately 0.2 liters/min. Agitation was not controlled by feedback but was maintained at a single set point of 110 rpm and checked daily. Level in the bioreactor was measured using a weigh scale.

A sampling system was attached to the bioreactor using a sterile connection device, and was used to withdraw 10-ml samples as required during the batch culture. Samples were withdrawn at least once daily. Samples were immediately analyzed using a Nova BioProfile 200 analyzer, which provided culture pH, $dO_2$, $dCO_2$, D-glucose, and L-glutamine concentrations. The pH probe was standardized, as required, and D-glucose and L-glutamine solutions were added based on the Nova measurements. Viable and total cell concentrations were determined for each sample based on hemocytometer counts using trypan blue dye exclusion. Samples were filtered through a 0.2 μm filter and stored for later analysis using an Igen based assay for antibody titer.

Key cell culture parameters were calculated based on the sample measurements. Maximum viable cell concentration, cumulative cell time at harvest, final antibody concentration, and total glucose and glutamine consumed were calculated directly from the sample data. As a batch culture, the specific growth rate of the cells, μ, was determined for only the exponential phase of the culture. Specific growth rate was calculated from a regression fit of viable cell concentration, $X_v$, from days one through four following inoculation:

$$dX_v/dt=\mu t$$

Results from a series of batch cultures using a traditional stainless-steel bioreactor of similar scale were available for comparison with the single use results. The ranges of values tabulated for the traditional bioreactor are the 95% prediction intervals for a single fixture observation:

$$x_{mean}\pm t_{\alpha/2,n-1}\cdot s\sqrt{(1+(1/n))}$$

where $x_{mean}$=sample mean, s=sample standard deviation, n=sample size, and $t_{\alpha/2,n-1}$ is the appropriate Student's t-statistic.

The single use bioreactor supernatant was harvested, clarified by filtration and purified (protein A-based affinity purification combined with ion exchange chromatography) using the procedures established for the traditional stainless bioreactor manufacturing process. The resultant purified antibody was characterized and compared to antibody derived from the traditional stainless steel process. Carbohydrate (CHO) profile, SDS-PAGE (reduced and non reduced), SEC-HPLC, SEC-MALS (Multi-Angle Light Scattering), BIACore Binding, RP-HPLC, Capillary Electrophoresis Isoelectric Focusing (CEIEF) and MALDI-TOF Mass Spectrometry assays were utilized to characterize the purified antibodies derived from the single use bioreactor. The results obtained were compared to those seen for antibody produced in a traditional stainless steel bioreactor.

Results—Mixing Studies. The time required to reach 95% homogeneity decreased with increasing agitation speed. Each experiment was repeated twice, and the average mixing times are shown in Table 1.

TABLE 1

Single Use Bioreactor Mixing Studies

| Agitation speed (rpm) | 50 | 100 | 200 |
|---|---|---|---|
| Characteristic mixing time (sec) | 90 | 60 | 45 |

In addition, key scale-up parameters for the single use bioreactor could be readily calculated. The single use bioreactor was designed using design criteria for a typical stirred tank bioreactor, and the impeller was a typical pitched-blade design, as shown in Table 2. In the absence of baffles, vortex formation in the reactor was avoided by mounting the impeller at an offset from center and at a 20° angle from vertical.

TABLE 2

Single Use Bioreactor Design Elements

| Tank height (at working volume) | 1.5 tank diameter |
|---|---|
| Impeller diameter | 0.33 tank diameter |
| Impeller number of blades | 3 |
| Impeller blade pitch | 45° |
| Impeller blade height | 0.5 impeller diameter |
| Impeller clearance from tank bottom | 1 impeller diameter |
| Impeller clearance from tank side | 0.5 impeller diameter |
| Impeller power number (calculated) | 2.1 |

Using the power number from Table 2, characteristic scale-up parameters can be readily calculated for various agitation speeds, as listed in Table 3.

TABLE 3

Single Use Bioreactor Scale-Up Parameters

| Agitation speed (rpm) | 50 | 100 | 200 |
|---|---|---|---|
| Tip speed (cm/sec) | 53 | 106 | 213 |
| Power input per unit volume (hp/1000 liter) | 0.0022 | 0.018 | 0.143 |
| Mixing Reynolds number | 34,000 | 69,000 | 137,000 |

Results—Oxygen Transfer Studies. The volumetric oxygen transfer coefficient, $K_La$ was determined for various flowrates of air through the sparger and for various agitation speeds, shown in FIG. 30. As expected, $K_La$ increased with increasing air flowrate and with increasing agitation speed, with one exception. At 200 rpm, $K_La$ was lower than that at 100 rpm. This discrepancy may be due to an increased surface effect on $K_La$ at the higher agitation rate. (Due to the experimental procedure, the headspace contained a mixture of nitrogen and air.) Further experiments are required to quantify the surface effects.

These results are comparable, as expected, with oxygen transfer characteristics of traditional stirred tank bioreactors of the same geometry. A typical literature value for the equilibrium oxygen concentration in cell culture media is 0.18 mMol/liter, and specific oxygen uptake rate for typical animal cell culture is 0.15 mMol/$10^9$ cells/hr. Operated in the middle of the range from the above chart (agitation=100 rpm; sparge rate=1.0 liter/min; $K_La \approx 10$ hr$^{-1}$) the single use bioreactor is calculated to be capable of maintaining cell concentrations greater than $10 \times 10^6$ cells/ml using air as the sparge gas and greater than $50 \times 10^6$ cells/ml using oxygen as the sparge gas.

Results—Batch Cell Culture. To demonstrate the suitability of the single use bioreactor for cell culture production, CHO cells producing a humanized monoclonal antibody were grown in batch culture and compared to historical results from the same cell line and process carried out in a traditional stainless steel bioreactor of similar scale. This process has been repeated five times in a 300-liter Abec traditional stainless steel reactor that is specifically designed for cell culture. Key cell culture parameters from the two reactors are compared in Table 4.

TABLE 4

Single Use and Traditional Bioreactor Batch Results

| | Single Use Bioreactor (n = 1) | Traditional Bioreactor (n = 5)* |
|---|---|---|
| Duration of Cell Culture (hours) | 285 | 282 ± 8 |
| Maximum Viable Cell Concentration ($10_6$ cells/mL) | 7.6 | 7.4 ± 2.4 |
| Cumulative Viable Cell Time at Harvest($10^9$ cell hr/L) | 1214 | 1019 ± 171 |
| Specific Exponential Growth Rate of Cells (1/hr) | 0.027 | 0.028 ± 0.010 |
| Antibody Concentration at Harvest (% of historical) | 112 | 100 ± 33 |
| Total Glucose Consumed (mg/L) | 14.2 | 15.7 ± 9.4 |
| Total Glutamine Consumed (mMol) | 16.4 | 18.9 ± 2.4 |

*range is the prediction interval for a single future observation

Figure 31:
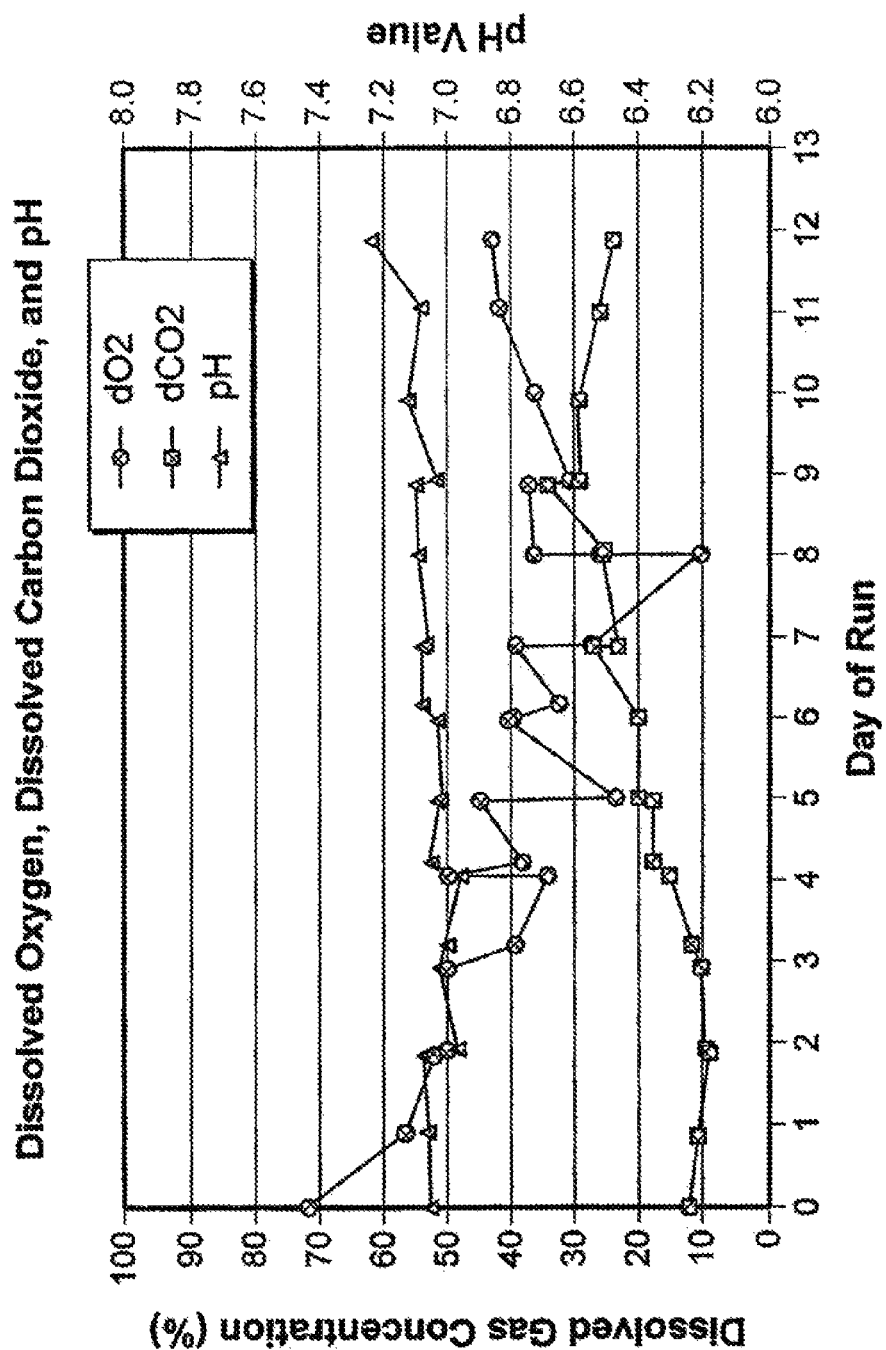
FIG. 31 provides a graph of data that was generated using a reactor system according to one embodiment of the present invention.

The single use bioreactor was an initial prototype. As a prototype being used for the first time, adjustments to the controller PID parameters were made several times during the batch culture. Temporary excursions in pH, $dO_2$ concentration, sparger flowrate, and agitation speed occurred at times during the batch due to these adjustments. Despite these excursions, results from this bioreactor are equivalent to results from the traditional stainless steel bioreactor. Graphs of the pH, $dO_2$, and $dCO_2$ concentration from off-line samples measured by the Nova analyzer are shown in FIG. 31.

Figure 32:
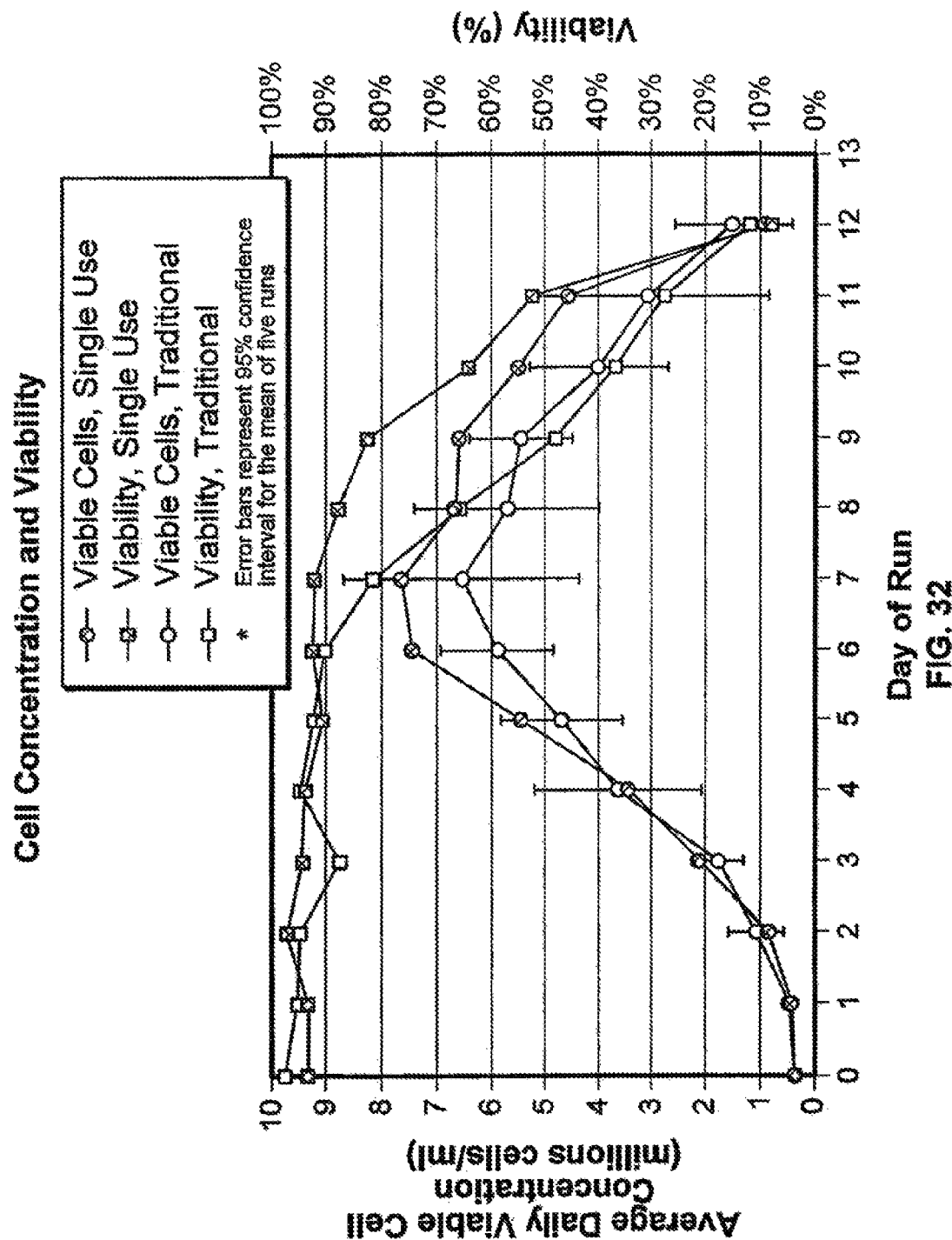
FIG. 32 provides a graph of data that was generated using a reactor system according to one embodiment of the present invention.

Detailed results from the single use bioreactor are shown in the following figures. The single use bioreactor was inoculated at $0.33 \times 10^6$ cells/mL and reached a maximum cell density of $7.6 \times 10^6$ cells/mL. Viability remained above 90% during the growth portion of the batch curve. Total and viable cell concentration and percent viability are shown in FIG. 32.

Figure 33:
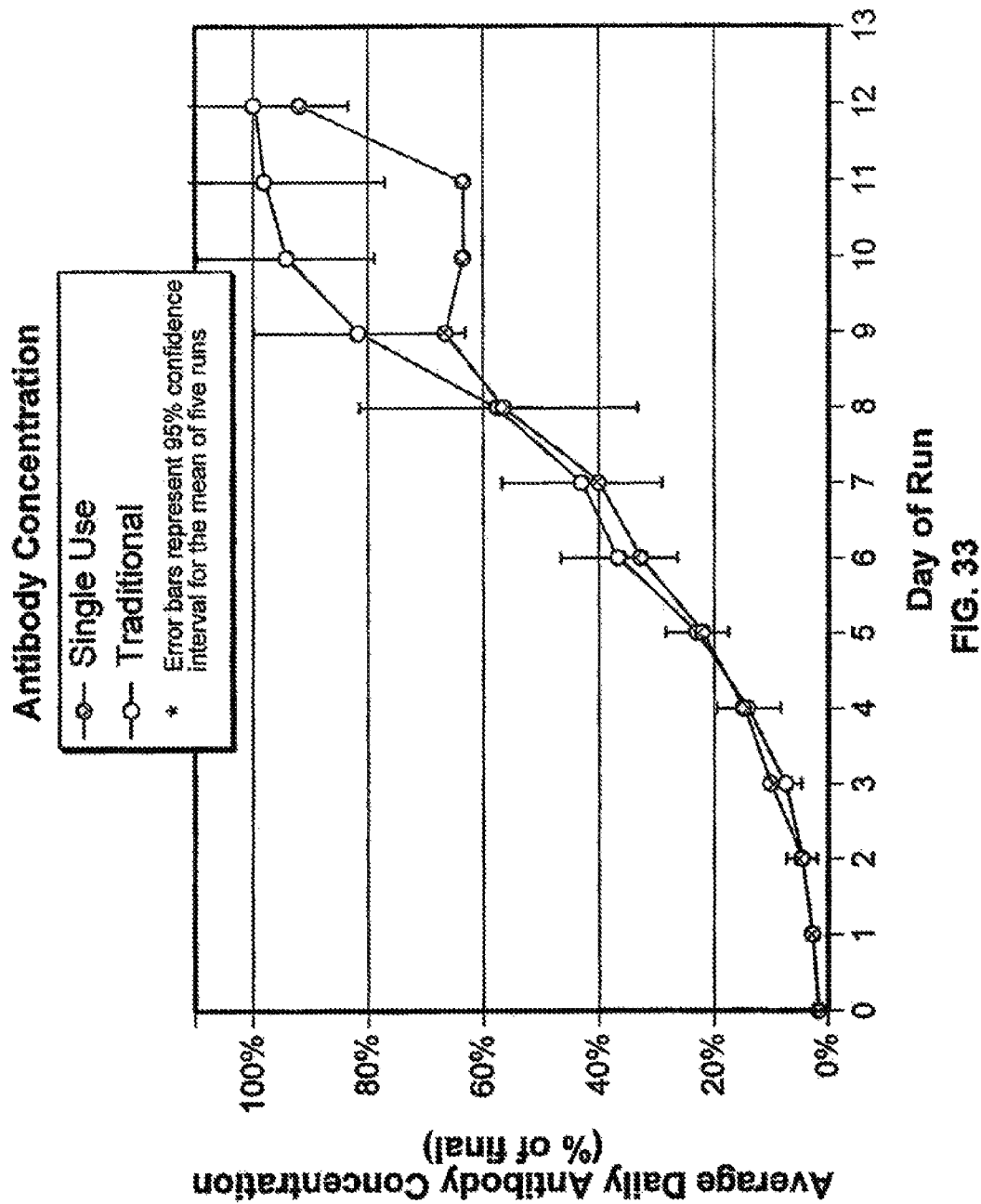
FIG. 33 provides a graph of data that was generated using a reactor system according to one embodiment of the present invention.

Antibody titer over time, as a percent of final titer at harvest, is shown in FIG. 33. As is typical for this cell line, approximately 50% of the antibody was produced in the second half of the batch as the cell concentration was declining.

Figure 34:
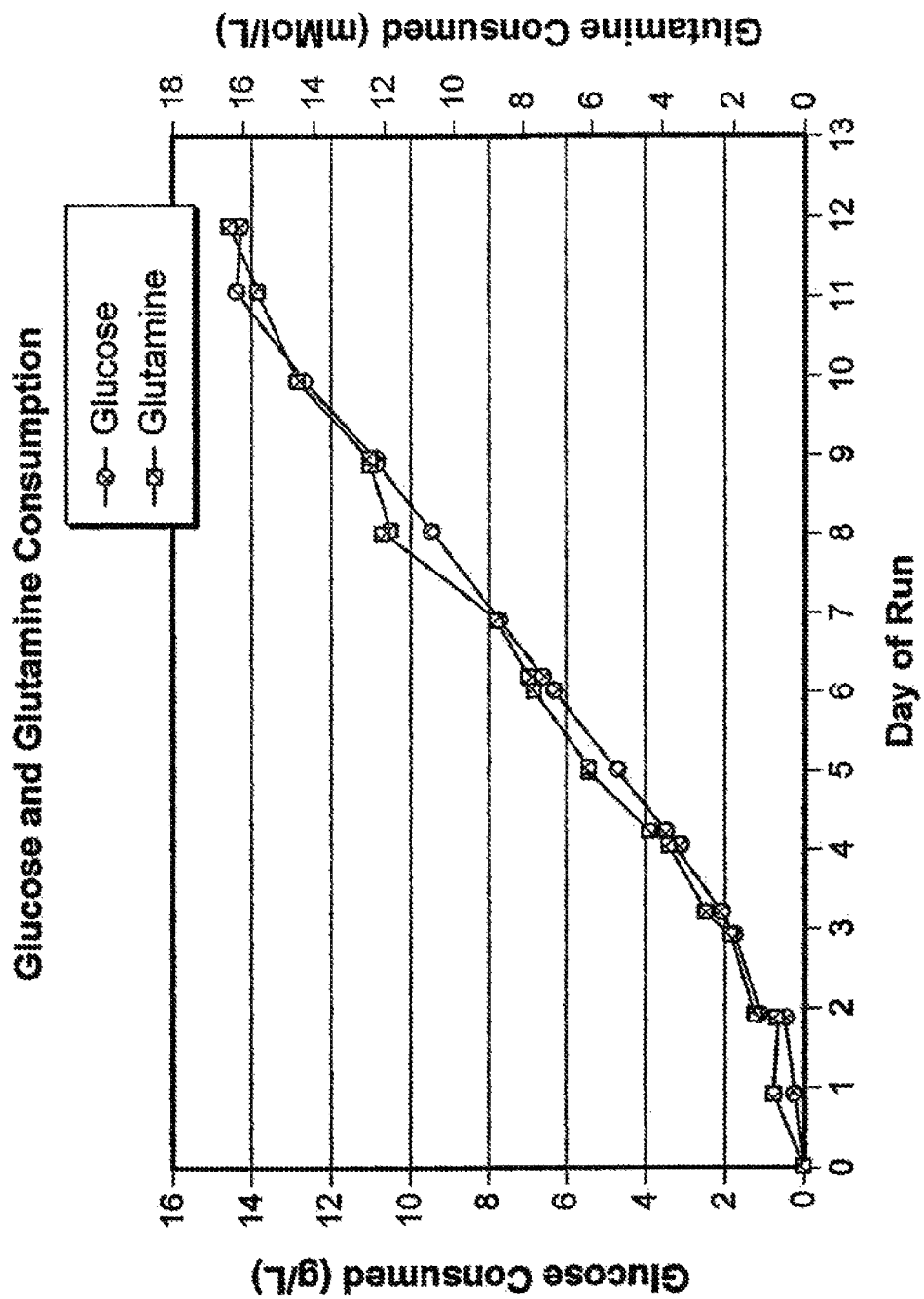
FIG. 34 provides a graph of data that was generated using a reactor system according to one embodiment of the present invention.

Cumulative glucose and glutamine consumption is shown in FIG. 34. Glucose and glutamine consumption for the single use bioreactor was comparable to historical results from the traditional stirred tank bioreactor.

A summary of the assay results is contained in Table 5. In all cases, the antibody derived from the single use bioreactor showed equivalent results to that produced in the traditional stainless steel bioreactor.

TABLE 5

Single Use and Traditional Bioreactor Protein Assay Results

| Assay | Traditional Bioreactor | Single Use Bioreactor |
|---|---|---|
| Carbohydrate (CHO) profile | Comparable to reference | Comparable to reference |
| SDS-PAGE Reduced | Comparable to reference | Comparable to reference |
| SDS-PAGE Non-reduced | Comparable to reference | Comparable to reference |
| SEC-MALS | ~150 KD, >98% monomer | ~150 KD, >98% monomer |
| BIACore Binding | Pass specification | Pass specification |
| CEIEF | Pass specification | Pass specification |
| MALDI-TOF Mass Spec. | ~150 Kd | Comparable to reference |
| RP-HPLC | >95% purity (Pass) | >95% purity (Pass) |
| Peptide Mapping | | Comparable to reference |

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the claims.

What is claimed is:

1. A reactor system comprising:
    a support housing having an interior surface bounding a chamber, the chamber having a vertically extending central longitudinal axis;
    a flexible bag having an interior surface bounding a compartment, the flexible bag being disposed within the chamber of the support housing;
    a mixing element disposed within the compartment of the flexible bag; and
    a drive shaft having a first end secured to the mixing element within the compartment of the flexible bag and an opposing second end disposed outside of the flexible bag, wherein the mixing element is laterally offset by a distance from the vertically extending central longitudinal axis of the support housing; and
    a rotational assembly which includes a casing mounted to the flexible bag and a hub rotatably mounted to the casing, the drive shaft passing through the hub.

2. The reactor system as recited in claim 1, wherein the mixing element comprises an impeller having an impeller body and a plurality of pitched impeller blades radially outwardly projecting from the impeller body, wherein the mixing element is laterally offset from the vertically extending central longitudinal axis of the support housing so that the impeller body is spaced apart from the vertically extending central longitudinal axis of the support housing.

3. The reactor system as recited in claim 2, wherein the drive shaft projects into the impeller body.

4. The reactor system as recited in claim 1, wherein the mixing element comprises an impeller having a rotational axis about which the impeller rotates, wherein the mixing element is laterally offset from the vertically extending central longitudinal axis of the support housing so that the rotational axis is offset from the vertically extending central longitudinal axis of the support housing.

5. The reactor system as recited in claim 4, wherein the rotational axis is angled relative to the vertically extending central longitudinal axis of the support housing by a defined angle greater than zero.

6. The reactor system as recited in claim 1, wherein the mixing element is rotatably coupled to the flexible bag.

7. The reactor system as recited in claim 1, further comprising:
    an elongated tubular connector disposed within the compartment of the flexible bag, the tubular connector having a first end connected to the bag and an opposing second end disposed within the compartment;
    the mixing element comprising an impeller disposed within the compartment of the flexible bag, the impeller being coupled with the second end of the tubular connector; and
    the drive shaft removably received within the tubular connector and removably coupled with the impeller such that rotation of the drive shaft facilitates rotation of the impeller.

8. The reactor system as recited in claim 7, further comprising the hub having a passageway extending therethrough, the first end of the tubular connector being secured to the hub.

9. A reactor system comprising:
    a support housing having an interior surface bounding a chamber;
    a flexible bag having an interior surface bounding a compartment, the flexible bag being disposed within the chamber of the support housing;
    an impeller disposed within the compartment of the flexible bag, the impeller having a rotational axis about which the impeller rotates;
    a drive shaft secured to the impeller, wherein the rotational axis of the impeller is angled relative to vertical by a defined angle greater than zero; and
    a rotational assembly which includes a casing mounted to the flexible bag and a hub rotatably mounted to the casing, the drive shaft extending from the hub to the impeller.

10. The reactor system as recited in claim 9, wherein the chamber of the support housing has a vertically extending central longitudinal axis, the rotational axis of the impeller being angled relative to the vertically extending central longitudinal axis by the defined angle greater than zero.

11. The reactor system as recited in claim 9, wherein the impeller is rotatably secured to the flexible bag.

12. The reactor system as claimed in claim 9, wherein the drive shaft rotates the impeller.

13. The reactor system as recited in claim 9, wherein the impeller comprises an impeller body and a plurality of pitched impeller blades radially outwardly projecting from the impeller body, the drive shaft projecting into the impeller body.

14. The reactor system as recited in claim 9, wherein the drive shaft has a central longitudinal axis being disposed at the same angle as the rotational axis.

15. The reactor system as recited in claim 9, further comprising:
    an elongated tubular connector disposed within the compartment of the flexible bag, the tubular connector having a first end connected to the bag and an opposing second end disposed within the compartment;

the impeller being disposed within the compartment of the flexible bag and coupled with the second end of the tubular connector; and the drive shaft being removably received within the tubular connector and removably coupled with the impeller such that rotation of the drive shaft facilitates rotation of the impeller.

16. The reactor as recited in claim 15, further comprising the first end of the tubular connector being secured to the hub.

17. The reactor system as claimed in claim 16, wherein rotation of the drive shaft facilitates rotation of the impeller, hub, and tubular connector.

18. The reactor system as claimed in claim 15, wherein the tubular connector comprises a flexible tube.

19. The reactor system as recited in claim 1, further comprising:
the drive shaft having a central longitudinal axis extending along the length thereof; and
a drive motor coupled to the drive shaft such that activation of the drive motor causes rotation of the drive shaft about the central longitudinal axis of the drive shaft.

20. The reactor system as recited in claim 19, wherein the drive motor is coupled to the drive shaft such that activation of the drive motor causes rotation of the drive shaft about the central longitudinal axis of the drive shaft without lateral displacement of the drive shaft.

21. The reactor system as recited in claim 9, wherein the impeller comprises an impeller body and three spaced apart impeller blades radially outwardly projecting from the impeller body.

22. The reactor system as recited in claim 14, further comprising a drive motor coupled to the drive shaft such that activation of the drive motor causes rotation of the drive shaft about the central longitudinal axis of the drive shaft.

23. The reactor system as recited in claim 14, further comprising a drive motor, the drive motor being coupled to the drive shaft such that activation of the drive motor causes rotation of the drive shaft about the central longitudinal axis of the drive shaft without lateral displacement of the drive shaft.

* * * * *